United States Patent
Csaszar et al.

(10) Patent No.: US 9,984,285 B2
(45) Date of Patent: *May 29, 2018

(54) ADAPTIVE TRACKING SYSTEM FOR SPATIAL INPUT DEVICES

(71) Applicant: Oblong Industries, Inc., Los Angeles, CA (US)

(72) Inventors: Ambrus Csaszar, Los Angeles, CA (US); Dima Kogan, Los Angeles, CA (US); Paul Yarin, Los Angeles, CA (US)

(73) Assignee: Oblong Industries, Inc., Los Angeles, CA (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/644,092

(22) Filed: Jul. 7, 2017

(65) Prior Publication Data

US 2017/0308743 A1    Oct. 26, 2017

Related U.S. Application Data

(63) Continuation of application No. 14/606,563, filed on Jan. 27, 2015, which is a continuation of application
(Continued)

(51) Int. Cl.
*G06F 3/033* (2013.01)
*G06K 9/00* (2006.01)
(Continued)

(52) U.S. Cl.
CPC .......... *G06K 9/00355* (2013.01); *G06F 3/011* (2013.01); *G06F 3/014* (2013.01);
(Continued)

(58) Field of Classification Search
CPC ...... G06F 3/017; G06F 3/0325; G06F 3/0346; G06F 3/0425; G06F 3/0428
See application file for complete search history.

(56) References Cited

U.S. PATENT DOCUMENTS

| | | |
|---|---|---|
| 4,843,568 A | 6/1989 | Krueger et al. |
| 5,454,043 A | 9/1995 | Freeman |

(Continued)

FOREIGN PATENT DOCUMENTS

| | | |
|---|---|---|
| EP | 0899651 | 3/1999 |
| EP | 1883238 | 1/2008 |

(Continued)

OTHER PUBLICATIONS

Bretzner, Lars et al. "A Prototype System for Computer Vision Based Human Computer Interaction", Technical report CVA251, ISRN KTH NA/P—Jan. 2009—SE. Department of Numerical Analysis and Computer Science, KTH (Royal Institute of Technology), S-100 44 Stockh.

(Continued)

*Primary Examiner* — Vijay Shankar
(74) *Attorney, Agent, or Firm* — Jeffrey Schox

(57) ABSTRACT

An adaptive tracking system for spatial input devices provides real-time tracking of spatial input devices for human-computer interaction in a Spatial Operating Environment (SOE). The components of an SOE include gestural input/output; network-based data representation, transit, and interchange; and spatially conformed display mesh. The SOE comprises a workspace occupied by one or more users, a set of screens which provide the users with visual feedback, and a gestural control system which translates user motions into command inputs. Users perform gestures with body parts and/or physical pointing devices, and the system translates those gestures into actions such as pointing, dragging, selecting, or other direct manipulations. The tracking system provides the requisite data for creating an immersive environment by maintaining a model of the spatial relationships between users, screens, pointing devices, and other physical objects within the workspace.

20 Claims, 29 Drawing Sheets

Related U.S. Application Data

No. 13/532,527, filed on Jun. 25, 2012, now Pat. No. 8,941,589, which is a continuation-in-part of application No. 12/572,689, filed on Oct. 2, 2009, now Pat. No. 8,866,740, and a continuation-in-part of application No. 12/572,698, filed on Oct. 2, 2009, now Pat. No. 8,830,168, and a continuation-in-part of application No. 12/109,263, filed on Apr. 24, 2008, now Pat. No. 8,407,725, and a continuation-in-part of application No. 12/417,252, filed on Apr. 2, 2009, now Pat. No. 9,075,441, and a continuation-in-part of application No. 12/487,623, filed on Jun. 18, 2009, now abandoned, and a continuation-in-part of application No. 12/553,845, filed on Sep. 3, 2009, now Pat. No. 8,531,396, and a continuation-in-part of application No. 12/553,902, filed on Sep. 3, 2009, now Pat. No. 8,537,111, and a continuation-in-part of application No. 12/553,929, filed on Sep. 3, 2009, now Pat. No. 8,537,112, and a continuation-in-part of application No. 12/557,464, filed on Sep. 10, 2009, and a continuation-in-part of application No. 12/579,340, filed on Oct. 14, 2009, now Pat. No. 9,063,801, and a continuation-in-part of application No. 12/579,354, filed on Oct. 14, 2009, now Pat. No. 8,370,383, and a continuation-in-part of application No. 12/579,372, filed on Oct. 14, 2009, now Pat. No. 9,052,970, and a continuation-in-part of application No. 12/773,605, filed on May 4, 2010, now Pat. No. 8,681,098, and a continuation-in-part of application No. 12/773,667, filed on May 4, 2010, now Pat. No. 8,723,795, and a continuation-in-part of application No. 12/789,129, filed on May 27, 2010, and a continuation-in-part of application No. 12/789,262, filed on May 27, 2010, now Pat. No. 8,669,939, and a continuation-in-part of application No. 12/789,302, filed on May 27, 2010, now Pat. No. 8,665,213, and a continuation-in-part of application No. 13/430,509, filed on Mar. 26, 2012, now Pat. No. 8,941,588, and a continuation-in-part of application No. 13/430,626, filed on Mar. 26, 2012, now Pat. No. 8,896,531.

(51) Int. Cl.
| | |
|---|---|
| *G06F 3/01* | (2006.01) |
| *G06F 3/03* | (2006.01) |
| *H04N 5/247* | (2006.01) |
| *H04N 7/18* | (2006.01) |
| *G06F 19/00* | (2018.01) |
| *H04N 5/232* | (2006.01) |

(52) U.S. Cl.
CPC ............ *G06F 3/017* (2013.01); *G06F 3/0325* (2013.01); *G06F 19/701* (2013.01); *H04N 5/232* (2013.01); *H04N 5/247* (2013.01); *H04N 7/18* (2013.01); *H04N 7/181* (2013.01)

(56) References Cited

U.S. PATENT DOCUMENTS

| | | | |
|---|---|---|---|
| 5,581,276 A | 12/1996 | Cipolla et al. |
| 5,594,469 A | 1/1997 | Freeman et al. |
| 5,651,107 A | 7/1997 | Frank et al. |
| 5,982,352 A | 11/1999 | Pryor |
| 6,002,808 A | 12/1999 | Freeman |
| 6,043,805 A | 3/2000 | Hsieh |
| 6,049,798 A | 4/2000 | Bishop et al. |
| 6,072,494 A | 6/2000 | Nguyen |
| 6,075,895 A | 6/2000 | Qiao et al. |
| 6,191,773 B1 | 2/2001 | Maruno et al. |
| 6,198,485 B1 | 3/2001 | Mack et al. |
| 6,215,890 B1 | 4/2001 | Matsuo et al. |
| 6,222,465 B1 | 4/2001 | Kumar et al. |
| 6,256,033 B1 | 7/2001 | Nguyen |
| 6,351,744 B1 | 2/2002 | Landresse |
| 6,385,331 B2 | 5/2002 | Harakawa et al. |
| 6,456,728 B1 | 9/2002 | Doi et al. |
| 6,501,515 B1 | 12/2002 | Iwamura |
| 6,515,669 B1 | 2/2003 | Mohri |
| 6,703,999 B1 | 3/2004 | Iwanami et al. |
| 6,807,583 B2 | 10/2004 | Hrischuk et al. |
| 6,819,782 B1 | 11/2004 | Imagawa et al. |
| 6,950,534 B2 | 9/2005 | Cohen et al. |
| 7,034,807 B2 | 4/2006 | Maggioni |
| 7,042,440 B2 | 5/2006 | Pryor et al. |
| 7,050,606 B2 | 5/2006 | Paul et al. |
| 7,058,204 B2 | 6/2006 | Hildreth et al. |
| 7,109,970 B1 | 9/2006 | Miller |
| 7,129,927 B2 | 10/2006 | Hans |
| 7,145,551 B1 | 12/2006 | Bathiche et al. |
| 7,159,194 B2 | 1/2007 | Wong et al. |
| 7,164,117 B2 | 1/2007 | Breed et al. |
| 7,170,492 B2 | 1/2007 | Bell |
| 7,227,526 B2 | 6/2007 | Hildreth et al. |
| 7,229,017 B2 | 6/2007 | Richley et al. |
| 476,788 A1 | 8/2007 | Lin |
| 7,259,747 B2 | 8/2007 | Bell |
| 7,280,346 B2 | 10/2007 | Lewis et al. |
| 7,340,077 B2 | 3/2008 | Gokturk et al. |
| 7,348,963 B2 | 3/2008 | Bell |
| 7,366,368 B2 | 4/2008 | Morrow et al. |
| 7,372,977 B2 | 5/2008 | Fujimura et al. |
| 7,379,563 B2 | 5/2008 | Shamaie |
| 7,379,566 B2 | 5/2008 | Hildreth |
| 7,379,613 B2 | 5/2008 | Dowski, Jr. et al. |
| 7,389,591 B2 | 6/2008 | Jaiswal et al. |
| 7,421,093 B2 | 9/2008 | Hildreth et al. |
| 7,428,542 B1 | 9/2008 | Fink et al. |
| 7,428,736 B2 | 9/2008 | Dodge et al. |
| 7,430,312 B2 | 9/2008 | Gu |
| 7,436,595 B2 | 10/2008 | Cathey, Jr. et al. |
| 7,466,308 B2 | 12/2008 | Dehlin |
| 7,519,223 B2 | 4/2009 | Dehlin et al. |
| 7,555,142 B2 | 6/2009 | Hildreth et al. |
| 7,555,613 B2 | 6/2009 | Ma |
| 7,559,053 B2 | 7/2009 | Krassovsky et al. |
| 7,570,805 B2 | 8/2009 | Gu |
| 7,574,020 B2 | 8/2009 | Shamaie |
| 7,576,727 B2 | 8/2009 | Bell |
| 7,598,942 B2 | 10/2009 | Underkoffler et al. |
| 7,627,834 B2 | 12/2009 | Rimas-Ribikauskas et al. |
| 7,665,041 B2 | 2/2010 | Wilson et al. |
| 7,685,083 B2 | 3/2010 | Fairweather |
| 7,692,131 B2 | 4/2010 | Fein et al. |
| 7,725,547 B2 | 5/2010 | Albertson et al. |
| 7,822,267 B2 | 10/2010 | Gu |
| 7,827,698 B2 | 11/2010 | Jaiswal et al. |
| 7,834,846 B1 | 11/2010 | Bell |
| 7,848,542 B2 | 12/2010 | Hildreth |
| 7,850,526 B2 | 12/2010 | Zalewski et al. |
| 7,854,655 B2 | 12/2010 | Mao et al. |
| 7,898,522 B2 | 3/2011 | Hildreth et al. |
| 7,949,157 B2 | 5/2011 | Afzulpurkar et al. |
| 7,966,353 B2 | 6/2011 | Wilson |
| 7,979,850 B2 | 7/2011 | Ivanov et al. |
| 7,984,452 B2 | 7/2011 | Chakravarty et al. |
| 7,991,920 B2 | 8/2011 | Back et al. |
| 8,059,089 B2 | 11/2011 | Daniel |
| 8,094,873 B2 | 1/2012 | Kelusky et al. |
| 8,116,518 B2 | 2/2012 | Shamaie et al. |
| 8,212,550 B2 | 7/2012 | Katsurahira et al. |
| 8,254,543 B2 | 8/2012 | Sasaki et al. |
| 8,259,996 B2 | 9/2012 | Shamaie |
| 8,269,817 B2 | 9/2012 | Kumar et al. |
| 8,274,535 B2 | 9/2012 | Hildreth et al. |
| 8,280,732 B2 | 10/2012 | Richter et al. |
| 8,300,042 B2 | 10/2012 | Bell |
| 8,325,214 B2 | 12/2012 | Hildreth |

(56) References Cited

U.S. PATENT DOCUMENTS

| | | |
|---|---|---|
| 8,341,635 B2 | 12/2012 | Arimilli et al. |
| 8,355,529 B2 | 1/2013 | Wu et al. |
| 8,363,098 B2 | 1/2013 | Rosener et al. |
| 8,370,383 B2 | 2/2013 | Kramer et al. |
| 8,407,725 B2 | 3/2013 | Kramer et al. |
| 8,472,665 B2 | 6/2013 | Hildreth |
| 8,531,396 B2 | 9/2013 | Underkoffler et al. |
| 8,537,111 B2 | 9/2013 | Underkoffler et al. |
| 8,537,112 B2 | 9/2013 | Underkoffler et al. |
| 8,559,676 B2 | 10/2013 | Hildreth |
| 8,565,535 B2 | 10/2013 | Shamaie |
| 8,625,849 B2 | 1/2014 | Hildreth et al. |
| 8,659,548 B2 | 2/2014 | Hildreth |
| 8,666,115 B2 | 3/2014 | Perski et al. |
| 8,669,939 B2 | 3/2014 | Underkoffler et al. |
| 8,681,098 B2 | 3/2014 | Underkoffler et al. |
| 8,704,767 B2 | 4/2014 | Dodge et al. |
| 8,723,795 B2 | 5/2014 | Underkoffler et al. |
| 8,726,194 B2 | 5/2014 | Hildreth |
| 8,745,541 B2 | 6/2014 | Wilson et al. |
| 8,769,127 B2 | 7/2014 | Selimis et al. |
| 8,830,168 B2 * | 9/2014 | Underkoffler ........... G06F 3/017 345/158 |
| 8,856,691 B2 | 10/2014 | Geisner et al. |
| 8,866,740 B2 * | 10/2014 | Underkoffler ........... G06F 3/017 345/158 |
| 8,941,589 B2 * | 1/2015 | Csaszar ................ G06K 7/0008 345/158 |
| 9,063,801 B2 | 6/2015 | Kramer et al. |
| 9,213,890 B2 | 12/2015 | Huang et al. |
| 9,261,979 B2 | 2/2016 | Shamaie et al. |
| 9,465,457 B2 | 10/2016 | Thompson et al. |
| 9,684,380 B2 | 6/2017 | Kramer et al. |
| 9,740,293 B2 | 8/2017 | Kramer et al. |
| 9,740,922 B2 * | 8/2017 | Csaszar .............. G06K 9/00355 |
| 2002/0065950 A1 | 5/2002 | Katz et al. |
| 2002/0085030 A1 | 7/2002 | Ghani |
| 2002/0184401 A1 | 12/2002 | Kadel et al. |
| 2002/0186200 A1 | 12/2002 | Green |
| 2003/0048280 A1 | 3/2003 | Russell |
| 2004/0125076 A1 | 7/2004 | Green |
| 2005/0212753 A1 | 9/2005 | Marvit et al. |
| 2006/0269145 A1 | 11/2006 | Roberts |
| 2007/0288467 A1 | 12/2007 | Strassner et al. |
| 2008/0208517 A1 | 8/2008 | Shamaie |
| 2008/0222660 A1 | 9/2008 | Tavi et al. |
| 2010/0060568 A1 | 3/2010 | Fisher et al. |
| 2010/0315439 A1 | 12/2010 | Huang et al. |
| 2012/0229383 A1 | 9/2012 | Hamilton et al. |
| 2012/0239396 A1 | 9/2012 | Johnston et al. |

FOREIGN PATENT DOCUMENTS

| | | |
|---|---|---|
| WO | 009972 | 10/1989 |
| WO | 035633 | 7/1999 |
| WO | 134452 | 11/2008 |
| WO | 030822 | 3/2010 |

OTHER PUBLICATIONS

Addison-Wesley: "Inside Macintosh-vol. I", vol. I Chapter 1-8, Jan. 1, 1985 (Jan. 1, 1985), pp. 1-58.

Bacon J., et al., "Using Events to Build Distributed Applications", Second International Workshop on Services in Distributed and Networked Environments, 1995, pp. 148-155.

Jiang H., et al., "Denis: A Dynamic Event Model for Interactive Systems", Proceedings of the Acm Symposium on Virtual Reality Software and Technology, 2002, pp. 97-104.

Johanson B., et al., "The Event Heap: A Coordination Infrastructure for Interactive Workspaces", Proceedings Fourth IEEE Workshop on Mobile Computing Systems and Applications, 2002, pp. 83-93.

Johanson B., et al., "The Interactive Workspaces Project: Experiences with Ubiquitous Computing Rooms", IEEE Pervasive Computing, 2002, vol. 1 (2), pp. 67-74.

Mansouri-Samani M., et al., "A Configurable Event Service for Distributed Systems", Third International Conference on Annapolis Configurable Distributed Systems, 1996, pp. 210-217.

Michael J Carey., et al., "The Architecture of the Exodus Extensible Dbms", Proceeding OODS, 1986, pp. 52-65.

Rubine D., "Specifying Gestures by Example", Computer Graphics, 1991, vol. 25 (4), pp. 329-337.

Velipasalar S., et al., "Specifying, Interpreting and Detecting High-level, Spatio-Temporal Composite Events in Single and Multi-Camera Systems", Conference on Computer Vision and Pattern Recognition Workshop, 2006, pp. 110-110.

William A McCuskey., "On Automatic Design of Data Organization", American Federation of Information Processing Societies, 1970, pp. 187-199.

* cited by examiner

1. Depict pose with left hand as viewed from back

| | |
|---|---|
| p = | pinkie finger |
| r = | ring finger |
| m = | middle finger |
| i = | index finger |
| t = | thumb |

| | |
|---|---|
| ^ | = curled non-thumb |
| > | = curled thumb |
| \| | = straight finger or thumb pointed straight up |
| \ or / | = straight finger or thumb pointed at angle |
| - | = thumb pointing straight sideways |
| x | = finger or thumb pointing into plane |

| Pose name | p | r | m | i | t |
|---|---|---|---|---|---|
| | | | Hand Pose | | |
| flat | \| | \| | \| | \| | \| |
| fist | ^ | ^ | ^ | ^ | > |
| mime gun | ^ | ^ | ^ | \| | - |
| 2 or peace | ^ | ^ | \ | / | > |
| one-finger point | ^ | ^ | ^ | \| | > |
| two-finger point | ^ | ^ | \| | \| | > |
| x-y-z | ^ | ^ | x | \| | - |
| ok | \| | \| | \| | ^ | > |
| pinkie point | \| | ^ | ^ | ^ | > |
| bracket | x | x | x | x | x |
| 4 | \ | \ | \| | / | > |
| 3 | ^ | \ | \| | / | > |
| 5 | \ | \ | \| | / | / |

Figure 3

2. Add hand orientation to complete pose must specify two variables:
    1. palm direction (if hand were flat)
    2. finger direction (if hand were flat)

| | |
|---|---|
| - | medial |
| + | lateral |
| x | anterior |
| * | posterior |
| ^ | cranial |
| v | caudal | orientation variables come after colon, e.g.:

| | | |
|---|---|---|
| ^ ^ x \| - : - x | = | x-y-z start position |
| ^ ^ \ / > : * v | = | upside-down v |

Figure 4

3. Two-hand combos

| Hand 1 | Hand 2 | Pose |
|---|---|---|
| ^ ^ ^ ^ > : x ^ | ^ ^ ^ ^ > : x ^ | full stop |
| ^ ^ ^ \| - : x - | ^ ^ ^ \| - : x ^ | snapshot |
| \| \| \| \| \| : v x | \| \| \| \| \| : - x | rudder and throttle start position |

Figure 5

| Gest I.D. | Description | Hand 1 Pose | Hand 1 Motion | Hand 2 Pose | Hand 2 Motion |
|---|---|---|---|---|---|
| 1 | point at object (invoke and move cursor) | ^^^\|-:-x | point mime gun | | |
| 2 | select object | ^^^\|:-x | drop thumb to select | | |
| 3 | move spatially / zoom in/out | ^^\|-:-x | rotate/translate | | |
| 4 | snapshot | ^^^\|-:x- | make square with 2 hands | ^^^\|-:x^ | make square with 2 hands |
| 5 | demarcate rectangular region | ^^^\|-:x- | make square then adjust size | ^^^\|-:x^ | make square then adjust size |
| 6 | clear the decks | \|\|\|\|:+x | sweep hand laterally | \|\|\|\|:-x | sweep hand medially |
| 7 | organize objects into a circle | ^^^\|-:-^ | look through circle of O.K. sign | | |
| 8 | two-finger point at objects | ^^\|-:-x | point | | |
| 9 | two-finger select object | ^^^\|:-x | drop thumb to select | | |
| 10 | mark start time | xxxxx:-^ | strike pose | | |
| 11 | mode change I | \|\|\|\|:-^ | strike pose - make "T" with two hands | \|\|\|\|:v- | strike pose - make "T" with two hands |
| 12 | mode change II | \|\|\|\|:-^ | strike pose - parallel hands | \|\|\|\|:-^ | strike pose - parallel hands |
| 13 | push back and slide workspace | \|\|\|\|-:x^ | push palm toward screen -- move sideways to find new regions | | |

Figure 8A

| # | Command | Gesture notation | | | Description |
|---|---|---|---|---|---|
| 14 | enter sub-application | ‖‖‖‖ | :x^ | strike pose | |
| 15 | return from sub-application | ‖‖‖‖ | :.^ | strike pose | |
| 16 | select option | ^^^ | -:-x | medial roll | |
| 17 | roll time forward/back | ‖‖‖‖ | :vx | | Yaw hand at elbow while keeping hand parallel to floor |
| 18 | stop time | ‖‖‖‖ | :x^ | strike pose | |
| 19 | loop time | ^^^ | -:x^ | | circular motion with "L" |
| 20 | demarcate irregular region | ^^^ | -:vx | | start with 2 finger tips together. 1 hand holds start position. other hand traces out shape - select "click" for vertices |
| 21 | tag object | ^^^>: | -x | | pinky-point at object then roll hand medially |
| 22 | group data streams | ^^^ | -:vx | bring finger tips of two hands together | ^^^ | -:vx | bring finger tips of two hands together |
| 23 | restore encapsulated workspace | ‖‖‖‖ | :+x | sweep hand medially | ‖‖‖‖ | :-x | sweep hand laterally |

Figure 8B first quadword of every slaw

|  | 76543210 | 76543210 | 76543210 | 76543210 |
|---|---|---|---|---|
| length-follows: | 1xxxxxxx | xxxxxxxx | xxxxxxxx | xxxxxxxx |
| eight-byte length: | 11xxxxxx | xxxxxxxx | xxxxxxxx | xxxxxxxx |
| wee cons: | 01xxxxxx | xxxxxxxx | xxxxxxxx | xxxxxxxx |
| wee cons quadlen: | rrqqqqqq | qqqqqqqq | qqqqqqqq | qqqqqqqq |
| wee string: | 001xxxxx | xxxxxxxx | xxxxxxxx | xxxxxxxx |
| wee string quadlen: | rrrqqqqq | qqqqqqqq | qqqqqqqq | qqqqqqqq |
| wee list: | 0001xxxx | xxxxxxxx | xxxxxxxx | xxxxxxxx |
| wee list quadlen: | rrrrqqqq | qqqqqqqq | qqqqqqqq | qqqqqqqq |
| full string: | 1*100000 | 00000000 | 00000000 | 00000001 |
| full cons: | 1*100000 | 00000000 | 00000000 | 00000010 |
| full list: | 1*100000 | 00000000 | 00000000 | 00000011 |

(the penulti-MSB above is zero or one as the length is contained in the next one or two quadwords, i.e. if it's a four or eight byte length, per the 'eight-byte length' bit description second from top)

| numeric: | 00001xxx | xxxxxxxx | xxxxxxxx | xxxxxxxx |
|---|---|---|---|---|
| numeric float: | xxxxx1xx | xxxxxxxx | xxxxxxxx | xxxxxxxx |
| numeric complex: | xxxxxx1x | xxxxxxxx | xxxxxxxx | xxxxxxxx |
| numeric unsigned: | xxxxxxx1 | xxxxxxxx | xxxxxxxx | xxxxxxxx |
| numeric wide: | xxxxxxxx | 1xxxxxxx | xxxxxxxx | xxxxxxxx |
| numeric stumpy: | xxxxxxxx | x1xxxxxx | xxxxxxxx | xxxxxxxx |
| numeric reserved: | xxxxxxxx | xx1xxxxx | xxxxxxxx | xxxxxxxx |

Figure 14B (wide and stumpy conspire to express whether the number in question is 8, 16, 32, or 64 bits long; neither-wide-nor-stumpy, i.e. both zero, is sort of canonical and thus means 32 bits; stumpy alone is 8; stumpy and wide is 16; and just wide is 64)

```
numeric 2-vector:      xxxxxxxx  xxx01xxx  xxxxxxxx  xxxxxxxx
numeric 3-vector:      xxxxxxxx  xxx10xxx  xxxxxxxx  xxxxxxxx
numeric 4-vector:      xxxxxxxx  xxx11xxx  xxxxxxxx  xxxxxxxx
``` for any numeric entity, array or not, a size-in-bytes-minus-one is stored in the last eight bits -- if a singleton, this describes the size of the data part; if an array, it's the size of a single element -- so:

```
num'c unit bsize mask:  00001xxx  xxxxxxxx  xxxxxxxx  mmmmmmmm
``` and for arrays, there're these:

```
num'c breadth follows:   xxxxxxxx  xxxxx1xx  xxxxxxxx  xxxxxxxx
num'c 8-byte breadth:    xxxxxxxx  xxxxx11x  xxxxxxxx  xxxxxxxx
num'c wee breadth mask:  xxxxxxxx  xxxxx0mm  mmmmmmmm  xxxxxxxx
```

Figure 14C

ADAPTIVE TRACKING SYSTEM FOR SPATIAL INPUT DEVICES

CROSS-REFERENCE TO RELATED APPLICATIONS

This application is a continuation of U.S. application Ser. No. 14/606,563, filed 27 Jan. 2015, which is a continuation of U.S. application Ser. No. 13/532,527, filed 25 Jun. 2012, now issued as U.S. Pat. No. 8,941,589, which claims the benefit of U.S. Provisional Application Ser. No. 61/500,416, filed Jun. 23, 2011.

This application is a continuation of U.S. application Ser. No. 14/606,563, filed 27 Jan. 2015, which is a continuation-in-part application of U.S. application Ser. Nos. 12/572,689, 12/572,698, 12/109,263, 12/417,252, 12/487,623, 12/553,845, 12/553,902, 12/553,929, 12/557,464, 12/579,340, 12/579,354, 12/579,372, 12/773,605, 12/773,667, 12/789,129, 12/789,262, 12/789,302, 13/430,509, and 13/430,626.

TECHNICAL FIELD

Embodiments are described relating to control systems and devices and, more particularly, for detecting and initializing in vision-based tracking systems.

BACKGROUND

There is a need for adaptive tracking systems for spatial input devices that provide real-time tracking of spatial input devices for human-computer interaction (HCI) in a Spatial Operating Environment (SOE).

INCORPORATION BY REFERENCE

Each patent, patent application, and/or publication mentioned in this specification is herein incorporated by reference in its entirety to the same extent as if each individual patent, patent application, and/or publication was specifically and individually indicated to be incorporated by reference.

BRIEF DESCRIPTION OF THE DRAWINGS

FIG. 3 is a diagram of poses in a gesture vocabulary, under an embodiment.

FIG. 4 is a diagram of orientation in a gesture vocabulary, under an embodiment.

FIG. 5 is a diagram of two hand combinations in a gesture vocabulary, under an embodiment.

FIGS. 8A and 8B show example commands, under an embodiment.

FIGS. 14B and 14C show a slaw header format, under an embodiment.

DETAILED DESCRIPTION

Embodiments described herein include an adaptive tracking system for spatial input devices that provides real-time tracking of spatial input devices for human-computer interaction (HCI) in a Spatial Operating Environment (SOE). The components of an SOE, which is analogous to an operating system, include gestural input/output; network-based data representation, transit, and interchange; and spatially conformed display mesh. The SOE comprises a workspace occupied by one or more users, a set of screens which provide the users with visual feedback, and a gestural control system which translates user motions into command inputs. Users perform gestures with body parts and/or physical pointing devices, and the system translates those gestures into actions such as pointing, dragging, selecting, or other direct manipulations. The tracking system provides the requisite data for creating an immersive environment by maintaining a model of the spatial relationships between users, screens, pointing devices, and other physical objects within the workspace.

Figure 1A:
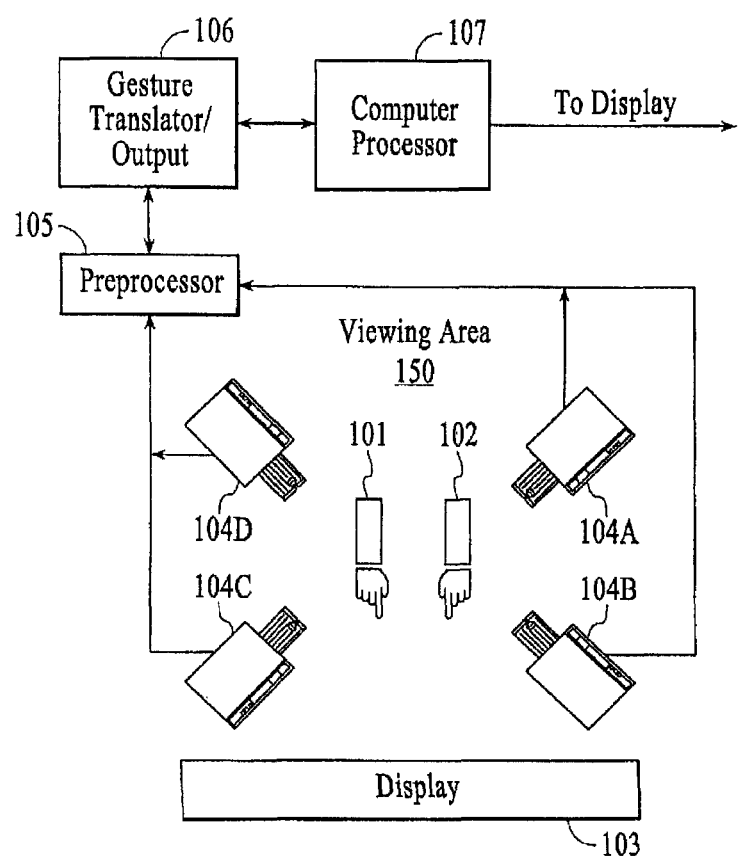
FIG. 1A is a block diagram of a Spatial Operating Environment (SOE), under an embodiment.

Embodiments of the systems and methods are provided in the context of the SOE described in detail below. Generally, FIG. 1A is a block diagram of a Spatial Operating Environment (SOE), under an embodiment. The SOE, which includes a gestural control system, or gesture-based control system, can alternatively be referred to as a Spatial User Interface (SUI) or a Spatial Interface (SI). Tracking as described herein includes the process of detecting and localizing the position of one or more spatial input devices. In the context of a SOE or other gestural interface, such tracking is used to determine when the user is trying to communicate with the system, to provide basic information needed for detecting and recognizing temporally extended gestures, and to allow for real-time control and feedback for interactions.

The adaptive tracking system of an embodiment provides real-time tracking of spatial input devices for human-computer interaction in a SOE that comprises a workspace occupied by one or more users, a set of screens which provide the users with visual feedback, and a gestural control system which translates user motions into command inputs. Users perform gestures with body parts and/or physical pointing devices, and the system translates those gestures into actions such as pointing, dragging, selecting, or other direct manipulations. The functions and purpose of such a system are described in detail herein and in the Related Applications.

The lowest layer of the gestural control system is the component which tracks the users' motions within the workspace. The tracking component uses sensors to capture and digitize physical motions, providing the foundation for the gesture detection and translation layer.

Camera-based systems in which the tracking component uses cameras to capture physical motions have been used in the motion picture and video game industries to digitize and record the three-dimensional (3D) motions of actors and objects. While the cameras provide an easily accessible set of hardware and software, such systems may not be best-suited for a direct application to HCI because they require rigid camera mounting, a great deal of camera overlap and/or a large number of cameras, a calibration prior to use to capture data, significant human intervention to initialize object tracking, and sometimes, a post-processing step to clean up data inconsistencies.

In contrast, computer users may expect their input devices to work without extensive configuration. For example, a user may attach a peripheral (e.g. keyboard or mouse) to his personal computer and begin using it immediately. The motion tracking system for HCI of an embodiment performs in a similar manner, without excessive configuration or maintenance requirements imposed upon the user.

Central to the tracking system and gestural control of an embodiment is the concept of coincident virtual and physical spaces, wherein the system creates the feeling that the virtual information displayed on the screens within the workspace is simply an extension of the physical workspace. The Related Applications describe examples that include literal pointing, automatic compensation for movement or repositioning of screens, graphics that change depending on user position, and inclusion of physical objects in on-screen display, to name a few.

To provide the requisite data for creating such an immersive environment, the tracking system of an embodiment maintains a model of the spatial relationships between users, screens, pointing devices, and other physical objects within the workspace. Embodiments include a motion tracking system with characteristics that make it well-suited for use in a real-time gestural control system. The characteristics include, but are not limited to, the following: fast bootstrapping of the system without calibration; the ability to cover a workspace with a relatively small number of sensors; modeling of the spatial relationships between sensors, screens, users, pointing devices, and other objects within the workspace; fast, automatic adaptation to accidental or intentional reconfiguration of the workspace; and real-time sensor fusion to produce spatially consistent motion tracking without post-processing. The motion tracking system of an embodiment uses cameras and hardware similar to that used for conventional motion capture.

Figure 1B:
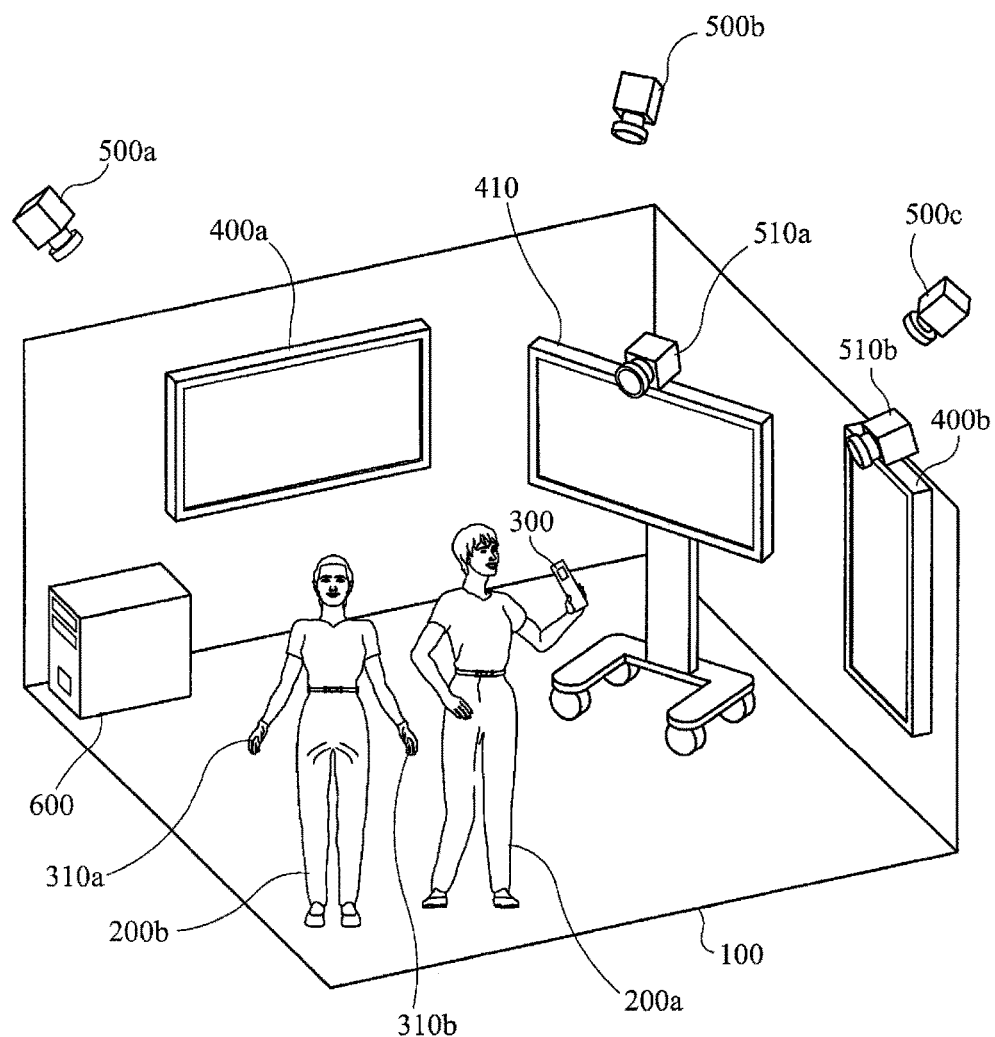
FIG. 1B is a block diagram of the motion tracking system, under an embodiment.

The components of the motion tracking system of an embodiment include sensors, tags, computing hardware, and software, but may not be so limited. FIG. 1B is a block diagram of the motion tracking system, under an embodiment. The motion tracking system operates in a workspace environment 100 occupied by users 200 having tagged wands 300 and/or tagged gloves 310, and using applications rendered on fixed screens 400 and mobile screens 410. Tag sensing is provided by fixed cameras mounted within the workspace 500 and attached to screens 510, while computing hardware and software 600 runs the sensing algorithms and user applications.

Sensors of the tracking system collect information about the locations and orientations (poses) of tags within the workspace. Tags are particular objects which are easily detectable, identifiable, and localizable from data collected by the sensors. The computing hardware and software fuse data from the sensors to create a model of the motions and spatial relationships between screens, sensors, and tags. The system of an embodiment makes no other restriction on what constitutes a tag, other than that there exist a sensing device capable of measuring the 6-degree-of-freedom (DOF) pose comprising the location and orientation of the tag relative to the sensor. Objects of interest (e.g. pointing devices, users' body parts, clothing, gloves, screens, etc.) are adorned with tags which are tracked by the system.

During use, the system of an embodiment automatically builds a coherent estimate for the spatial relationships between sensors, screens, and tagged objects in the workspace. Each sensor estimates the pose of each tag within its sensing volume. Each sensor's sensing volume partially overlaps at least one other sensor's sensing volume, and the combined sensing volume of all sensors is contiguous to allow a coherent and complete model to be built. Furthermore, measurements of all sensors are synchronized to the same clock, although sensors need not necessarily collect measurements in synchrony. For each sensor, the system models a 6-DOF pose relative to the workspace. When multiple sensors detect the same tag at the same instant in time, the spatial relationship between those sensors is recovered and used to update the workspace model. Because only relative spatial information is measured by the sensors, the model's origin is anchored to either a particular sensor, or to a tag having a known fixed pose relative to the physical workspace.

Embodiments include a pose detection algorithm for smooth pose detection and tracking of tags in an environment where sensors produce divergent, noisy, and occasionally incorrect pose hypotheses. The pose detection algorithm of an embodiment addresses two conditions present in practical systems.

The first condition is encountered when pose hypotheses from multiple sensors disagree. This first condition can result from imperfections in the workspace, sensor, and/or tag models. In practical applications, lower system cost may be traded for poorer data quality, wherein fewer, noisier, and slower-updating sensors may be used to cover a given workspace. Furthermore, the system's fast adaptation to workspace configuration changes implies that less information is available at any given instant for constructing and refining the workspace model.

The second condition is encountered when a single sensor produces multiple pose hypotheses for a single tag, and may arise from inherent sensor characteristics or spurious tag detections. For example, there is inherent ambiguity in a particular optical system observing a planar tag: two distinct hypotheses may fit equally well to a given measurement even with slight measurement noise. Additionally, sensor noise may directly produce spurious tag detections and hypotheses. It may be impossible to distinguish a correct hypothesis form an incorrect one based on a single measurement from a single sensor.

The system of an embodiment uses two methods to determine which of the pose hypotheses from a single sensor is correct. When a tag has been tracked with high confidence for multiple time steps, consistency between the last known good pose of a tag and a new hypothesis is a good metric for culling outlier hypotheses. When multiple sensors detect the same tag, the system culls hypotheses that are inconsistent across the sensors. Finally, if neither condition is true, all hypotheses are propagated to subsequent time steps until sufficient evidence has been collected to cull outliers.

In the case where a fixed set of sensors consistently detects and measures the pose of a particular tag at each time step, averaging the hypotheses approximates the maximum likelihood estimate for the tag's true pose given the available information. This quantity is referred to as the "average hypothesis" for a particular tag at a particular time step. The equation for the positional part of the average hypothesis is:

$$x_{avg}(t_n) = \frac{1}{m}[x_1(t_n) + x_2(t_n) + \ldots + x_m(t_n)] \quad (1.1)$$

where $t_n$ is the time step at which the hypotheses $x_i \in \mathbb{R}^2$ are measured, and m is the number of sensors detecting the tag at that instant. The rotational part of the average hypothesis can be approximated via similarly averaging, then re-normalizing, the unit direction vectors forming the basis of the tag's rotating coordinate frame within the workspace.

When a new sensor detects a tag or when an existing sensor stops detecting a tag, there is a discontinuity in the average hypothesis from one time step to the next. To mitigate this discontinuity, an embodiment introduces a correction factor to the previous equation, the result of which is referred to as the "smoothed hypothesis" for a particular time step. The positional part of the smoothed hypothesis is given by:

$$x_{sm}(t_n, t_{n-1}) = \qquad (1.2)$$
$$\frac{1}{m}[x_1(t_n) + c_1(t_{n-1}) + x_2(t_n) + c_2(t_{n-1}) + \ldots + x_m(t_n) + c_m(t_{n-1})]$$

and each correction factor is a vector defined as:

$$c_i(t_n, t_{n-1}) = k(x_{avg}(t_n) - x_i(t_n)) + (1-k)(x_{gm}(t_{n-1}) - x_i(t_{n-1})) \quad (1.3)$$

where k is a constant chosen between 0 and 1. The rotational part of the smoothed hypothesis can be computed via the application of (1.2) and (1.3) to the unit direction vectors forming the basis of the tag's rotating coordinate frame within the workspace, followed by re-normalization.

An embodiment uses k<<1 such that the corrected hypothesis $x_i + c_i$ is close to the smoothed hypothesis from the previous time step. Additionally, the choice of k>0, ensures that the smoothed hypothesis is forced towards the average hypothesis in each time step. Finally, k is varied such that when the motion of the tag is large between time steps (i.e. the user is performing large, fast motions), the smoothed hypothesis is more spatially accurate. Conversely, when the motion of the tag is small between time steps (i.e. the user is performing fine manipulations), k is chosen to be small such that the smoothed hypothesis maintains greater spatial and temporal smoothness. By appropriately choosing k, an embodiment maintains the flexibility to ensure high precision when the user is performing fine manipulations such as pointing, while enforcing overall accuracy when the user performs coarse motions such as dragging or gesturing.

Thus, the system of an embodiment uses imperfect data from sensors to track the full pose of tags within the workspace while eliminating false hypotheses and performing smoothing of discontinuities in pose estimates.

The system of an embodiment models a 6-DOF pose and the physical size of each screen. The system includes four methods for measuring screen poses including, but not limited to, permanent sensor(s) affixed to the screen bezel or surface, permanent tag(s) affixed to the screen bezel or surface, marking the screen by direct contact with a tagged object, and marking the screen from a distance using a pointing device.

When measuring screen poses using the permanent sensor(s) affixed to the screen bezel or surface, or the permanent tag(s) affixed to the screen bezel or surface, the system measures screen poses in real time within the workspace, and adapts to changes in screen pose automatically during system use. In this case, one or more tags, or one or more sensors are affixed to the periphery of a screen's surface in known locations. An embodiment of the system may use specially manufactured screen bezels with sensor or tag mount points whose measurements are known from blueprint specifications. In an alternative embodiment, manual measurements taken with a long ruler or a tape measure can be entered into the system by the user. Screen size may be measured manually and entered into the system, or it can be measured automatically by the system in an embodiment where two tags or two sensors are placed on opposite corners of the screen bezel. Because the system measures the poses of sensors and tags within the workspace, affixing either of these objects to screens facilitates direct measurement of screen poses. Using these methods, the system adapts its model to changes in the workspace configuration in real-time.

When measuring screen poses by marking the screen through direct contact with a tagged object, the user is prompted to mark each screen in the workspace in succession during a short configuration phase. First, the user is prompted to select a tagged object, which may be a glove, or pointing device such as a wand, or indeed, any other tagged object. Then, the user is prompted to place the object in direct contact with a pre-determined corner (e.g. top left) of the first screen, and then acknowledge the prompt (e.g. with a button click on the pointing device, or a gesture with the opposite hand). In this manner, each successive corner, and each successive screen is marked by the user. Because the system measures the poses of the tagged object relative to the workspace, and the corners of all screens have been directly marked using the tagged object, the system knows the sizes and poses of all screens within the workspace. Therefore, under this embodiment the corners of all screens must be within the sensing volume, and the system will not automatically adapt to changes in screen pose.

When measuring screen poses by marking the screen from a distance using a pointing device, the user is prompted to mark each screen in the workspace in succession during a short configuration phase. First, the user is prompted to select a pointing device such as a glove or wand. Then, the user is prompted to point with the device at a pre-determined corner (e.g. top left) of the first screen, and then acknowledge the prompt (e.g. with a button click on the pointing device, or a gesture with the opposite hand). The remaining three corners of the first screen are marked similarly, in succession. Finally, the user is prompted to enter the screen's width and height, or diagonal and aspect ratio into the system. Additional screens are marked similarly and in succession. In this embodiment, the system will not automatically adapt to changes in screen pose.

An example embodiment of the motion tracking system is described below which uses optical tags and individual cameras as sensors. Each tag comprises several optical fiducials called markers, where each marker comprises a single optical feature that is easily detected and localized in an image from a camera. There are no other restrictions on markers, and as a result, a variety of marker types may be used. For an infrared (IR) camera system, suitable markers may be IR LEDs or small dots of retro-reflective material; for a visible light camera system, a marker may simply be an easily-distinguishable color or intensity pattern.

In an embodiment, tags are configured such that each projective view of a tag conveys three pieces of information that include labeling, identity, and pose, but the embodiment is not so limited. Given a tag definition and a projective image of the same tag, the labeling relates points in the image to their corresponding markers in the tag. Given a set of many possible tags, the tag's identity defines which (if any) tag it is of the set. Finally, the pose of the tag is 3-DOF translation and 3-DOF rotation that relates the tag's position and orientation to that of the workspace.

The tag configuration of an embodiment takes advantage of an invariant of the projective transform called the cross ratio (Heartley & Zisserman 2008, p. 45). Given a set of four collinear points a, b, c, d$\in \mathbb{R}^2$ their cross ratio is a function of the pair-wise distances between the points:

$$\text{Cross}(a, b, c, d) = \frac{|a-b||c-d|}{|a-c||b-d|} \quad (1.4)$$

The system of an embodiment comprises a linear-partial-tag (LPT) that is a tag comprising four collinear markers. The LPTs can be labeled and identified from a single image by searching that image for sets of four collinear points, and matching their cross ratio to that of a known tag. Because the markers in an LPT are collinear, only a 5-DOF pose may be determined for a single LPT. Therefore, an embodiment defines a full tag in the context of the system to be two parallel LPTs attached to a planar surface, allowing for recovery of labeling, identity, and full 6-DOF pose data for an 8-marker tag.

Figure 1C:
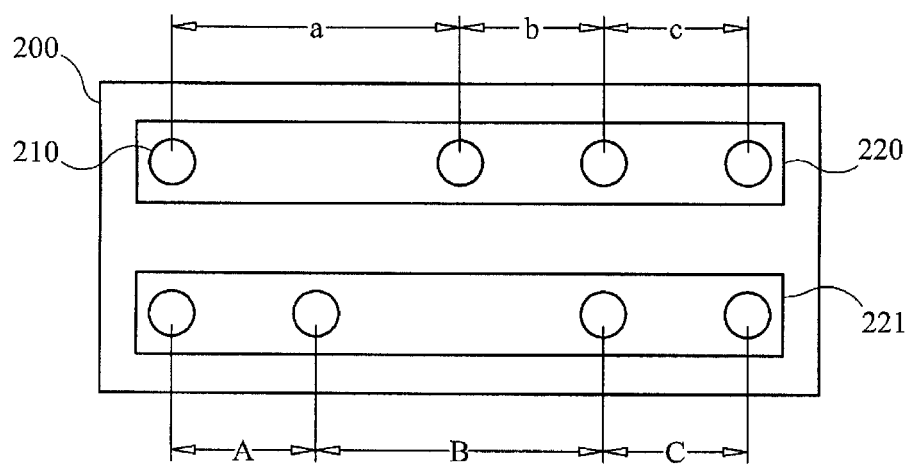
FIG. 1C shows an 8-marker tag comprising two parallel LPTs, under an embodiment.

A benefit of using multiple LPTs to make up a single tag is that relatively few unique LPTs can be combined to form many unique 8-marker tags. As an example, FIG. 1C shows an 8-marker tag 200 comprising two parallel LPTs 220 and 221, under an embodiment. Each LPT 220 and 221 of this example comprises four (4) optical markers 210, but the LPTs are not limited to any particular number of optical markers. The distances a, b, c between the optical markers 210 of LPT 220, and the distances A, B, C between the optical markers 210 of LPT 221, form two distinct cross ratios, making LPTs 220 and 221 identifiable, distinguishable, and localizable from a projective view of the tag.

Since projection preserves the straightness of lines, sets of collinear markers may be found from a single image. An embodiment fits a straight line to each candidate set of four markers using a two-dimensional (2D) line fitting algorithm based on Eigen-decomposition (Schomaker et al. 1957), although other methods could be used as well.

Once the aforementioned candidate sets of collinear markers are found or identified, their cross ratio is computed according to (1.4), and the computed cross ratio is then compared against the cross ratios of known LPTs. Because physical hardware does not produce perfect, noise-free data, candidate cross ratio matches will generally not be exact. However, an embodiment selects a confidence metric for accepting such inexact candidate matches.

Finally, an embodiment combines LPTs into candidate tags, estimates their poses, and discriminates between pose hypotheses using a confidence metric. The image is searched for nearby and nearly parallel LPTs to combine into tag candidates. For each candidate tag, a set of 6-DOF pose hypotheses is computed from a single projective view. The system of an embodiment makes no restriction as to which of the methods may be used to compute the pose hypotheses (e.g. Kabsch 1978), (Alter 1994), (DeMenthon & Davis 1995)). An embodiment computes the re-projection error (which is similar to a sample variance) of a particular tag's pose in a particular view for use as a confidence metric:

$$E_r = \frac{1}{p}\sum_{i=1}^{p}(u_i - C(P \cdot x_i))^2 \quad (1.5)$$

where p is the number of markers in a tag, $u_i \in \mathbb{R}^2$ is the measured pixel position of a marker in the image, $x_i \in \mathbb{R}^3$ is the corresponding ideal position (in homogeneous coordinates) of that marker in the tag's coordinate frame, P is a 4×4 matrix representing the tag's pose, and $C: \mathbb{R}^3 \rightarrow \mathbb{R}^2$ is the camera model. The pose hypotheses, along with their confidence metrics, are then passed to the motion tracking pipeline described herein and in the Related Applications.

The optical system of an embodiment inherently collects correspondences between tag markers and image coordinates during use. This data forms the input for single-camera calibration algorithms (e.g. (Zhang 1999), (Bradski & Kaehler 2008, p. 378)). Such single-camera calibration algorithms can be used to model camera intrinsic parameters such as focal ratios, optical center, skewness, lens distortions, and others. While the use of high-quality empirical camera models is not a necessary component of the optical motion tracking system, its use can improve tracking quality and spatial consistency of the system in general. In one embodiment, the abstract workspace model described above is extended to also store and update estimates for camera intrinsic parameters at each time step.

A traditional pointing device such as a mouse provides more than just a floating cursor in that it generally has buttons and a scroll wheel. Similarly, the 3D pointing devices of an embodiment may convey button-click, scroll, and other state information, including but not limited to inertial measurements, back to the user's system.

For example, a button-click on a pointing wand causes the geometric configuration of the wand's optical tags to change. The optical system detects this tag change as a "button pressed" event, updating the wand's cursor appearance and behavior appropriately. In one embodiment, a wand is adorned with tags comprising retro-reflective markers and an optical system with IR strobes is used for sensing; when a button is pressed, additional active IR LED markers are illuminated within the wand's tags, changing the tags' optical signature. In a similar embodiment, each tag comprises active IR LED markers, some of which are illuminated while some are inactive; when a button on the wand is pressed, several of the LED markers change state (from illuminated to inactive, or vice versa) changing the optical signature of the tag. In another embodiment, the wand's state is conveyed to the user's system via an IR transceiver system similar to that used for IR headphones. In still another embodiment, the wand's state is conveyed to the user's system via a radio system similar to that used for cordless phones or wireless networking. An example wand also referred to herein as a multi-modal input device (MMID), allows the user of a spatial or gestural input system to access a range of input functionalities intuitively and in an ergonomically efficient manner. The MMID of an embodiment is a hand-held input device, as described in detail herein.

Figure 1D:
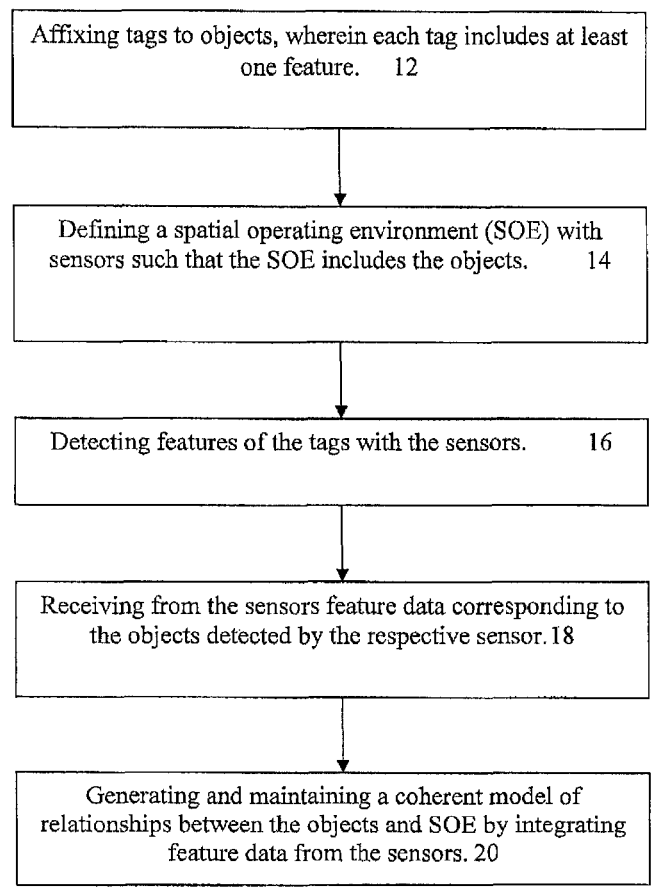
FIG. 1D is a flow diagram of the real-time tracking, under an embodiment.

FIG. 1D is a flow diagram of the real-time tracking 10, under an embodiment. Generally, embodiments described herein provide real-time tracking of spatial input devices by affixing tags to one or more objects in a SOE, where the tags each include at least one feature 12. Embodiments equip the SOE with one or more sensors such that a location of the sensors defines the SOE to include the objects 14. Embodiments detect the tags with the sensors 16, and receive from each sensor feature data corresponding to each object in the SOE detected by the respective sensor 18. Embodiments integrate the feature data from the sensors to generate and maintain a coherent model of relationships between the objects and the SOE 20.

As another alternative to a system operating with tagged objects (e.g., gloves, wands, etc.) described herein, embodiments of the SOE include systems and methods for real-time, vision-based hand tracking. An example of one such system is described in detail in the Related Applications referenced herein. These alternative embodiments combine fast fingertip detection with robust local hand tracking and in so doing detect, identify, track, and/or localize the position of one or more user's hands using captured gesture data. For example, hand tracking as described in particular embodiments herein includes the process of detecting and localizing the position of one or more user's hands in consecutive frames of a video stream. In the context of the SOE or other gestural interface, such tracking is used to determine when the user is trying to communicate with the system, to provide basic information needed for detecting and recognizing temporally extended gestures, and to allow for real-time control and feedback for interactions such as pointing, dragging, selecting, and other direct manipulations, to name a few.

The following references include additional information relating to tracking systems.

Alter T D. 3-D Pose from 3 Points Using Weak-Perspective. IEEE Trans. Pattern Anal. Mach. Intell., 1994: 802~808.

Bradski G, Kaehler A. Learning OpenCV: Computer Vision with the OpenCV Library. $1^{st}$ Ed. O'Reilly Media, Inc. 2008.

DeMenthon D, Davis L S. Model-Based Object Pose in 25 Lines of Code. International Journal of Computer Vision, 15, pp. 123-141. June 1995.

Hartley R, Zisserman A. Multiple View Geometry in Computer Vision. $2^{nd}$ Ed. Cambridge University Press. 2008.

Kabsch W. A solution of the best rotation to relate two sets of vectors. *Acta Crystallographica* (1976), 32:922.

Kabsch W. A discussion of the solution for the best rotation to relate two sets of vectors. *Acta Crystallographica* (1978). A34, 827-828.

Schomaker V, Waser J, Marsh R E, Bergman G. To fit a plane or a line to a set of points by least squares. *Acta Crystallographica* (1959). 12, 600-604.

Underkoffler J S, Parent K T, Kramer K H. System and method for gesture based control system. U.S. Pat. No. 7,598,942, issued Oct. 6, 2009.

Zhang Z. Flexible Camera Calibration by Viewing a Plane from Unknown Orientations. International Conference on Computer Vision (ICCV'99), Corfu, Greece, pages 666-673, September 1999.

Spatial Operating Environment (SOE)

Embodiments of a spatial-continuum input system are described herein in the context of a Spatial Operating Environment (SOE), as generally described above. As an example, FIG. 1A is a block diagram of a Spatial Operating Environment (SOE), under an embodiment. Generally, a user locates his hands 101 and 102 in the viewing area 150 of an array of cameras 104A-104D. The cameras detect location, orientation, and movement of the fingers and hands 101 and 102, as spatial tracking data, and generate output signals to pre-processor 105. Pre-processor 105 translates the camera output into a gesture signal that is provided to the computer processing unit 107 of the system. The computer 107 uses the input information to generate a command to control one or more on screen cursors and provides video output to display 103. The systems and methods described in detail above for initializing real-time, vision-based hand tracking systems can be used in the SOE and in analogous systems, for example.

Although the system is shown with a single user's hands as input, the SOE 100 may be implemented using multiple users. In addition, instead of or in addition to hands, the system may track any part or parts of a user's body, including head, feet, legs, arms, elbows, knees, and the like.

In the embodiment shown, four cameras or sensors are used to detect the location, orientation, and movement of the user's hands 101 and 102 in the viewing area 150. It should be understood that the SOE 100 may include more (e.g., six cameras, eight cameras, etc.) or fewer (e.g., two cameras) cameras or sensors without departing from the scope or spirit of the SOE. In addition, although the cameras or sensors are disposed symmetrically in the example embodiment, there is no requirement of such symmetry in the SOE 100. Any number or positioning of cameras or sensors that permits the location, orientation, and movement of the user's hands may be used in the SOE 100.

In one embodiment, the cameras used are motion capture cameras capable of capturing grey-scale images. In one embodiment, the cameras used are those manufactured by Vicon, such as the Vicon MX40 camera. This camera includes on-camera processing and is capable of image capture at 1000 frames per second. A motion capture camera is capable of detecting and locating markers.

In the embodiment described, the cameras are sensors used for optical detection. In other embodiments, the cameras or other detectors may be used for electromagnetic, magnetostatic, RFID, or any other suitable type of detection.

Pre-processor 105 generates three dimensional space point reconstruction and skeletal point labeling. The gesture translator 106 converts the 3D spatial information and marker motion information into a command language that can be interpreted by a computer processor to update the location, shape, and action of a cursor on a display. In an alternate embodiment of the SOE 100, the pre-processor 105 and gesture translator 106 are integrated or combined into a single device.

Computer 107 may be any general purpose computer such as manufactured by Apple, Dell, or any other suitable manufacturer. The computer 107 runs applications and provides display output. Cursor information that would otherwise come from a mouse or other prior art input device now comes from the gesture system.

Marker Tags

The SOE or an embodiment contemplates the use of marker tags on one or more fingers of the user so that the system can locate the hands of the user, identify whether it is viewing a left or right hand, and which fingers are visible. This permits the system to detect the location, orientation, and movement of the user's hands. This information allows a number of gestures to be recognized by the system and used as commands by the user.

The marker tags in one embodiment are physical tags comprising a substrate (appropriate in the present embodiment for affixing to various locations on a human hand) and discrete markers arranged on the substrate's surface in unique identifying patterns.

The markers and the associated external sensing system may operate in any domain (optical, electromagnetic, magnetostatic, etc.) that allows the accurate, precise, and rapid and continuous acquisition of their three-space position. The markers themselves may operate either actively (e.g. by emitting structured electromagnetic pulses) or passively (e.g. by being optically retroreflective, as in the present embodiment).

At each frame of acquisition, the detection system receives the aggregate 'cloud' of recovered three-space locations comprising all markers from tags presently in the instrumented workspace volume (within the visible range of the cameras or other detectors). The markers on each tag are of sufficient multiplicity and are arranged in unique patterns such that the detection system can perform the following tasks: (1) segmentation, in which each recovered marker position is assigned to one and only one subcollection of points that form a single tag; (2) labelling, in which each segmented subcollection of points is identified as a particular tag; (3) location, in which the three-space position of the identified tag is recovered; and (4) orientation, in which the three-space orientation of the identified tag is recovered. Tasks (1) and (2) are made possible through the specific nature of the marker-patterns, as described below and as illustrated in one embodiment in FIG. 2.

The markers on the tags in one embodiment are affixed at a subset of regular grid locations. This underlying grid may, as in the present embodiment, be of the traditional Cartesian sort; or may instead be some other regular plane tessellation (a triangular/hexagonal tiling arrangement, for example). The scale and spacing of the grid is established with respect to the known spatial resolution of the marker-sensing system, so that adjacent grid locations are not likely to be confused. Selection of marker patterns for all tags should satisfy the following constraint: no tag's pattern shall coincide with that of any other tag's pattern through any combination of rotation, translation, or mirroring. The multiplicity and arrangement of markers may further be chosen so that loss (or occlusion) of some specified number of component markers is tolerated: After any arbitrary transformation, it should still be unlikely to confuse the compromised module with any other.

Figure 2:
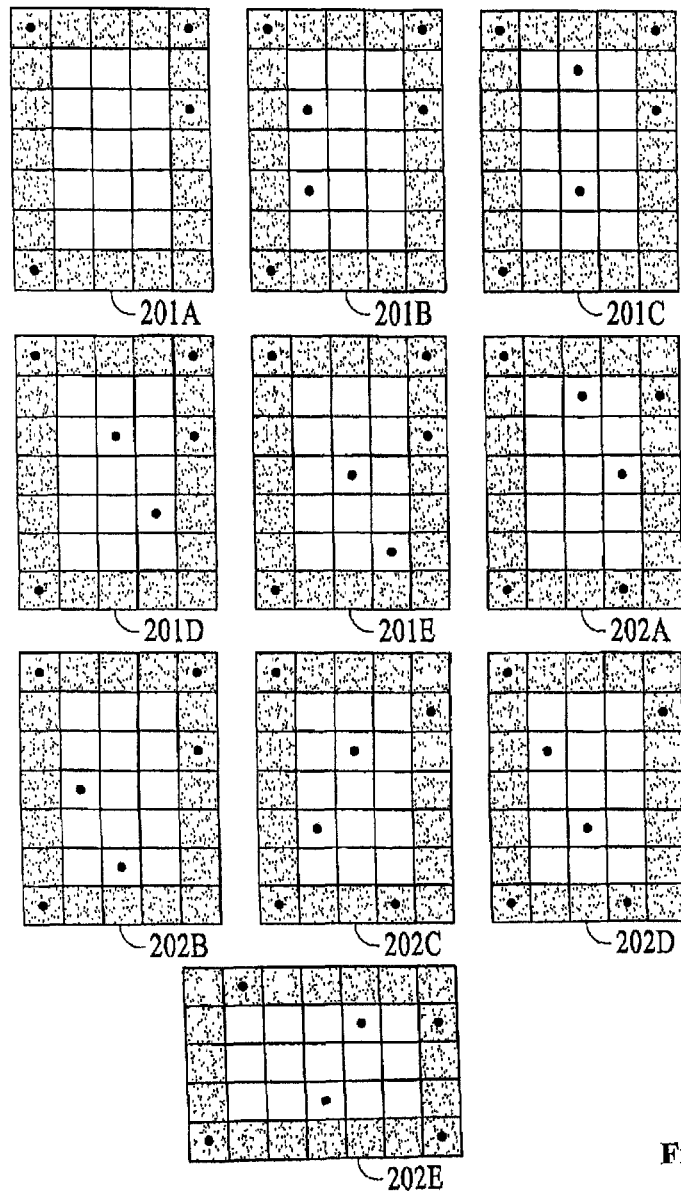
FIG. 2 is a diagram of marking tags, under an embodiment.

Referring now to FIG. 2, a number of tags 201A-201E (left hand) and 202A-202E (right hand) are shown. Each tag is rectangular and consists in this embodiment of a 5×7 grid array. The rectangular shape is chosen as an aid in determining orientation of the tag and to reduce the likelihood of mirror duplicates. In the embodiment shown, there are tags for each finger on each hand. In some embodiments, it may be adequate to use one, two, three, or four tags per hand. Each tag has a border of a different grey-scale or color shade. Within this border is a 3×5 grid array. Markers (represented by the black dots of FIG. 7) are disposed at certain points in the grid array to provide information.

Qualifying information may be encoded in the tags' marker patterns through segmentation of each pattern into 'common' and 'unique' subpatterns. For example, the present embodiment specifies two possible 'border patterns', distributions of markers about a rectangular boundary. A 'family' of tags is thus established—the tags intended for the left hand might thus all use the same border pattern as shown in tags 201A-201E while those attached to the right hand's fingers could be assigned a different pattern as shown in tags 202A-202E. This subpattern is chosen so that in all orientations of the tags, the left pattern can be distinguished from the right pattern. In the example illustrated, the left hand pattern includes a marker in each corner and on marker in a second from corner grid location. The right hand pattern has markers in only two corners and two markers in non corner grid locations. An inspection of the pattern reveals that as long as any three of the four markers are visible, the left hand pattern can be positively distinguished from the left hand pattern. In one embodiment, the color or shade of the border can also be used as an indicator of handedness.

Each tag must of course still employ a unique interior pattern, the markers distributed within its family's common border. In the embodiment shown, it has been found that two markers in the interior grid array are sufficient to uniquely identify each of the ten fingers with no duplication due to rotation or orientation of the fingers. Even if one of the markers is occluded, the combination of the pattern and the handedness of the tag yields a unique identifier.

In the present embodiment, the grid locations are visually present on the rigid substrate as an aid to the (manual) task of affixing each retroreflective marker at its intended location. These grids and the intended marker locations are literally printed via color inkjet printer onto the substrate, which here is a sheet of (initially) flexible 'shrink-film'. Each module is cut from the sheet and then oven-baked, during which thermal treatment each module undergoes a precise and repeatable shrinkage. For a brief interval following this procedure, the cooling tag may be shaped slightly—to follow the longitudinal curve of a finger, for example; thereafter, the substrate is suitably rigid, and markers may be affixed at the indicated grid points.

In one embodiment, the markers themselves are three dimensional, such as small reflective spheres affixed to the substrate via adhesive or some other appropriate means. The three-dimensionality of the markers can be an aid in detection and location over two dimensional markers. However either can be used without departing from the spirit and scope of the SOE described herein.

At present, tags are affixed via Velcro or other appropriate means to a glove worn by the operator or are alternately affixed directly to the operator's fingers using a mild double-stick tape. In a third embodiment, it is possible to dispense altogether with the rigid substrate and affix- or 'paint'- individual markers directly onto the operator's fingers and hands.

Gesture Vocabulary

The SOE of an embodiment contemplates a gesture vocabulary consisting of hand poses, orientation, hand combinations, and orientation blends. A notation language is also implemented for designing and communicating poses and gestures in the gesture vocabulary of the SOE. The gesture vocabulary is a system for representing instantaneous 'pose states' of kinematic linkages in compact textual form. The linkages in question may be biological (a human hand, for example; or an entire human body; or a grasshopper leg; or the articulated spine of a lemur) or may instead be nonbiological (e.g. a robotic arm). In any case, the linkage may be simple (the spine) or branching (the hand). The gesture vocabulary system of the SOE establishes for any specific linkage a constant length string; the aggregate of the specific ASCII characters occupying the string's 'character locations' is then a unique description of the instantaneous state, or 'pose', of the linkage.

Hand Poses

FIG. 3 illustrates hand poses in an embodiment of a gesture vocabulary of the SOE, under an embodiment. The SOE supposes that each of the five fingers on a hand is used. These fingers are codes as p-pinkie, r-ring finger, m-middle finger, i-index finger, and t-thumb. A number of poses for the fingers and thumbs are defined and illustrated in FIG. 8. A gesture vocabulary string establishes a single character position for each expressible degree of freedom in the linkage (in this case, a finger). Further, each such degree of freedom is understood to be discretized (or 'quantized'), so that its full range of motion can be expressed through assignment of one of a finite number of standard ASCII characters at that string position. These degrees of freedom are expressed with respect to a body-specific origin and coordinate system (the back of the hand, the center of the grasshopper's body; the base of the robotic arm; etc.). A small number of additional gesture vocabulary character positions are therefore used to express the position and orientation of the linkage 'as a whole' in the more global coordinate system.

Still referring to FIG. 8, a number of poses are defined and identified using ASCII characters. Some of the poses are divided between thumb and non-thumb. The SOE in this embodiment uses a coding such that the ASCII character itself is suggestive of the pose. However, any character may used to represent a pose, whether suggestive or not. In addition, there is no requirement in the embodiments to use ASCII characters for the notation strings. Any suitable symbol, numeral, or other representation maybe used without departing from the scope and spirit of the embodiments. For example, the notation may use two bits per finger if desired or some other number of bits as desired.

A curled finger is represented by the character "^" while a curled thumb by ">". A straight finger or thumb pointing up is indicated by "1" and at an angle by "\" or "/". "-" represents a thumb pointing straight sideways and "x" represents a thumb pointing into the plane.

Using these individual finger and thumb descriptions, a robust number of hand poses can be defined and written using the scheme of the embodiments. Each pose is represented by five characters with the order being p-r-m-i-t as described above. FIG. 8 illustrates a number of poses and a few are described here by way of illustration and example. The hand held flat and parallel to the ground is represented by "11111". A fist is represented by "^^^^>". An "OK" sign is represented by "111^>".

The character strings provide the opportunity for straightforward 'human readability' when using suggestive characters. The set of possible characters that describe each degree of freedom may generally be chosen with an eye to quick recognition and evident analogy. For example, a vertical bar ('|') would likely mean that a linkage element is 'straight', an ell ('L') might mean a ninety-degree bend, and a circumflex ('^') could indicate a sharp bend. As noted above, any characters or coding may be used as desired.

Any system employing gesture vocabulary strings such as described herein enjoys the benefit of the high computational efficiency of string comparison—identification of or search for any specified pose literally becomes a 'string compare' (e.g. UNIX's 'strcmp( )' function) between the desired pose string and the instantaneous actual string. Furthermore, the use of 'wildcard characters' provides the programmer or system designer with additional familiar efficiency and efficacy: degrees of freedom whose instantaneous state is irrelevant for a match may be specified as an interrogation point ('?'); additional wildcard meanings may be assigned.

Orientation

In addition to the pose of the fingers and thumb, the orientation of the hand can represent information. Characters describing global-space orientations can also be chosen transparently: the characters '<', '>', '^', and 'v' may be used to indicate, when encountered in an orientation character position, the ideas of left, right, up, and down. FIG. 4 illustrates hand orientation descriptors and examples of coding that combines pose and orientation. In an embodiment, two character positions specify first the direction of the palm and then the direction of the fingers (if they were straight, irrespective of the fingers' actual bends). The possible characters for these two positions express a 'body-centric' notion of orientation: '-', '+', 'x', '*', '^', and 'v' describe medial, lateral, anterior (forward, away from body), posterior (backward, away from body), cranial (upward), and caudal (downward).

In the notation scheme of an embodiment, the five finger pose indicating characters are followed by a colon and then two orientation characters to define a complete command pose. In one embodiment, a start position is referred to as an "xyz" pose where the thumb is pointing straight up, the index finger is pointing forward and the middle finger is perpendicular to the index finger, pointing to the left when the pose is made with the right hand. This is represented by the string "^^x1-:-x".

'XYZ-hand' is a technique for exploiting the geometry of the human hand to allow full six-degree-of-freedom navigation of visually presented three-dimensional structure. Although the technique depends only on the bulk translation and rotation of the operator's hand—so that its fingers may in principal be held in any pose desired—the present embodiment prefers a static configuration in which the index finger points away from the body; the thumb points toward the ceiling; and the middle finger points left-right. The three fingers thus describe (roughly, but with clearly evident intent) the three mutually orthogonal axes of a three-space coordinate system: thus 'XYZ-hand'.

XYZ-hand navigation then proceeds with the hand, fingers in a pose as described above, held before the operator's body at a predetermined 'neutral location'. Access to the three translational and three rotational degrees of freedom of a three-space object (or camera) is effected in the following natural way: left-right movement of the hand (with respect to the body's natural coordinate system) results in movement along the computational context's x-axis; up-down movement of the hand results in movement along the controlled context's y-axis; and forward-back hand movement (toward/away from the operator's body) results in z-axis motion within the context. Similarly, rotation of the operator's hand about the index finger leads to a 'roll' change of the computational context's orientation; 'pitch' and 'yaw' changes are effected analogously, through rotation of the operator's hand about the middle finger and thumb, respectively.

Note that while 'computational context' is used here to refer to the entity being controlled by the XYZ-hand method—and seems to suggest either a synthetic three-space object or camera—it should be understood that the technique is equally useful for controlling the various degrees of freedom of real-world objects: the pan/tilt/roll controls of a video or motion picture camera equipped with appropriate rotational actuators, for example. Further, the physical degrees of freedom afforded by the XYZ-hand posture may be somewhat less literally mapped even in a virtual domain: In the present embodiment, the XYZ-hand is also used to provide navigational access to large panoramic display images, so that left-right and up-down motions of the operator's hand lead to the expected left-right or up-down 'panning' about the image, but forward-back motion of the operator's hand maps to 'zooming' control.

In every case, coupling between the motion of the hand and the induced computational translation/rotation may be either direct (i.e. a positional or rotational offset of the operator's hand maps one-to-one, via some linear or non-linear function, to a positional or rotational offset of the object or camera in the computational context) or indirect (i.e. positional or rotational offset of the operator's hand maps one-to-one, via some linear or nonlinear function, to a first or higher-degree derivative of position/orientation in the computational context; ongoing integration then effects a non-static change in the computational context's actual zero-order position/orientation). This latter means of control is analogous to use of a an automobile's 'gas pedal', in which a constant offset of the pedal leads, more or less, to a constant vehicle speed.

The 'neutral location' that serves as the real-world XYZ-hand's local six-degree-of-freedom coordinate origin may be established (1) as an absolute position and orientation in space (relative, say, to the enclosing room); (2) as a fixed position and orientation relative to the operator herself (e.g. eight inches in front of the body, ten inches below the chin, and laterally in line with the shoulder plane), irrespective of the overall position and 'heading' of the operator; or (3) interactively, through deliberate secondary action of the operator (using, for example, a gestural command enacted by the operator's 'other' hand, said command indicating that the XYZ-hand's present position and orientation should henceforth be used as the translational and rotational origin).

It is further convenient to provide a 'detent' region (or 'dead zone') about the XYZ-hand's neutral location, such that movements within this volume do not map to movements in the controlled context.

Other poses may include:

[||||:vx] is a flat hand (thumb parallel to fingers) with palm facing down and fingers forward.

[||||:x^] is a flat hand with palm facing forward and fingers toward ceiling.

[||||:-x] is a flat hand with palm facing toward the center of the body (right if left hand, left if right hand) and fingers forward.

[^^^^-:-x] is a single-hand thumbs-up (with thumb pointing toward ceiling).

[^^^|:-x] is a mime gun pointing forward.

Two Hand Combination

The SOE of an embodiment contemplates single hand commands and poses, as well as two-handed commands and poses. FIG. 5 illustrates examples of two hand combinations and associated notation in an embodiment of the SOE. Reviewing the notation of the first example, "full stop" reveals that it comprises two closed fists. The "snapshot" example has the thumb and index finger of each hand extended, thumbs pointing toward each other, defining a goal post shaped frame. The "rudder and throttle start position" is fingers and thumbs pointing up palms facing the screen.

Orientation Blends

Figure 6:
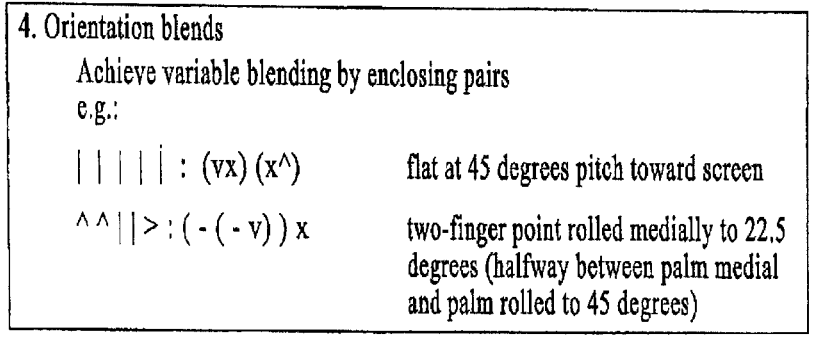
FIG. 6 is a diagram of orientation blends in a gesture vocabulary, under an embodiment.

FIG. 6 illustrates an example of an orientation blend in an embodiment of the SOE. In the example shown the blend is represented by enclosing pairs of orientation notations in parentheses after the finger pose string. For example, the first command shows finger positions of all pointing straight. The first pair of orientation commands would result in the palms being flat toward the display and the second pair has the hands rotating to a 45 degree pitch toward the screen. Although pairs of blends are shown in this example, any number of blends is contemplated in the SOE.

Example Commands

FIGS. 8A and 8B show a number of possible commands that may be used with the SOE. Although some of the discussion here has been about controlling a cursor on a display, the SOE is not limited to that activity. In fact, the SOE has great application in manipulating any and all data and portions of data on a screen, as well as the state of the display. For example, the commands may be used to take the place of video controls during play back of video media. The commands may be used to pause, fast forward, rewind, and the like. In addition, commands may be implemented to zoom in or zoom out of an image, to change the orientation of an image, to pan in any direction, and the like. The SOE may also be used in lieu of menu commands such as open, close, save, and the like. In other words, any commands or activity that can be imagined can be implemented with hand gestures.

Operation

Figure 7:
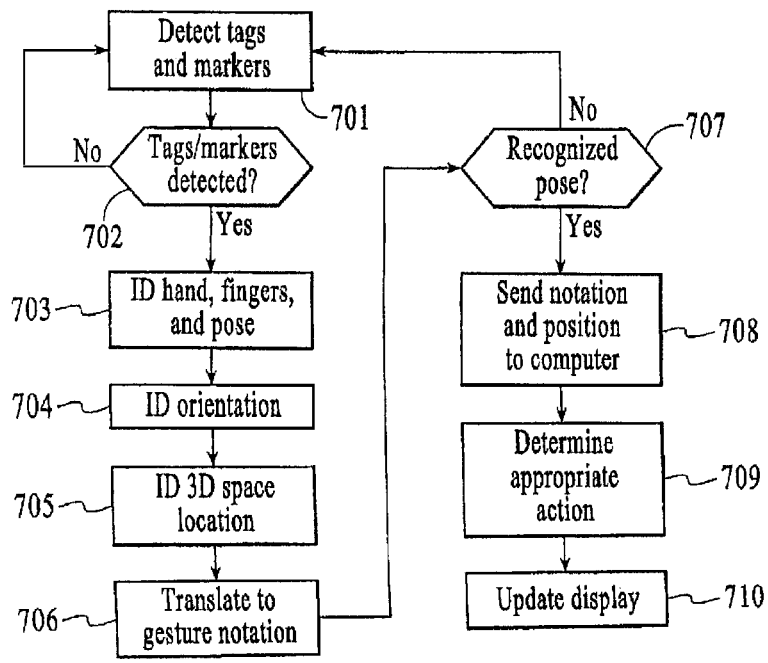
FIG. 7 is a flow diagram of system operation, under an embodiment.

FIG. 7 is a flow diagram illustrating the operation of the SOE in one embodiment. At 701 the detection system detects the markers and tags. At 702 it is determined if the tags and markers are detected. If not, the system returns to 701. If the tags and markers are detected at 702, the system proceeds to 703. At 703 the system identifies the hand, fingers and pose from the detected tags and markers. At 704 the system identifies the orientation of the pose. At 705 the system identifies the three dimensional spatial location of the hand or hands that are detected. (Please note that any or all of 703, 704, and 705 may be combined).

At 706 the information is translated to the gesture notation described above. At 707 it is determined if the pose is valid. This may be accomplished via a simple string comparison using the generated notation string. If the pose is not valid, the system returns to 701. If the pose is valid, the system sends the notation and position information to the computer at 708. At 709 the computer determines the appropriate action to take in response to the gesture and updates the display accordingly at 710.

In one embodiment of the SOE, 701-705 are accomplished by the on-camera processor. In other embodiments, the processing can be accomplished by the system computer if desired.

Parsing and Translation

The system is able to "parse" and "translate" a stream of low-level gestures recovered by an underlying system, and turn those parsed and translated gestures into a stream of command or event data that can be used to control a broad range of computer applications and systems. These techniques and algorithms may be embodied in a system consisting of computer code that provides both an engine implementing these techniques and a platform for building computer applications that make use of the engine's capabilities.

One embodiment is focused on enabling rich gestural use of human hands in computer interfaces, but is also able to recognize gestures made by other body parts (including, but not limited to arms, torso, legs and the head), as well as non-hand physical tools of various kinds, both static and articulating, including but not limited to calipers, compasses, flexible curve approximators, and pointing devices of various shapes. The markers and tags may be applied to items and tools that may be carried and used by the operator as desired.

The system described here incorporates a number of innovations that make it possible to build gestural systems that are rich in the range of gestures that can be recognized and acted upon, while at the same time providing for easy integration into applications.

The gestural parsing and translation system in one embodiment comprises:

1) a compact and efficient way to specify (encode for use in computer programs) gestures at several different levels of aggregation:

a. a single hand's "pose" (the configuration and orientation of the parts of the hand relative to one another) a single hand's orientation and position in three-dimensional space.

b. two-handed combinations, for either hand taking into account pose, position or both.

c. multi-person combinations; the system can track more than two hands, and so more than one person can cooperatively (or competitively, in the case of game applications) control the target system.

d. sequential gestures in which poses are combined in a series; we call these "animating" gestures.

e. "grapheme" gestures, in which the operator traces shapes in space.

2) a programmatic technique for registering specific gestures from each category above that are relevant to a given application context.

3) algorithms for parsing the gesture stream so that registered gestures can be identified and events encapsulating those gestures can be delivered to relevant application contexts.

The specification system (1), with constituent elements (1a) to (1f), provides the basis for making use of the gestural parsing and translating capabilities of the system described here.

A single-hand "pose" is represented as a string of i) relative orientations between the fingers and the back of the hand, ii) quantized into a small number of discrete states.

Using relative joint orientations allows the system described here to avoid problems associated with differing hand sizes and geometries. No "operator calibration" is required with this system. In addition, specifying poses as a string or collection of relative orientations allows more complex gesture specifications to be easily created by combining pose representations with further filters and specifications.

Using a small number of discrete states for pose specification makes it possible to specify poses compactly as well as to ensure accurate pose recognition using a variety of underlying tracking technologies (for example, passive optical tracking using cameras, active optical tracking using lighted dots and cameras, electromagnetic field tracking, etc).

Gestures in every category (1a) to (1f) may be partially (or minimally) specified, so that non-critical data is ignored. For example, a gesture in which the position of two fingers is definitive, and other finger positions are unimportant, may be represented by a single specification in which the operative positions of the two relevant fingers is given and, within the same string, "wild cards" or generic "ignore these" indicators are listed for the other fingers.

All of the innovations described here for gesture recognition, including but not limited to the multi-layered specification technique, use of relative orientations, quantization of data, and allowance for partial or minimal specification at every level, generalize beyond specification of hand gestures to specification of gestures using other body parts and "manufactured" tools and objects.

The programmatic techniques for "registering gestures" (2), consist of a defined set of Application Programming Interface calls that allow a programmer to define which gestures the engine should make available to other parts of the running system.

These API routines may be used at application set-up time, creating a static interface definition that is used throughout the lifetime of the running application. They may also be used during the course of the run, allowing the interface characteristics to change on the fly. This real-time alteration of the interface makes it possible to, i) build complex contextual and conditional control states,
ii) to dynamically add hysteresis to the control environment, and
iii) to create applications in which the user is able to alter or extend the interface vocabulary of the running system itself.

Algorithms for parsing the gesture stream (3) compare gestures specified as in (1) and registered as in (2) against incoming low-level gesture data. When a match for a registered gesture is recognized, event data representing the matched gesture is delivered up the stack to running applications.

Efficient real-time matching is desired in the design of this system, and specified gestures are treated as a tree of possibilities that are processed as quickly as possible.

In addition, the primitive comparison operators used internally to recognize specified gestures are also exposed for the applications programmer to use, so that further comparison (flexible state inspection in complex or compound gestures, for example) can happen even from within application contexts.

Recognition "locking" semantics are an innovation of the system described here. These semantics are implied by the registration API (2) (and, to a lesser extent, embedded within the specification vocabulary (1)). Registration API calls include,
i) "entry" state notifiers and "continuation" state notifiers, and
ii) gesture priority specifiers.

If a gesture has been recognized, its "continuation" conditions take precedence over all "entry" conditions for gestures of the same or lower priorities. This distinction between entry and continuation states adds significantly to perceived system usability.

The system described here includes algorithms for robust operation in the face of real-world data error and uncertainty. Data from low-level tracking systems may be incomplete (for a variety of reasons, including occlusion of markers in optical tracking, network drop-out or processing lag, etc).

Missing data is marked by the parsing system, and interpolated into either "last known" or "most likely" states, depending on the amount and context of the missing data.

If data about a particular gesture component (for example, the orientation of a particular joint) is missing, but the "last known" state of that particular component can be analyzed as physically possible, the system uses this last known state in its real-time matching.

Conversely, if the last known state is analyzed as physically impossible, the system falls back to a "best guess range" for the component, and uses this synthetic data in its real-time matching.

The specification and parsing systems described here have been carefully designed to support "handedness agnosticism," so that for multi-hand gestures either hand is permitted to satisfy pose requirements.

Coincident Virtual/Display and Physical Spaces

As described above, the tracking system can provide an environment in which virtual space depicted on one or more display devices ("screens") is treated as coincident with the physical space inhabited by the operator or operators of the system. An embodiment of such an environment is described below that includes three projector-driven screens at fixed locations, is driven by a single desktop computer, and is controlled using the gestural vocabulary and interface system described herein, but the embodiment is not so limited. Note, however, that any number of screens are supported by the techniques being described, that those screens may be mobile (rather than fixed), that the screens may be driven by many independent computers simultaneously, and that the overall system can be controlled by any input device or technique.

The interface system described in this disclosure determines the dimensions, orientations and positions of screens in physical space. Given this information, the system is able to dynamically map the physical space in which these screens are located (and which the operators of the system inhabit) as a projection into the virtual space of computer applications running on the system. As part of this automatic mapping, the system also translates the scale, angles, depth, dimensions and other spatial characteristics of the two spaces in a variety of ways, according to the needs of the applications that are hosted by the system.

This continuous translation between physical and virtual space makes possible the consistent and pervasive use of a number of interface techniques that are difficult to achieve on existing application platforms or that must be implemented piece-meal for each application running on existing platforms. These techniques include (but are not limited to):
1) Use of "literal pointing"—using the hands in a gestural interface environment, or using physical pointing tools or devices—as a pervasive and natural interface technique.
2) Automatic compensation for movement or repositioning of screens.
3) Graphics rendering that changes depending on operator position, for example simulating parallax shifts to enhance depth perception.
4) Inclusion of physical objects in on-screen display—taking into account real-world position, orientation, state, etc. For example, an operator standing in front of a large, opaque screen, could see both applications graphics and a representation of the true position of a scale model that is behind the screen (and is, perhaps, moving or changing orientation).

It is important to note that literal pointing is different from the abstract pointing used in mouse-based windowing interfaces and most other contemporary systems. In those systems, the operator must learn to manage a translation between a virtual pointer and a physical pointing device, and must map between the two cognitively.

By contrast, in the systems described herein, there is no difference between virtual and physical space (except that virtual space is more amenable to mathematical manipulation), either from an application or user perspective, so there is no cognitive translation required of the operator.

The closest analogy for the literal pointing provided by embodiments described herein is the touch-sensitive screen (as found, for example, on many ATM machines). A touch-sensitive screen provides a one to one mapping between the two-dimensional display space on the screen and the two-dimensional input space of the screen surface. In an analogous fashion, the systems described herein provide a flexible mapping (possibly, but not necessarily, one to one) between a virtual space displayed on one or more screens and the physical space inhabited by the operator. Despite the usefulness of the analogy, it is worth understanding that the extension of this "mapping approach" to three dimensions, an arbitrarily large architectural environment, and multiple screens is non-trivial.

In addition to the components described herein, the system may also implement algorithms implementing a continuous, systems-level mapping (perhaps modified by rotation, translation, scaling or other geometrical transformations) between the physical space of the environment and the display space on each screen. The system also includes a rendering stack which takes the computational objects and the mapping and outputs a graphical representation of the virtual space. Additionally, the system of an embodiment includes an input events processing stack which takes event data from a control system (in the current embodiment both gestural and pointing data from the system and mouse input) and maps spatial data from input events to coordinates in virtual space. Translated events are then delivered to running applications. Furthermore, the system of an embodiment includes a "glue layer" that enables the system to host applications running across several computers on a local area network.

Embodiments of a spatial-continuum input system are described herein as comprising network-based data representation, transit, and interchange that includes a system called "plasma" that comprises subsystems "slawx", "proteins", and "pools", as described in detail below. The pools and proteins are components of methods and systems described herein for encapsulating data that is to be shared between or across processes. These mechanisms also include slawx (plural of "slaw") in addition to the proteins and pools. Generally, slawx provide the lowest-level of data definition for inter-process exchange, proteins provide mid-level structure and hooks for querying and filtering, and pools provide for high-level organization and access semantics. Slawx include a mechanism for efficient, platform-independent data representation and access. Proteins provide a data encapsulation and transport scheme using slawx as the payload. Pools provide structured and flexible aggregation, ordering, filtering, and distribution of proteins within a process, among local processes, across a network between remote or distributed processes, and via longer term (e.g. on-disk, etc.) storage.

The configuration and implementation of the embodiments described herein include several constructs that together enable numerous capabilities. For example, the embodiments described herein provide efficient exchange of data between large numbers of processes as described above. The embodiments described herein also provide flexible data "typing" and structure, so that widely varying kinds and uses of data are supported. Furthermore, embodiments described herein include flexible mechanisms for data exchange (e.g., local memory, disk, network, etc.), all driven by substantially similar application programming interfaces (APIs). Moreover, embodiments described enable data exchange between processes written in different programming languages. Additionally, embodiments described herein enable automatic maintenance of data caching and aggregate state.

Figure 9:
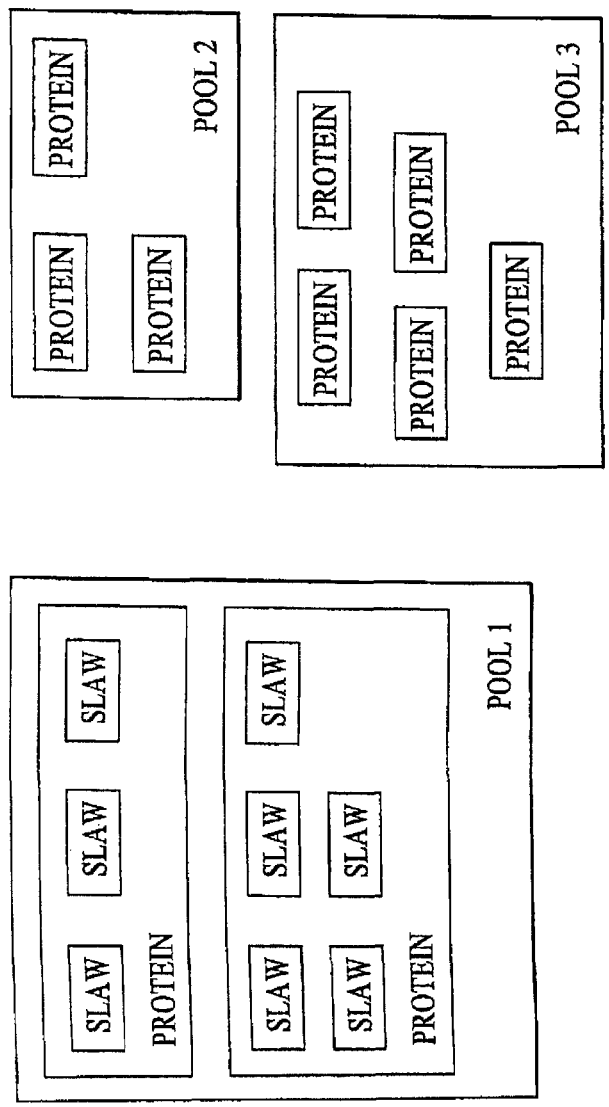
FIG. 9 is a block diagram of a processing environment including data representations using slawx, proteins, and pools, under an embodiment.

FIG. 9 is a block diagram of a processing environment including data representations using slawx, proteins, and pools, under an embodiment. The principal constructs of the embodiments presented herein include slawx (plural of "slaw"), proteins, and pools. Slawx as described herein includes a mechanism for efficient, platform-independent data representation and access. Proteins, as described in detail herein, provide a data encapsulation and transport scheme, and the payload of a protein of an embodiment includes slawx. Pools, as described herein, provide structured yet flexible aggregation, ordering, filtering, and distribution of proteins. The pools provide access to data, by virtue of proteins, within a process, among local processes, across a network between remote or distributed processes, and via 'longer term' (e.g. on-disk) storage.

Figure 10:
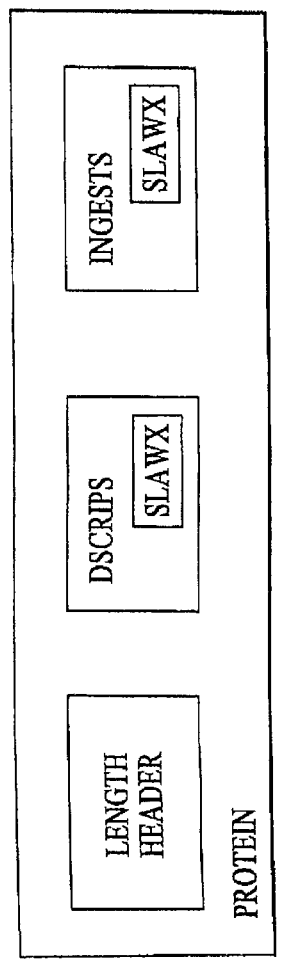
FIG. 10 is a block diagram of a protein, under an embodiment.

FIG. 10 is a block diagram of a protein, under an embodiment. The protein includes a length header, a descrip, and an ingest. Each of the descrip and ingest includes slaw or slawx, as described in detail below.

Figure 11:
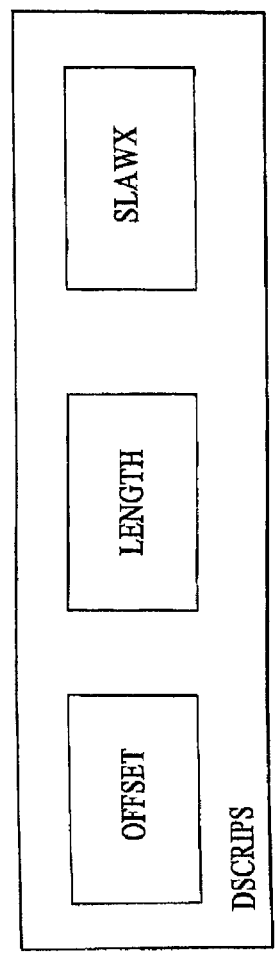
FIG. 11 is a block diagram of a descrip, under an embodiment.

FIG. 11 is a block diagram of a descrip, under an embodiment. The descrip includes an offset, a length, and slawx, as described in detail below.

Figure 12:
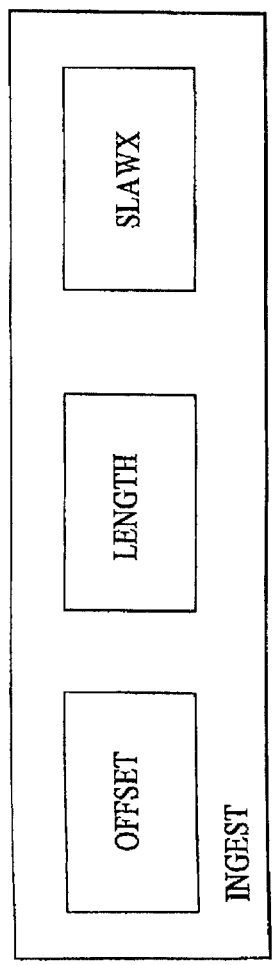
FIG. 12 is a block diagram of an ingest, under an embodiment.

FIG. 12 is a block diagram of an ingest, under an embodiment. The ingest includes an offset, a length, and slawx, as described in detail below.

Figure 13:
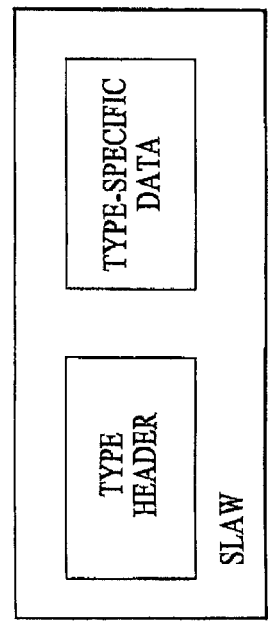
FIG. 13 is a block diagram of a slaw, under an embodiment.

FIG. 13 is a block diagram of a slaw, under an embodiment. The slaw includes a type header and type-specific data, as described in detail below.

Figure 14A:
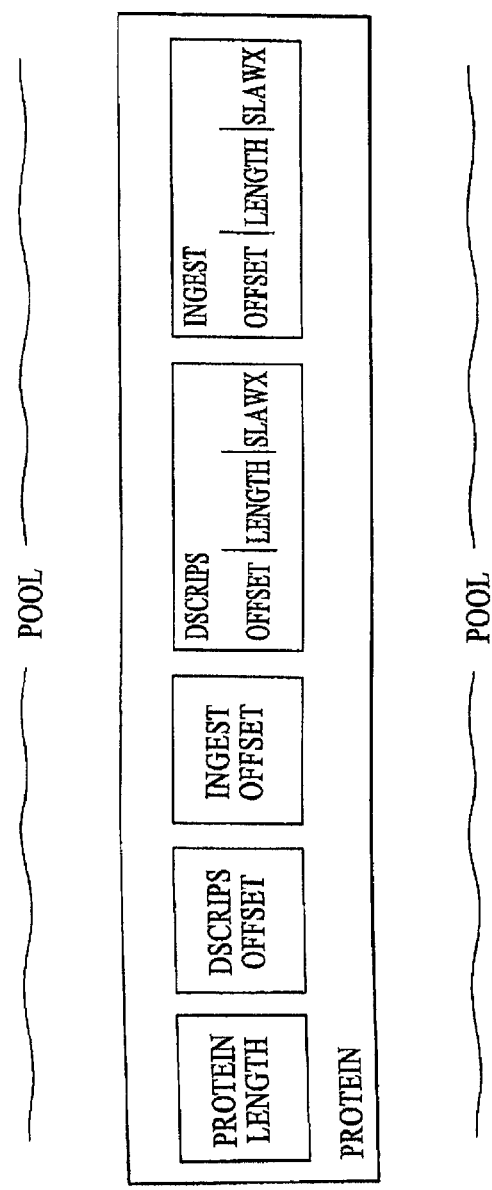
FIG. 14A is a block diagram of a protein in a pool, under an embodiment.

FIG. 14A is a block diagram of a protein in a pool, under an embodiment. The protein includes a length header ("protein length"), a descrips offset, an ingests offset, a descrip, and an ingest. The descrips includes an offset, a length, and a slaw. The ingest includes an offset, a length, and a slaw.

The protein as described herein is a mechanism for encapsulating data that needs to be shared between processes, or moved across a bus or network or other processing structure. As an example, proteins provide an improved mechanism for transport and manipulation of data including data corresponding to or associated with user interface events; in particular, the user interface events of an embodiment include those of the gestural interface described above. As a further example, proteins provide an improved mechanism for transport and manipulation of data including, but not limited to, graphics data or events, and state information, to name a few. A protein is a structured record format and an associated set of methods for manipulating records. Manipulation of records as used herein includes putting data into a structure, taking data out of a structure, and querying the format and existence of data. Proteins are configured to be used via code written in a variety of computer languages. Proteins are also configured to be the basic building block for pools, as described herein. Furthermore, proteins are configured to be natively able to move between processors and across networks while maintaining intact the data they include.

In contrast to conventional data transport mechanisms, proteins are untyped. While being untyped, the proteins provide a powerful and flexible pattern-matching facility, on top of which "type-like" functionality is implemented. Proteins configured as described herein are also inherently multi-point (although point-to-point forms are easily implemented as a subset of multi-point transmission). Additionally, proteins define a "universal" record format that does not differ (or differs only in the types of optional optimizations that are performed) between in-memory, on-disk, and on-the-wire (network) formats, for example.

Figure 15:
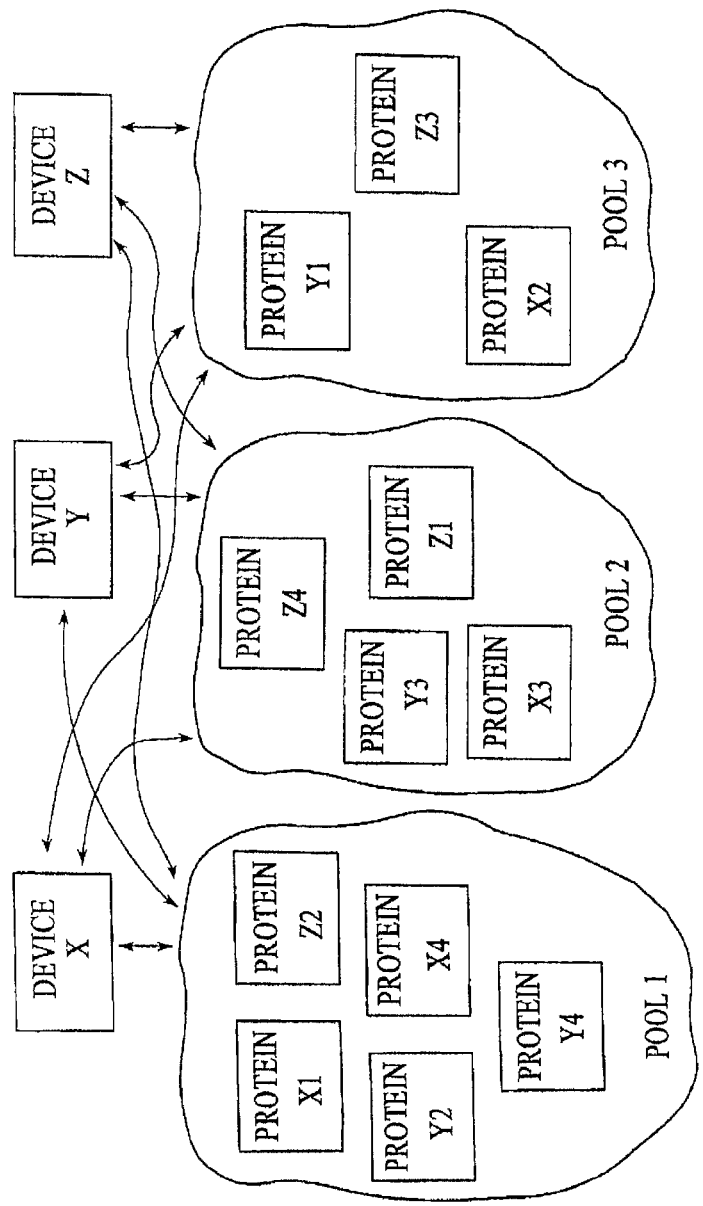
FIG. 15 is a block diagram of a processing environment including data exchange using slawx, proteins, and pools, under an embodiment.

Referring to FIGS. 15 and 19A, a protein of an embodiment is a linear sequence of bytes. Within these bytes are encapsulated a descrips list and a set of key-value pairs called ingests. The descrips list includes an arbitrarily elaborate but efficiently filterable per-protein event description. The ingests include a set of key-value pairs that comprise the actual contents of the protein.

Proteins' concern with key-value pairs, as well as some core ideas about network-friendly and multi-point data interchange, is shared with earlier systems that privilege the concept of "tuples" (e.g., Linda, Jini). Proteins differ from tuple-oriented systems in several major ways, including the use of the descrips list to provide a standard, optimizable pattern matching substrate. Proteins also differ from tuple-oriented systems in the rigorous specification of a record format appropriate for a variety of storage and language constructs, along with several particular implementations of "interfaces" to that record format.

Turning to a description of proteins, the first four or eight bytes of a protein specify the protein's length, which must be a multiple of 16 bytes in an embodiment. This 16-byte granularity ensures that byte-alignment and bus-alignment efficiencies are achievable on contemporary hardware. A protein that is not naturally "quad-word aligned" is padded with arbitrary bytes so that its length is a multiple of 16 bytes.

The length portion of a protein has the following format: 32 bits specifying length, in big-endian format, with the four lowest-order bits serving as flags to indicate macro-level protein structure characteristics; followed by 32 further bits if the protein's length is greater than 2^32 bytes.

The 16-byte-alignment proviso of an embodiment means that the lowest order bits of the first four bytes are available as flags. And so the first three low-order bit flags indicate whether the protein's length can be expressed in the first four bytes or requires eight, whether the protein uses big-endian or little-endian byte ordering, and whether the protein employs standard or non-standard structure, respectively, but the protein is not so limited. The fourth flag bit is reserved for future use.

If the eight-byte length flag bit is set, the length of the protein is calculated by reading the next four bytes and using them as the high-order bytes of a big-endian, eight-byte integer (with the four bytes already read supplying the low-order portion). If the little-endian flag is set, all binary numerical data in the protein is to be interpreted as little-endian (otherwise, big-endian). If the non-standard flag bit is set, the remainder of the protein does not conform to the standard structure to be described below.

Non-standard protein structures will not be discussed further herein, except to say that there are various methods for describing and synchronizing on non-standard protein formats available to a systems programmer using proteins and pools, and that these methods can be useful when space or compute cycles are constrained. For example, the shortest protein of an embodiment is sixteen bytes. A standard-format protein cannot fit any actual payload data into those sixteen bytes (the lion's share of which is already relegated to describing the location of the protein's component parts). But a non-standard format protein could conceivably use 12 of its 16 bytes for data. Two applications exchanging proteins could mutually decide that any 16-byte-long proteins that they emit always include 12 bytes representing, for example, 12 8-bit sensor values from a real-time analog-to-digital converter.

Immediately following the length header, in the standard structure of a protein, two more variable-length integer numbers appear. These numbers specify offsets to, respectively, the first element in the descrips list and the first key-value pair (ingest). These offsets are also referred to herein as the descrips offset and the ingests offset, respectively. The byte order of each quad of these numbers is specified by the protein endianness flag bit. For each, the most significant bit of the first four bytes determines whether the number is four or eight bytes wide. If the most significant bit (msb) is set, the first four bytes are the most significant bytes of a double-word (eight byte) number. This is referred to herein as "offset form". Use of separate offsets pointing to descrips and pairs allows descrips and pairs to be handled by different code paths, making possible particular optimizations relating to, for example, descrips pattern-matching and protein assembly. The presence of these two offsets at the beginning of a protein also allows for several useful optimizations.

Most proteins will not be so large as to require eight-byte lengths or pointers, so in general the length (with flags) and two offset numbers will occupy only the first three bytes of a protein. On many hardware or system architectures, a fetch or read of a certain number of bytes beyond the first is "free" (e.g., 16 bytes take exactly the same number of clock cycles to pull across the Cell processor's main bus as a single byte).

In many instances it is useful to allow implementation-specific or context-specific caching or metadata inside a protein. The use of offsets allows for a "hole" of arbitrary size to be created near the beginning of the protein, into which such metadata may be slotted. An implementation that can make use of eight bytes of metadata gets those bytes for free on many system architectures with every fetch of the length header for a protein.

The descrips offset specifies the number of bytes between the beginning of the protein and the first descrip entry. Each descrip entry comprises an offset (in offset form, of course) to the next descrip entry, followed by a variable-width length field (again in offset format), followed by a slaw. If there are no further descrips, the offset is, by rule, four bytes of zeros. Otherwise, the offset specifies the number of bytes between the beginning of this descrip entry and a subsequent descrip entry. The length field specifies the length of the slaw, in bytes.

In most proteins, each descrip is a string, formatted in the slaw string fashion: a four-byte length/type header with the most significant bit set and only the lower 30 bits used to specify length, followed by the header's indicated number of data bytes. As usual, the length header takes its endianness from the protein. Bytes are assumed to encode UTF-8 characters (and thus—nota bene—the number of characters is not necessarily the same as the number of bytes).

The ingests offset specifies the number of bytes between the beginning of the protein and the first ingest entry. Each ingest entry comprises an offset (in offset form) to the next ingest entry, followed again by a length field and a slaw. The ingests offset is functionally identical to the descrips offset, except that it points to the next ingest entry rather than to the next descrip entry.

In most proteins, every ingest is of the slaw cons type comprising a two-value list, generally used as a key/value pair. The slaw cons record comprises a four-byte length/type header with the second most significant bit set and only the lower 30 bits used to specify length; a four-byte offset to the start of the value (second) element; the four-byte length of the key element; the slaw record for the key element; the four-byte length of the value element; and finally the slaw record for the value element.

Generally, the cons key is a slaw string. The duplication of data across the several protein and slaw cons length and offsets field provides yet more opportunity for refinement and optimization.

The construct used under an embodiment to embed typed data inside proteins, as described above, is a tagged byte-sequence specification and abstraction called a "slaw" (the plural is "slawx"). A slaw is a linear sequence of bytes representing a piece of (possibly aggregate) typed data, and is associated with programming-language-specific APIs that allow slawx to be created, modified and moved around between memory spaces, storage media, and machines. The slaw type scheme is intended to be extensible and as lightweight as possible, and to be a common substrate that can be used from any programming language.

The desire to build an efficient, large-scale inter-process communication mechanism is the driver of the slaw configuration. Conventional programming languages provide sophisticated data structures and type facilities that work well in process-specific memory layouts, but these data representations invariably break down when data needs to be moved between processes or stored on disk. The slaw architecture is, first, a substantially efficient, multi-platform friendly, low-level data model for inter-process communication.

But even more importantly, slawx are configured to influence, together with proteins, and enable the development of future computing hardware (microprocessors, memory controllers, disk controllers). A few specific additions to, say, the instruction sets of commonly available microprocessors make it possible for slawx to become as efficient even for single-process, in-memory data layout as the schema used in most programming languages.

Each slaw comprises a variable-length type header followed by a type-specific data layout. In an example embodiment, which supports full slaw functionality in C, C++ and Ruby for example, types are indicated by a universal integer defined in system header files accessible from each language. More sophisticated and flexible type resolution functionality is also enabled: for example, indirect typing via universal object IDs and network lookup.

The slaw configuration of an embodiment allows slaw records to be used as objects in language-friendly fashion from both Ruby and C++, for example. A suite of utilities external to the C++ compiler sanity-check slaw byte layout, create header files and macros specific to individual slaw types, and auto-generate bindings for Ruby. As a result, well-configured slaw types are quite efficient even when used from within a single process. Any slaw anywhere in a process's accessible memory can be addressed without a copy or "deserialization" step.

Slaw functionality of an embodiment includes API facilities to perform one or more of the following: create a new slaw of a specific type; create or build a language-specific reference to a slaw from bytes on disk or in memory; embed data within a slaw in type-specific fashion; query the size of a slaw; retrieve data from within a slaw; clone a slaw; and translate the endianness and other format attributes of all data within a slaw. Every species of slaw implements the above behaviors.

FIGS. 14B and 14C show a slaw header format, under an embodiment. A detailed description of the slaw follows.

The internal structure of each slaw optimizes each of type resolution, access to encapsulated data, and size information for that slaw instance. In an embodiment, the full set of slaw types is by design minimally complete, and includes: the slaw string; the slaw cons (i.e. dyad); the slaw list; and the slaw numerical object, which itself represents a broad set of individual numerical types understood as permutations of a half-dozen or so basic attributes. The other basic property of any slaw is its size. In an embodiment, slawx have bytelengths quantized to multiples of four; these four-byte words are referred to herein as 'quads'. In general, such quad-based sizing aligns slawx well with the configurations of modern computer hardware architectures.

The first four bytes of every slaw in an embodiment comprise a header structure that encodes type-description and other metainformation, and that ascribes specific type meanings to particular bit patterns. For example, the first (most significant) bit of a slaw header is used to specify whether the size (length in quad-words) of that slaw follows the initial four-byte type header. When this bit is set, it is understood that the size of the slaw is explicitly recorded in the next four bytes of the slaw (e.g., bytes five through eight); if the size of the slaw is such that it cannot be represented in four bytes (i.e. if the size is or is larger than two to the thirty-second power) then the next-most-significant bit of the slaw's initial four bytes is also set, which means that the slaw has an eight-byte (rather than four byte) length. In that case, an inspecting process will find the slaw's length stored in ordinal bytes five through twelve. On the other hand, the small number of slaw types means that in many cases a fully specified typal bit-pattern "leaves unused" many bits in the four byte slaw header; and in such cases these bits may be employed to encode the slaw's length, saving the bytes (five through eight) that would otherwise be required.

For example, an embodiment leaves the most significant bit of the slaw header (the "length follows" flag) unset and sets the next bit to indicate that the slaw is a "wee cons", and in this case the length of the slaw (in quads) is encoded in the remaining thirty bits. Similarly, a "wee string" is marked by the pattern 001 in the header, which leaves twenty-nine bits for representation of the slaw-string's length; and a leading 0001 in the header describes a "wee list", which by virtue of the twenty-eight available length-representing bits can be a slaw list of up to two-to-the-twenty-eight quads in size. A "full string" (or cons or list) has a different bit signature in the header, with the most significant header bit necessarily set because the slaw length is encoded separately in bytes five through eight (or twelve, in extreme cases). Note that the Plasma implementation "decides" at the instant of slaw construction whether to employ the "wee" or the "full" version of these constructs (the decision is based on whether the resulting size will "fit" in the available wee bits or not), but the full-vs.-wee detail is hidden from the user of the Plasma implementation, who knows and cares only that she is using a slaw string, or a slaw cons, or a slaw list.

Numeric slawx are, in an embodiment, indicated by the leading header pattern 00001. Subsequent header bits are used to represent a set of orthogonal properties that may be combined in arbitrary permutation. An embodiment employs, but is not limited to, five such character bits to indicate whether or not the number is: (1) floating point; (2) complex; (3) unsigned; (4) "wide"; (5) "stumpy" ((4) "wide" and (5) "stumpy" are permuted to indicate eight, sixteen, thirty-two, and sixty-four bit number representations). Two additional bits (e.g., (7) and (8)) indicate that the encapsulated numeric data is a two-, three-, or four-element vector (with both bits being zero suggesting that the numeric is a "one-element vector" (i.e. a scalar)). In this embodiment the eight bits of the fourth header byte are used to encode the size (in bytes, not quads) of the encapsulated numeric data. This size encoding is offset by one, so that it can represent any size between and including one and two hundred fifty-six bytes. Finally, two character bits (e.g., (9) and (10)) are used to indicate that the numeric data encodes an array of individual numeric entities, each of which is of the type described by character bits (1) through (8). In the case of an array, the individual numeric entities are not each tagged with additional headers, but are packed as continuous data following the single header and, possibly, explicit slaw size information.

This embodiment affords simple and efficient slaw duplication (which can be implemented as a byte-for-byte copy) and extremely straightforward and efficient slaw comparison (two slawx are the same in this embodiment if and only if there is a one-to-one match of each of their component bytes considered in sequence). This latter property is important, for example, to an efficient implementation of the protein architecture, one of whose critical and pervasive features is the ability to search through or 'match on' a protein's descrips list.

Further, the embodiments herein allow aggregate slaw forms (e.g., the slaw cons and the slaw list) to be constructed simply and efficiently. For example, an embodiment builds a slaw cons from two component slawx, which may be of any type, including themselves aggregates, by: (a) querying each component slaw's size; (b) allocating memory of size equal to the sum of the sizes of the two component slawx and the one, two, or three quads needed for the header-plus-size structure; (c) recording the slaw header (plus size information) in the first four, eight, or twelve bytes; and then (d) copying the component slawx's bytes in turn into the immediately succeeding memory. Significantly, such a construction routine need know nothing about the types of the two component slawx; only their sizes (and accessibility as a sequence of bytes) matters. The same process pertains to the construction of slaw lists, which are ordered encapsulations of arbitrarily many sub-slawx of (possibly) heterogeneous type.

A further consequence of the slaw system's fundamental format as sequential bytes in memory obtains in connection with "traversal" activities—a recurring use pattern uses, for example, sequential access to the individual slawx stored in a slaw list. The individual slawx that represent the descrips and ingests within a protein structure must similarly be traversed. Such maneuvers are accomplished in a stunningly straightforward and efficient manner: to "get to" the next slaw in a slaw list, one adds the length of the current slaw to its location in memory, and the resulting memory location is identically the header of the next slaw. Such simplicity is possible because the slaw and protein design eschews "indirection"; there are no pointers; rather, the data simply exists, in its totality, in situ.

To the point of slaw comparison, a complete implementation of the Plasma system must acknowledge the existence of differing and incompatible data representation schemes across and among different operating systems, CPUs, and hardware architectures. Major such differences include byte-ordering policies (e.g., little-vs. big-endianness) and floating-point representations; other differences exist. The Plasma specification requires that the data encapsulated by slawx be guaranteed interprable (i.e., must appear in the native format of the architecture or platform from which the slaw is being inspected. This requirement means in turn that the Plasma system is itself responsible for data format conversion. However, the specification stipulates only that the conversion take place before a slaw becomes "at all visible" to an executing process that might inspect it. It is therefore up to the individual implementation at which point it chooses to perform such format c conversion; two appropriate approaches are that slaw data payloads are conformed to the local architecture's data format (1) as an individual slaw is "pulled out" of a protein in which it had been packed, or (2) for all slaw in a protein simultaneously, as that protein is extracted from the pool in which it was resident. Note that the conversion stipulation considers the possibility of hardware-assisted implementations. For example, networking chipsets built with explicit Plasma capability may choose to perform format conversion intelligently and at the "instant of transmission", based on the known characteristics of the receiving system. Alternately, the process of transmission may convert data payloads into a canonical format, with the receiving process symmetrically converting from canonical to "local" format. Another embodiment performs format conversion "at the metal", meaning that data is always stored in canonical format, even in local memory, and that the memory controller hardware itself performs the conversion as data is retrieved from memory and placed in the registers of the proximal CPU.

Figure 14D:
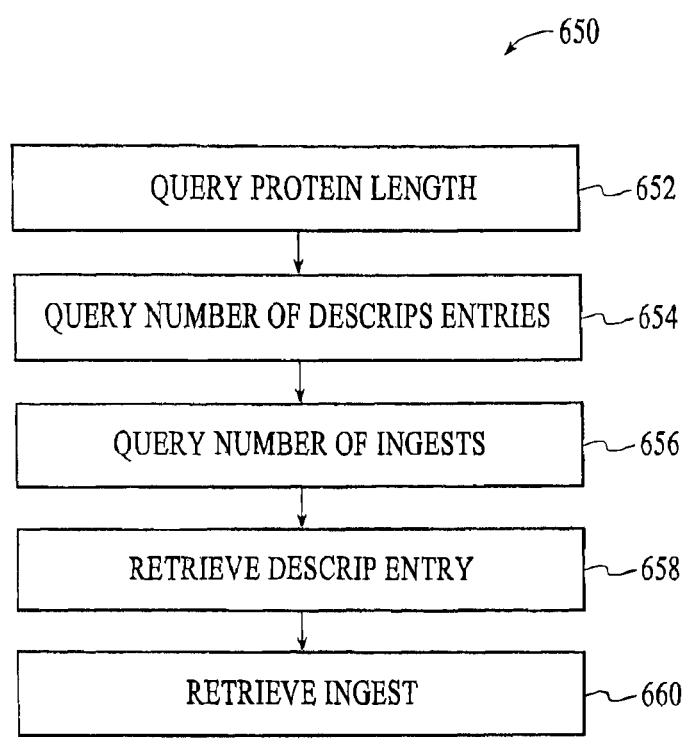
FIG. 14D is a flow diagram for using proteins, under an embodiment.

A minimal (and read-only) protein implementation of an embodiment includes operation or behavior in one or more applications or programming languages making use of proteins. FIG. 14D is a flow diagram 650 for using proteins, under an embodiment. Operation begins by querying 652 the length in bytes of a protein. The number of descrips entries is queried 654. The number of ingests is queried 656. A descrip entry is retrieved 658 by index number. An ingest is retrieved 660 by index number.

Figure 14E:
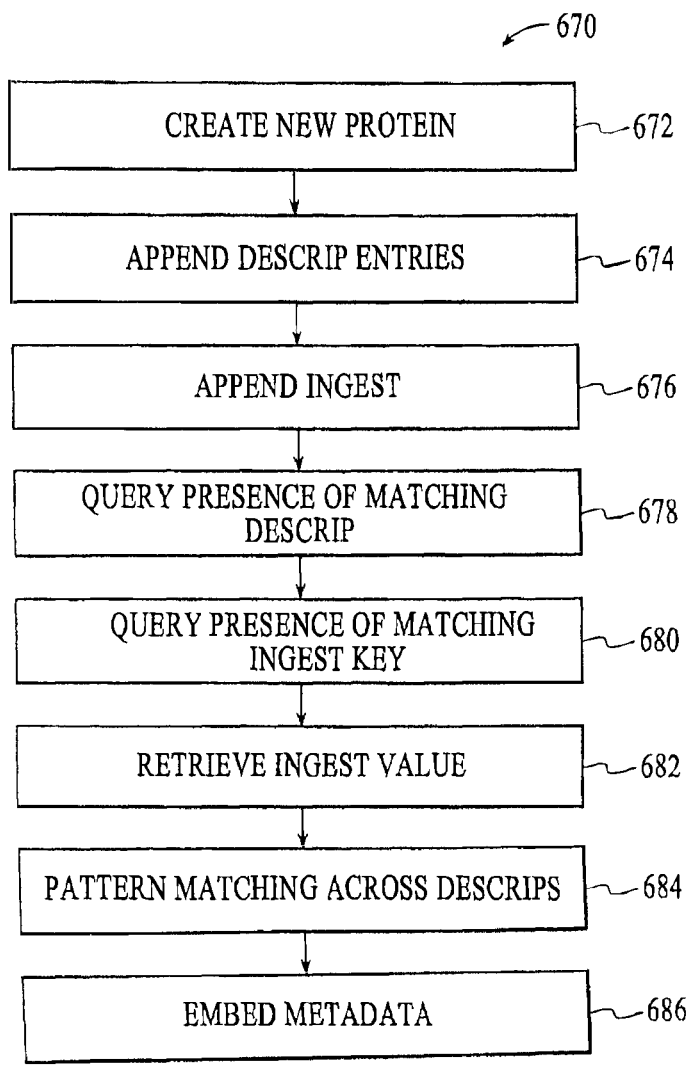
FIG. 14E is a flow diagram for constructing or generating proteins, under an embodiment.

The embodiments described herein also define basic methods allowing proteins to be constructed and filled with data, helper-methods that make common tasks easier for programmers, and hooks for creating optimizations. FIG. 14E is a flow diagram 670 for constructing or generating proteins, under an embodiment. Operation begins with creation 672 of a new protein. A series of descrips entries are appended 674. An ingest is also appended 676. The presence of a matching descrip is queried 678, and the presence of a matching ingest key is queried 68o. Given an ingest key, an ingest value is retrieved 682. Pattern matching is performed 684 across descrips. Non-structured metadata is embedded 686 near the beginning of the protein.

As described above, slawx provide the lowest-level of data definition for inter-process exchange, proteins provide mid-level structure and hooks for querying and filtering, and pools provide for high-level organization and access semantics. The pool is a repository for proteins, providing linear sequencing and state caching. The pool also provides multi-process access by multiple programs or applications of numerous different types. Moreover, the pool provides a set of common, optimizable filtering and pattern-matching behaviors.

The pools of an embodiment, which can accommodate tens of thousands of proteins, function to maintain state, so that individual processes can offload much of the tedious bookkeeping common to multi-process program code. A pool maintains or keeps a large buffer of past proteins available—the Platonic pool is explicitly infinite—so that participating processes can scan both backwards and forwards in a pool at will. The size of the buffer is implementation dependent, of course, but in common usage it is often possible to keep proteins in a pool for hours or days.

The most common style of pool usage as described herein hews to a biological metaphor, in contrast to the mechanistic, point-to-point approach taken by existing inter-process communication frameworks. The name protein alludes to biological inspiration: data proteins in pools are available for flexible querying and pattern matching by a large number of computational processes, as chemical proteins in a living organism are available for pattern matching and filtering by large numbers of cellular agents.

Two additional abstractions lean on the biological metaphor, including use of "handlers", and the Golgi framework. A process that participates in a pool generally creates a number of handlers. Handlers are relatively small bundles of code that associate match conditions with handle behaviors. By tying one or more handlers to a pool, a process sets up flexible call-back triggers that encapsulate state and react to new proteins.

A process that participates in several pools generally inherits from an abstract Golgi class. The Golgi framework provides a number of useful routines for managing multiple pools and handlers. The Golgi class also encapsulates parent-child relationships, providing a mechanism for local protein exchange that does not use a pool.

A pools API provided under an embodiment is configured to allow pools to be implemented in a variety of ways, in order to account both for system-specific goals and for the available capabilities of given hardware and network architectures. The two fundamental system provisions upon which pools depend are a storage facility and a means of inter-process communication. The extant systems described herein use a flexible combination of shared memory, virtual memory, and disk for the storage facility, and IPC queues and TCP/IP sockets for inter-process communication.

Pool functionality of an embodiment includes, but is not limited to, the following: participating in a pool; placing a protein in a pool; retrieving the next unseen protein from a pool; rewinding or fast-forwarding through the contents (e.g., proteins) within a pool. Additionally, pool functionality can include, but is not limited to, the following: setting up a streaming pool call-back for a process; selectively retrieving proteins that match particular patterns of descrips or ingests keys; scanning backward and forwards for proteins that match particular patterns of descrips or ingests keys.

The proteins described above are provided to pools as a way of sharing the protein data contents with other applications. FIG. 15 is a block diagram of a processing environment including data exchange using slawx, proteins, and pools, under an embodiment. This example environment includes three devices (e.g., Device X, Device Y, and Device Z, collectively referred to herein as the "devices") sharing data through the use of slawx, proteins and pools as described above. Each of the devices is coupled to the three pools (e.g., Pool 1, Pool 2, Pool 3). Pool 1 includes numerous proteins (e.g., Protein X1, Protein Z2, Protein Y2, Protein X4, Protein Y4) contributed or transferred to the pool from the respective devices (e.g., protein Z2 is transferred or contributed to pool 1 by device Z, etc.). Pool 2 includes numerous proteins (e.g., Protein Z4, Protein Y3, Protein Z1, Protein X3) contributed or transferred to the pool from the respective devices (e.g., protein Y3 is transferred or contributed to pool 2 by device Y, etc.). Pool 3 includes numerous proteins (e.g., Protein Y1, Protein Z3, Protein X2) contributed or transferred to the pool from the respective devices (e.g., protein X2 is transferred or contributed to pool 3 by device X, etc.). While the example described above includes three devices coupled or connected among three pools, any number of devices can be coupled or connected in any manner or combination among any number of pools, and any pool can include any number of proteins contributed from any number or combination of devices. The proteins and pools of this example are as described above with reference to FIGS. 18-23.

Figure 16:
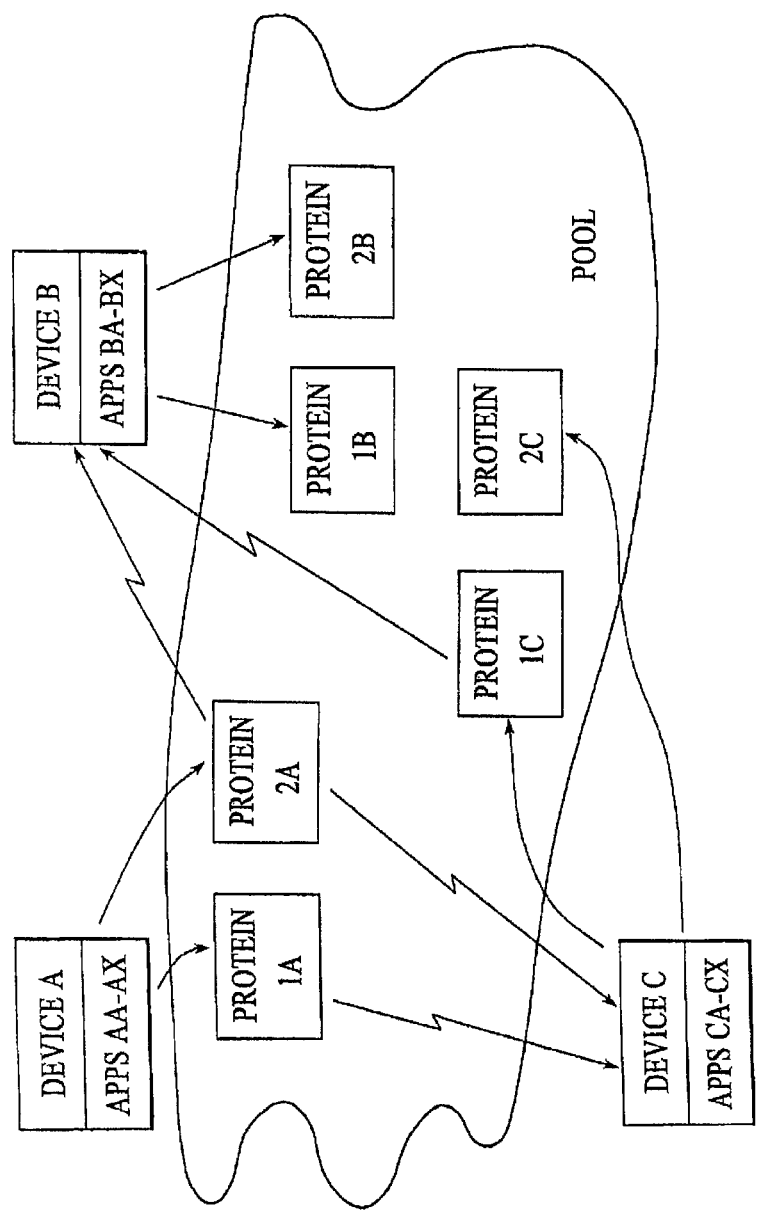
FIG. 16 is a block diagram of a processing environment including multiple devices and numerous programs running on one or more of the devices in which the Plasma constructs (i.e., pools, proteins, and slaw) are used to allow the numerous running programs to share and collectively respond to the events generated by the devices, under an embodiment.

FIG. 16 is a block diagram of a processing environment including multiple devices and numerous programs running on one or more of the devices in which the Plasma constructs (e.g., pools, proteins, and slaw) are used to allow the numerous running programs to share and collectively respond to the events generated by the devices, under an embodiment. This system is but one example of a multi-user, multi-device, multi-computer interactive control scenario or configuration. More particularly, in this example, an interactive system, comprising multiple devices (e.g., device A, B, etc.) and a number of programs (e.g., apps AA-AX, apps BA-BX, etc.) running on the devices uses the Plasma constructs (e.g., pools, proteins, and slaw) to allow the running programs to share and collectively respond to the events generated by these input devices.

In this example, each device (e.g., device A, B, etc.) translates discrete raw data generated by or output from the programs (e.g., apps AA-AX, apps BA-BX, etc.) running on that respective device into Plasma proteins and deposits those proteins into a Plasma pool. For example, program AX generates data or output and provides the output to device A which, in turn, translates the raw data into proteins (e.g., protein 1A, protein 2A, etc.) and deposits those proteins into the pool. As another example, program BC generates data and provides the data to device B which, in turn, translates the data into proteins (e.g., protein 1B, protein 2B, etc.) and deposits those proteins into the pool.

Each protein contains a descrip list that specifies the data or output registered by the application as well as identifying information for the program itself. Where possible, the protein descrips may also ascribe a general semantic meaning for the output event or action. The protein's data payload (e.g., ingests) carries the full set of useful state information for the program event.

The proteins, as described above, are available in the pool for use by any program or device coupled or connected to the pool, regardless of type of the program or device. Consequently, any number of programs running on any number of computers may extract event proteins from the input pool. These devices need only be able to participate in the pool via either the local memory bus or a network connection in order to extract proteins from the pool. An immediate consequence of this is the beneficial possibility of decoupling processes that are responsible for generating processing events from those that use or interpret the events. Another consequence is the multiplexing of sources and consumers of events so that devices may be controlled by one person or may be used simultaneously by several people (e.g., a Plasma-based input framework supports many concurrent users), while the resulting event streams are in turn visible to multiple event consumers.

As an example, device C can extract one or more proteins (e.g., protein 1A, protein 2A, etc.) from the pool. Following protein extraction, device C can use the data of the protein, retrieved or read from the slaw of the descrips and ingests of the protein, in processing events to which the protein data corresponds. As another example, device B can extract one or more proteins (e.g., protein 1C, protein 2A, etc.) from the pool. Following protein extraction, device B can use the data of the protein in processing events to which the protein data corresponds.

Devices and/or programs coupled or connected to a pool may skim backwards and forwards in the pool looking for particular sequences of proteins. It is often useful, for example, to set up a program to wait for the appearance of a protein matching a certain pattern, then skim backwards to determine whether this protein has appeared in conjunction with certain others. This facility for making use of the stored event history in the input pool often makes writing state management code unnecessary, or at least significantly reduces reliance on such undesirable coding patterns.

Figure 17:
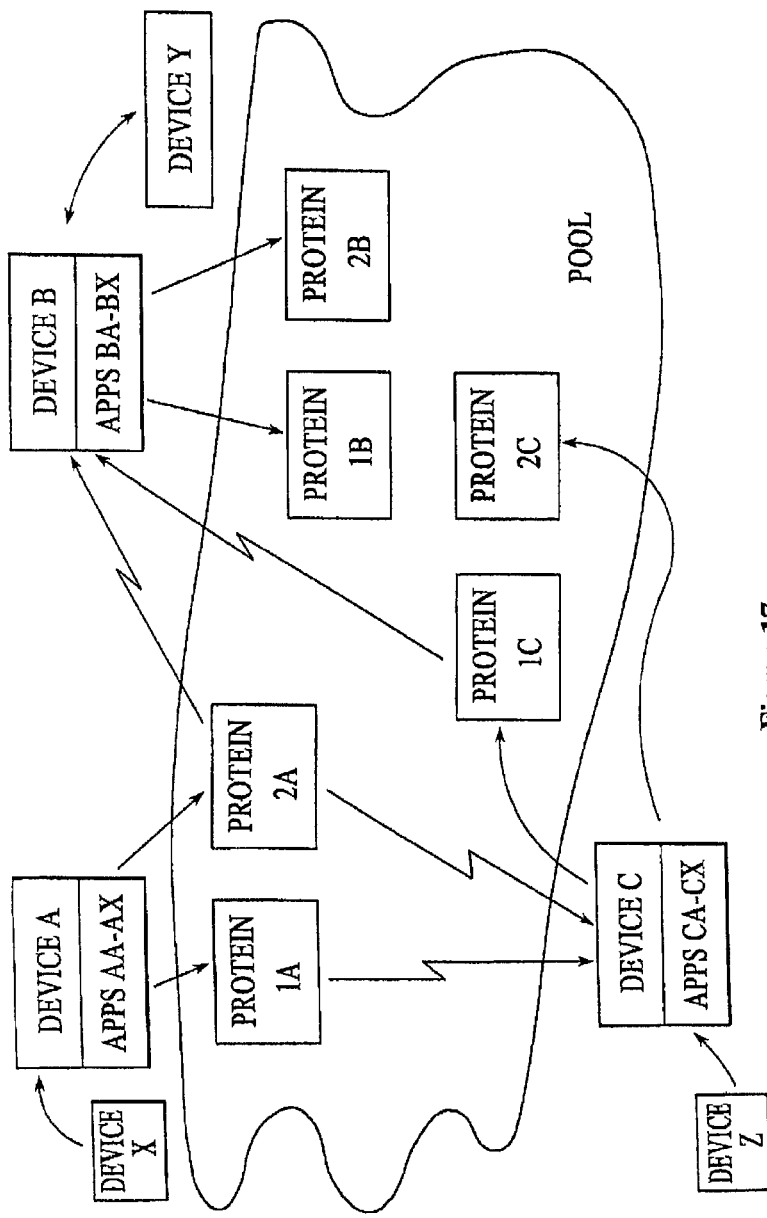
FIG. 17 is a block diagram of a processing environment including multiple devices and numerous programs running on one or more of the devices in which the Plasma constructs (i.e., pools, proteins, and slaw) are used to allow the numerous running programs to share and collectively respond to the events generated by the devices, under an alternative embodiment.

FIG. 17 is a block diagram of a processing environment including multiple devices and numerous programs running on one or more of the devices in which the Plasma constructs (e.g., pools, proteins, and slaw) are used to allow the numerous running programs to share and collectively respond to the events generated by the devices, under an alternative embodiment. This system is but one example of a multi-user, multi-device, multi-computer interactive control scenario or configuration. More particularly, in this example, an interactive system, comprising multiple devices (e.g., devices X and Y coupled to devices A and B, respectively) and a number of programs (e.g., apps AA-AX, apps BA-BX, etc.) running on one or more computers (e.g., device A, device B, etc.) uses the Plasma constructs (e.g., pools, proteins, and slaw) to allow the running programs to share and collectively respond to the events generated by these input devices.

In this example, each device (e.g., devices X and Y coupled to devices A and B, respectively) is managed and/or coupled to run under or in association with one or more programs hosted on the respective device (e.g., device A, device B, etc.) which translates the discrete raw data generated by the device (e.g., device X, device A, device Y, device B, etc.) hardware into Plasma proteins and deposits those proteins into a Plasma pool. For example, device X running in association with application AB hosted on device A generates raw data, translates the discrete raw data into proteins (e.g., protein 1A, protein 2A, etc.) and deposits those proteins into the pool. As another example, device X running in association with application AT hosted on device A generates raw data, translates the discrete raw data into proteins (e.g., protein 1A, protein 2A, etc.) and deposits those proteins into the pool. As yet another example, device Z running in association with application CD hosted on device C generates raw data, translates the discrete raw data into proteins (e.g., protein 1C, protein 2C, etc.) and deposits those proteins into the pool.

Each protein contains a descrip list that specifies the action registered by the input device as well as identifying information for the device itself. Where possible, the protein descrips may also ascribe a general semantic meaning for the device action. The protein's data payload (e.g., ingests) carries the full set of useful state information for the device event.

The proteins, as described above, are available in the pool for use by any program or device coupled or connected to the pool, regardless of type of the program or device. Consequently, any number of programs running on any number of computers may extract event proteins from the input pool. These devices need only be able to participate in the pool via either the local memory bus or a network connection in order to extract proteins from the pool. An immediate consequence of this is the beneficial possibility of decoupling processes that are responsible for generating processing events from those that use or interpret the events. Another consequence is the multiplexing of sources and consumers of events so that input devices may be controlled by one person or may be used simultaneously by several people (e.g., a Plasma-based input framework supports many concurrent users), while the resulting event streams are in turn visible to multiple event consumers.

Devices and/or programs coupled or connected to a pool may skim backwards and forwards in the pool looking for particular sequences of proteins. It is often useful, for example, to set up a program to wait for the appearance of a protein matching a certain pattern, then skim backwards to determine whether this protein has appeared in conjunction with certain others. This facility for making use of the stored event history in the input pool often makes writing state management code unnecessary, or at least significantly reduces reliance on such undesirable coding patterns.

Figure 18:
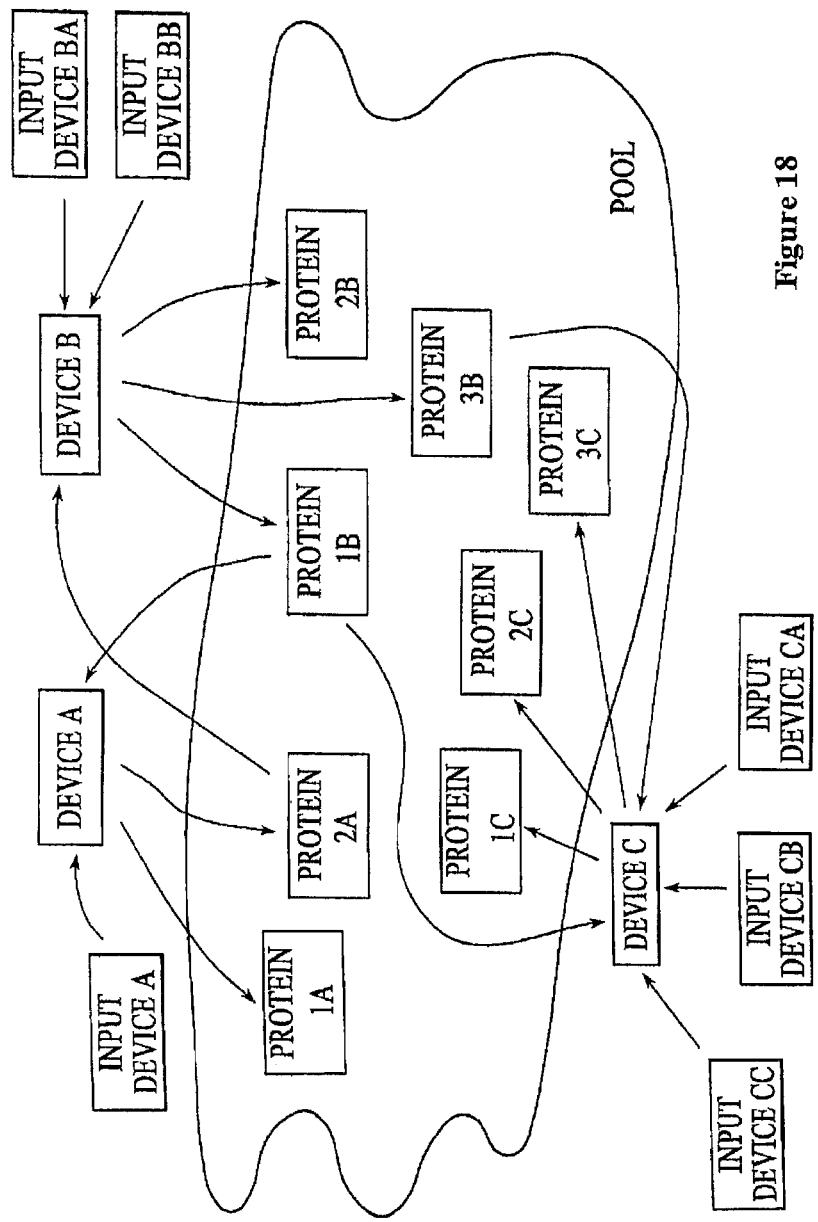
FIG. 18 is a block diagram of a processing environment including multiple input devices coupled among numerous programs running on one or more of the devices in which the Plasma constructs (i.e., pools, proteins, and slaw) are used to allow the numerous running programs to share and collectively respond to the events generated by the input devices, under another alternative embodiment.

FIG. 18 is a block diagram of a processing environment including multiple input devices coupled among numerous programs running on one or more of the devices in which the Plasma constructs (e.g., pools, proteins, and slaw) are used to allow the numerous running programs to share and collectively respond to the events generated by the input devices, under another alternative embodiment. This system is but one example of a multi-user, multi-device, multi-computer interactive control scenario or configuration. More particularly, in this example, an interactive system, comprising multiple input devices (e.g., input devices A, B, BA, and BB, etc.) and a number of programs (not shown) running on one or more computers (e.g., device A, device B, etc.) uses the Plasma constructs (e.g., pools, proteins, and slaw) to allow the running programs to share and collectively respond to the events generated by these input devices.

In this example, each input device (e.g., input devices A, B, BA, and BB, etc.) is managed by a software driver program hosted on the respective device (e.g., device A, device B, etc.) which translates the discrete raw data generated by the input device hardware into Plasma proteins and deposits those proteins into a Plasma pool. For example, input device A generates raw data and provides the raw data to device A which, in turn, translates the discrete raw data into proteins (e.g., protein 1A, protein 2A, etc.) and deposits those proteins into the pool. As another example, input device BB generates raw data and provides the raw data to device B which, in turn, translates the discrete raw data into proteins (e.g., protein 1B, protein 3B, etc.) and deposits those proteins into the pool.

Each protein contains a descrip list that specifies the action registered by the input device as well as identifying information for the device itself. Where possible, the protein descrips may also ascribe a general semantic meaning for the device action. The protein's data payload (e.g., ingests) carries the full set of useful state information for the device event.

To illustrate, here are example proteins for two typical events in such a system. Proteins are represented here as text however, in an actual implementation, the constituent parts of these proteins are typed data bundles (e.g., slaw). The protein describing a g-speak "one finger click" pose (described in the Related Applications) is as follows:
[Descrips: {point, engage, one, one-finger-engage, hand, pilot-id-02, hand-id-23}
Ingests: {pilot-id=>02,
hand-id=>23,
pos=>[0.0, 0.0, 0.0]
angle-axis=>[0.0, 0.0, 0.0, 0.707]
gripe=> . . . ^||:vx
time=>184437103.29}]

As a further example, the protein describing a mouse click is as follows:
[Descrips: {point, click, one, mouse-click, button-one, mouse-id-02}
Ingests: {mouse-id=>23,
pos=>[0.0, 0.0, 0.0]
time=>184437124.80}]

Either or both of the sample proteins foregoing might cause a participating program of a host device to run a particular portion of its code. These programs may be interested in the general semantic labels: the most general of all, "point", or the more specific pair, "engage, one". Or they may be looking for events that would plausibly be generated only by a precise device: "one-finger-engage", or even a single aggregate object, "hand-id-23".

The proteins, as described above, are available in the pool for use by any program or device coupled or connected to the pool, regardless of type of the program or device. Consequently, any number of programs running on any number of computers may extract event proteins from the input pool. These devices need only be able to participate in the pool via either the local memory bus or a network connection in order to extract proteins from the pool. An immediate consequence of this is the beneficial possibility of decoupling processes that are responsible for generating 'input events' from those that use or interpret the events.

Another consequence is the multiplexing of sources and consumers of events so that input devices may be controlled by one person or may be used simultaneously by several people (e.g., a Plasma-based input framework supports many concurrent users, while the resulting event streams are in turn visible to multiple event consumers.

As an example or protein use, device C can extract one or more proteins (e.g., protein 1B, etc.) from the pool. Following protein extraction, device C can use the data of the protein, retrieved or read from the slaw of the descrips and ingests of the protein, in processing input events of input devices CA and CC to which the protein data corresponds. As another example, device A can extract one or more proteins (e.g., protein 1B, etc.) from the pool. Following protein extraction, device A can use the data of the protein in processing input events of input device A to which the protein data corresponds.

Devices and/or programs coupled or connected to a pool may skim backwards and forwards in the pool looking for particular sequences of proteins. It is often useful, for example, to set up a program to wait for the appearance of a protein matching a certain pattern, then skim backwards to determine whether this protein has appeared in conjunction with certain others. This facility for making use of the stored event history in the input pool often makes writing state management code unnecessary, or at least significantly reduces reliance on such undesirable coding patterns.

Examples of input devices that are used in the embodiments of the system described herein include gestural input sensors, keyboards, mice, infrared remote controls such as those used in consumer electronics, and task-oriented tangible media objects, to name a few.

Figure 19:
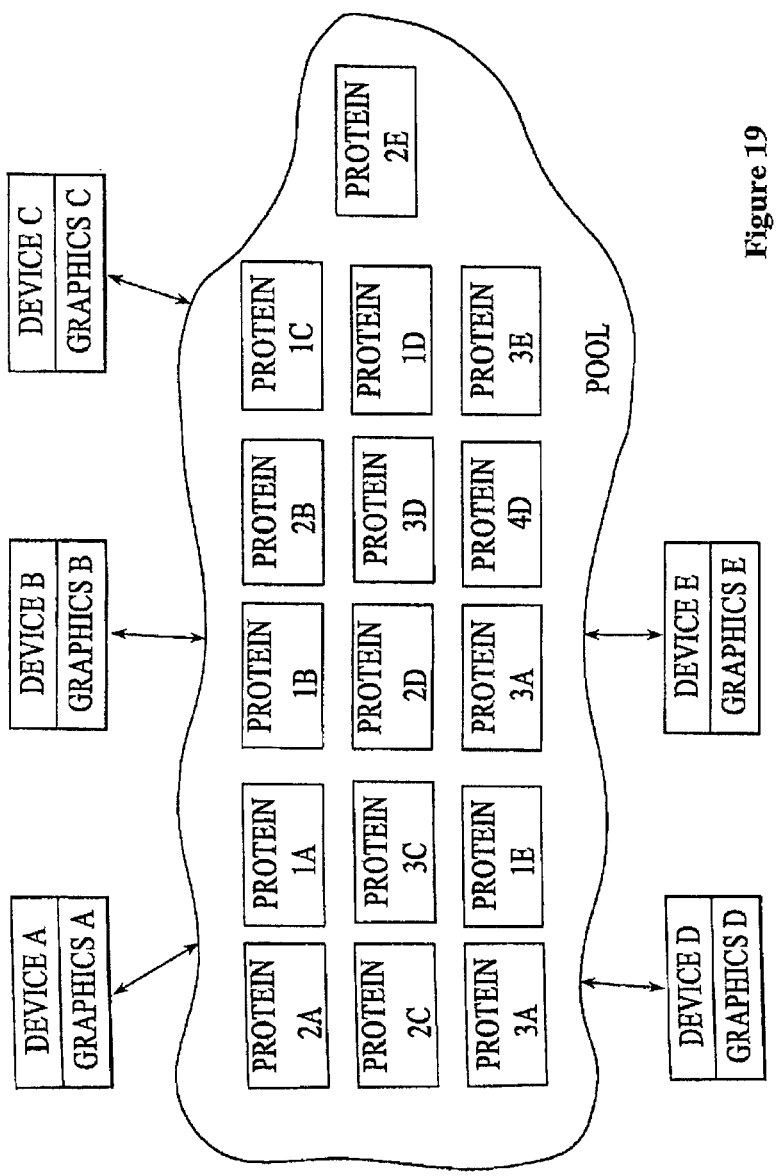
FIG. 19 is a block diagram of a processing environment including multiple devices coupled among numerous programs running on one or more of the devices in which the Plasma constructs (i.e., pools, proteins, and slaw) are used to allow the numerous running programs to share and collectively respond to the graphics events generated by the devices, under yet another alternative embodiment.

FIG. 19 is a block diagram of a processing environment including multiple devices coupled among numerous programs running on one or more of the devices in which the Plasma constructs (e.g., pools, proteins, and slaw) are used to allow the numerous running programs to share and collectively respond to the graphics events generated by the devices, under yet another alternative embodiment. This system is but one example of a system comprising multiple running programs (e.g. graphics A-E) and one or more display devices (not shown), in which the graphical output of some or all of the programs is made available to other programs in a coordinated manner using the Plasma constructs (e.g., pools, proteins, and slaw) to allow the running programs to share and collectively respond to the graphics events generated by the devices.

It is often useful for a computer program to display graphics generated by another program. Several common examples include video conferencing applications, network-based slideshow and demo programs, and window managers. Under this configuration, the pool is used as a Plasma library to implement a generalized framework which encapsulates video, network application sharing, and window management, and allows programmers to add in a number of features not commonly available in current versions of such programs.

Programs (e.g., graphics A-E) running in the Plasma compositing environment participate in a coordination pool through couplings and/or connections to the pool. Each program may deposit proteins in that pool to indicate the availability of graphical sources of various kinds. Programs that are available to display graphics also deposit proteins to indicate their displays' capabilities, security and user profiles, and physical and network locations.

Graphics data also may be transmitted through pools, or display programs may be pointed to network resources of other kinds (RTSP streams, for example). The phrase "graphics data" as used herein refers to a variety of different representations that lie along a broad continuum; examples of graphics data include but are not limited to literal examples (e.g., an 'image', or block of pixels), procedural examples (e.g., a sequence of 'drawing' directives, such as those that flow down a typical openGL pipeline), and descriptive examples (e.g., instructions that combine other graphical constructs by way of geometric transformation, clipping, and compositing operations).

On a local machine graphics data may be delivered through platform-specific display driver optimizations. Even when graphics are not transmitted via pools, often a periodic screen-capture will be stored in the coordination pool so that clients without direct access to the more esoteric sources may still display fall-back graphics.

One advantage of the system described here is that unlike most message passing frameworks and network protocols, pools maintain a significant buffer of data. So programs can rewind backwards into a pool looking at access and usage patterns (in the case of the coordination pool) or extracting previous graphics frames (in the case of graphics pools).

Figure 20:
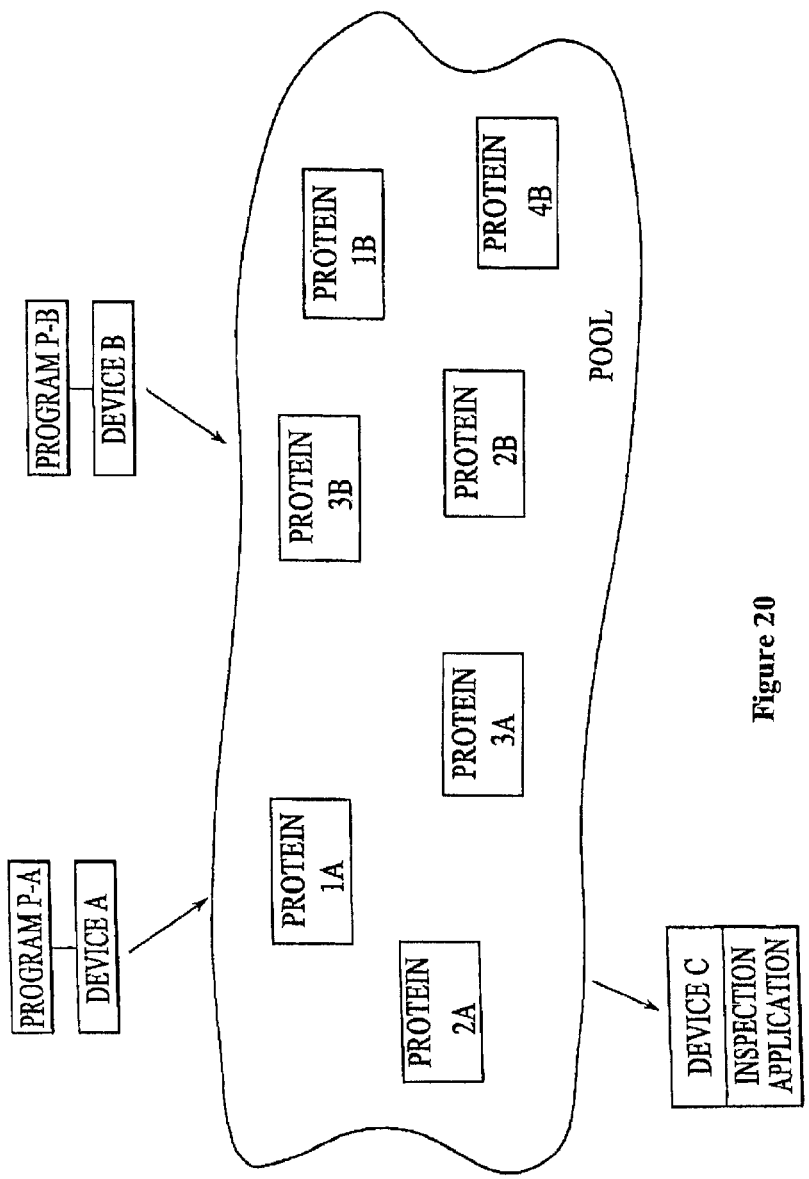
FIG. 20 is a block diagram of a processing environment including multiple devices coupled among numerous programs running on one or more of the devices in which the Plasma constructs (i.e., pools, proteins, and slaw) are used to allow stateful inspection, visualization, and debugging of the running programs, under still another alternative embodiment.

FIG. 20 is a block diagram of a processing environment including multiple devices coupled among numerous programs running on one or more of the devices in which the Plasma constructs (e.g., pools, proteins, and slaw) are used to allow stateful inspection, visualization, and debugging of the running programs, under still another alternative embodiment. This system is but one example of a system comprising multiple running programs (e.g. program P-A, program P-B, etc.) on multiple devices (e.g., device A, device B, etc.) in which some programs access the internal state of other programs using or via pools.

Most interactive computer systems comprise many programs running alongside one another, either on a single machine or on multiple machines and interacting across a network. Multi-program systems can be difficult to configure, analyze and debug because run-time data is hidden inside each process and difficult to access. The generalized framework and Plasma constructs of an embodiment described herein allow running programs to make much of their data available via pools so that other programs may inspect their state. This framework enables debugging tools that are more flexible than conventional debuggers, sophisticated system maintenance tools, and visualization harnesses configured to allow human operators to analyze in detail the sequence of states that a program or programs has passed through.

Referring to FIG. 25, a program (e.g., program P-A, program P-B, etc.) running in this framework generates or creates a process pool upon program start up. This pool is registered in the system almanac, and security and access controls are applied. More particularly, each device (e.g., device A, B, etc.) translates discrete raw data generated by or output from the programs (e.g., program P-A, program P-B, etc.) running on that respective device into Plasma proteins and deposits those proteins into a Plasma pool. For example, program P-A generates data or output and provides the output to device A which, in turn, translates the raw data into proteins (e.g., protein 1A, protein 2A, protein 3A, etc.) and deposits those proteins into the pool. As another example, program P-B generates data and provides the data to device B which, in turn, translates the data into proteins (e.g., proteins 1B-4B, etc.) and deposits those proteins into the pool.

For the duration of the program's lifetime, other programs with sufficient access permissions may attach to the pool and read the proteins that the program deposits; this represents the basic inspection modality, and is a conceptually "one-way" or "read-only" proposition: entities interested in a program P-A inspect the flow of status information deposited by P-A in its process pool. For example, an inspection program or application running under device C can extract one or more proteins (e.g., protein 1A, protein 2A, etc.) from the pool. Following protein extraction, device C can use the data of the protein, retrieved or read from the slaw of the descrips and ingests of the protein, to access, interpret and inspect the internal state of program P-A.

But, recalling that the Plasma system is not only an efficient stateful transmission scheme but also an omnidirectional messaging environment, several additional modes support program-to-program state inspection. An authorized inspection program may itself deposit proteins into program P's process pool to influence or control the characteristics of state information produced and placed in that process pool (which, after all, program P not only writes into but reads from).

Figure 21:
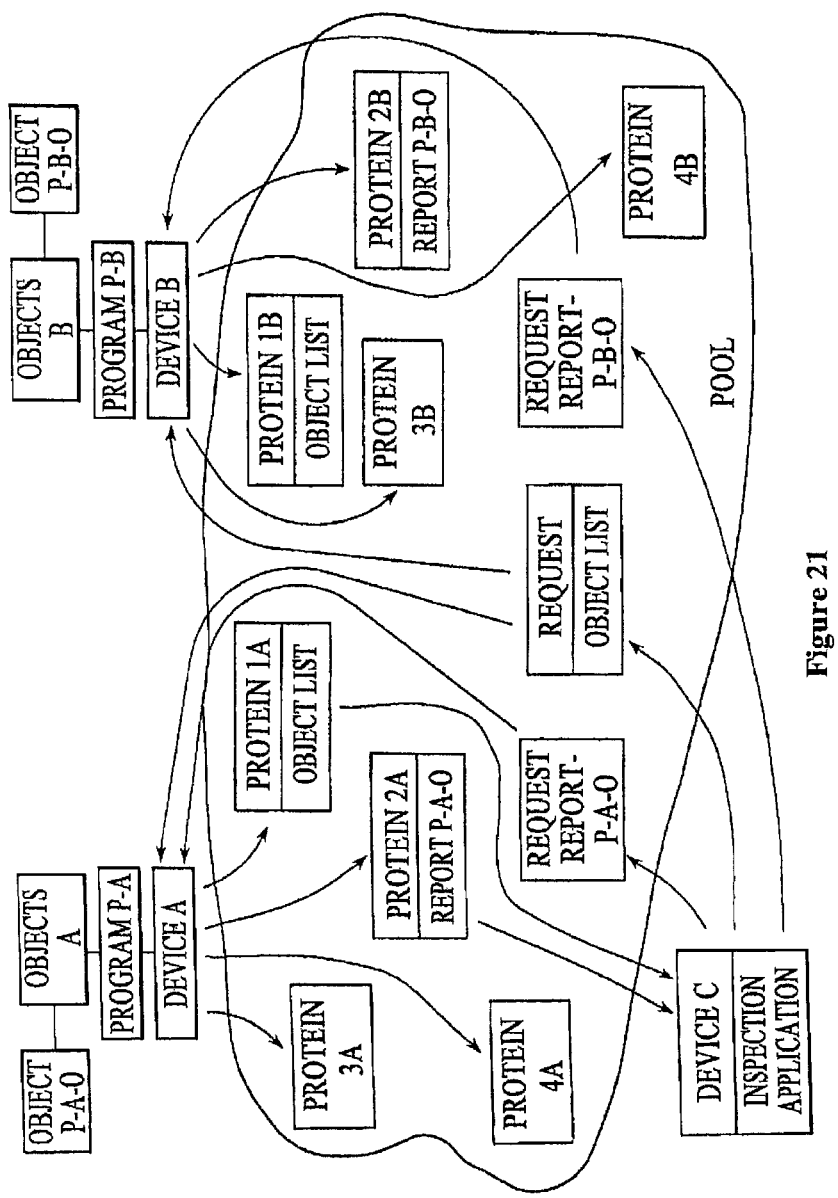
FIG. 21 is a block diagram of a processing environment including multiple devices coupled among numerous programs running on one or more of the devices in which the Plasma constructs (i.e., pools, proteins, and slaw) are used to allow influence or control the characteristics of state information produced and placed in that process pool, under an additional alternative embodiment.

FIG. 21 is a block diagram of a processing environment including multiple devices coupled among numerous programs running on one or more of the devices in which the Plasma constructs (e.g., pools, proteins, and slaw) are used to allow influence or control the characteristics of state information produced and placed in that process pool, under an additional alternative embodiment. In this system example, the inspection program of device C can for example request that programs (e.g., program P-A, program P-B, etc.) dump more state than normal into the pool, either for a single instant or for a particular duration. Or, prefiguring the next 'level' of debug communication, an interested program can request that programs (e.g., program P-A, program P-B, etc.) emit a protein listing the objects extant in its runtime environment that are individually capable of and available for interaction via the debug pool. Thus informed, the interested program can 'address' individuals among the objects in the programs runtime, placing proteins in the process pool that a particular object alone will take up and respond to. The interested program might, for example, request that an object emit a report protein describing the instantaneous values of all its component variables. Even more significantly, the interested program can, via other proteins, direct an object to change its behavior or its variables' values.

More specifically, in this example, inspection application of device C places into the pool a request (in the form of a protein) for an object list (e.g., "Request-Object List") that is then extracted by each device (e.g., device A, device B, etc.) coupled to the pool. In response to the request, each device (e.g., device A, device B, etc.) places into the pool a protein (e.g., protein 1A, protein 1B, etc.) listing the objects extant in its runtime environment that are individually capable of and available for interaction via the debug pool.

Thus informed via the listing from the devices, and in response to the listing of the objects, the inspection application of device C addresses individuals among the objects in the programs runtime, placing proteins in the process pool that a particular object alone will take up and respond to. The inspection application of device C can, for example, place a request protein (e.g., protein "Request Report P-A-O", "Request Report P-B-O") in the pool that an object (e.g., object P-A-O, object P-B-O, respectively) emit a report protein (e.g., protein 2A, protein 2B, etc.) describing the instantaneous values of all its component variables. Each object (e.g., object P-A-O, object P-B-O) extracts its request (e.g., protein "Request Report P-A-O", "Request Report P-B-O", respectively) and, in response, places a protein into the pool that includes the requested report (e.g., protein 2A, protein 2B, respectively). Device C then extracts the various report proteins (e.g., protein 2A, protein 2B, etc.) and takes subsequent processing action as appropriate to the contents of the reports.

In this way, use of Plasma as an interchange medium tends ultimately to erode the distinction between debugging, process control, and program-to-program communication and coordination.

To that last, the generalized Plasma framework allows visualization and analysis programs to be designed in a loosely-coupled fashion. A visualization tool that displays memory access patterns, for example, might be used in conjunction with any program that outputs its basic memory reads and writes to a pool. The programs undergoing analysis need not know of the existence or design of the visualization tool, and vice versa.

The use of pools in the manners described above does not unduly affect system performance. For example, embodiments have allowed for depositing of several hundred thousand proteins per second in a pool, so that enabling even relatively verbose data output does not noticeably inhibit the responsiveness or interactive character of most programs.

Multi-Modal Input Device (MMID)

Numerous embodiments of a multi-modal input device (MMID) are described herein, where the MMID allows the user of a spatial or gestural input system to access a range of input functionalities intuitively and in an ergonomically efficient manner. The MMID of an embodiment, also referred to herein as a wand, is a hand-held input device. The MMID of an embodiment comprises a means of accurately, and in real time, tracking the position and orientation of the device. The MMID of an embodiment comprises a physical and mechanical structure such that the person holding and operating the device may easily rotate it about one or more of its axes. The MMID of an embodiment comprises a physical and mechanical structure such that the device may be held and operated comfortably in more than one rotational grip. The MMID of an embodiment comprises a software component(s) or mechanism capable of interpreting and translating into user input signals both the rotational grip state in which the user is maintaining and operating the device and transitions between these operational rotation states. This software component relies on the tracking data corresponding to the device. In addition, such an input device may have other input capabilities integrated into its form, such as buttons, joysticks, sliders and wheels. The device may also have integrated output capabilities, such as lights, audio speakers, raster displays, and vibrating motors.

As suggested herein, a large variety of specific configurations are possible for the multi-modal input device of the various embodiments. Devices may differ in physical shape, mechanicals, and ergonomics. Devices may also differ in the number of discreet modalities supported by the combination of physical design, tracking technology, and software processing. Furthermore, MMIDs may differ in the design of supplementary on-board input (i.e. beyond position, orientation, and modality), and in on-board output capabilities.

Figure 22:
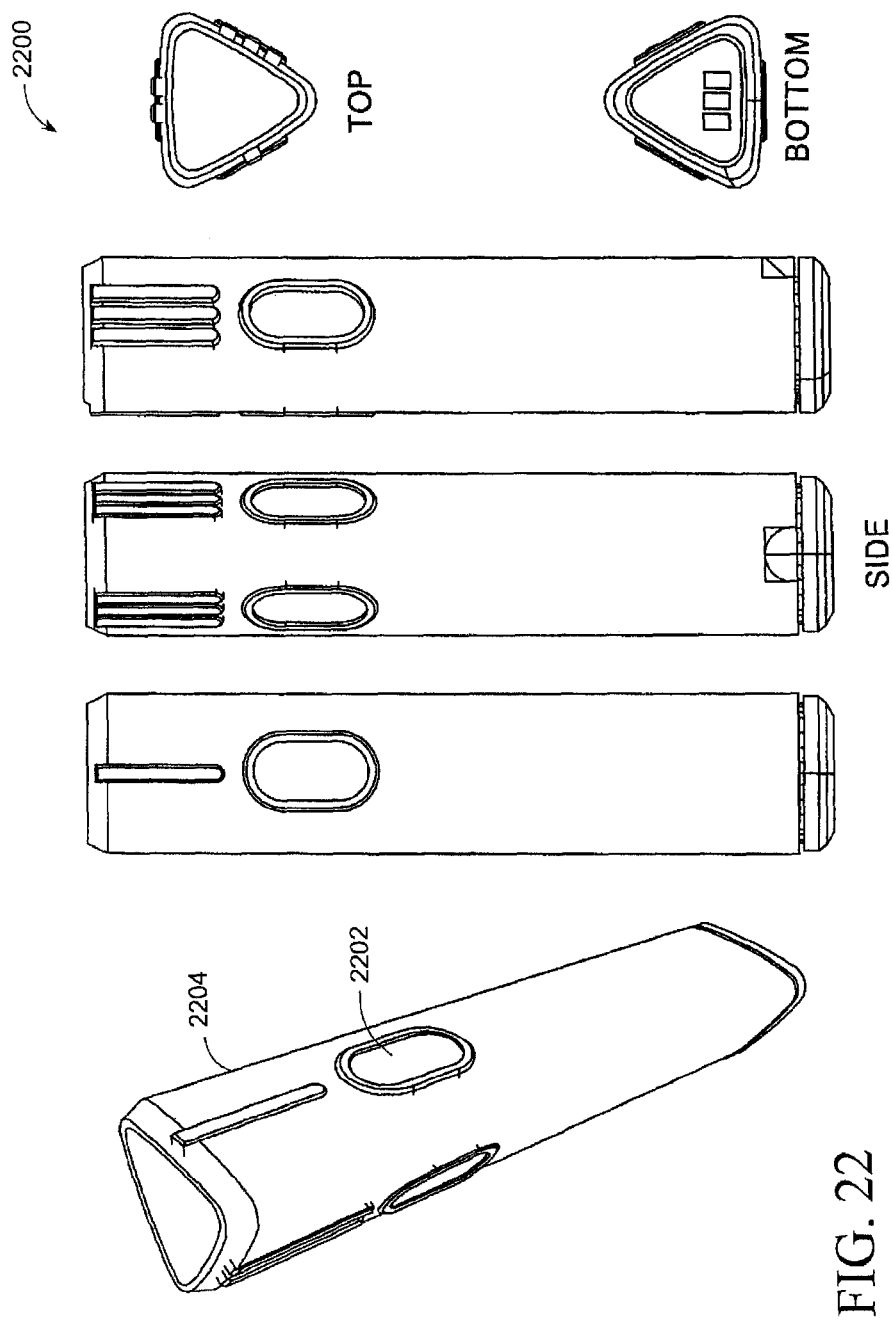
FIG. 22 shows a wand-shaped multi-modal input device (MMID), under an embodiment.

The MMID of an embodiment includes a wand-shaped device with a housing having a form factor similar to a consumer electronics remote control. FIG. 22 shows the wand-shaped MMID 2200, under an embodiment. The MMID 2200 is approximately five inches long and one and one-half inches wide with a triangular cross-section, but is not so limited. Each face of the MMID 2200 housing includes a single input sensor, which in an embodiment comprises an electro-mechanical button, but alternative embodiments can have a greater or lesser number of buttons, or different types of buttons, on each face. When a user holds the MMID 2200 one of the triangular prism's long edges 2204 naturally faces downward in the user's hand, resting in the bend of the user's fingers, while the prism's opposite face is oriented upward and sits under the user's thumb. The MMID 2200 may be rotated 2220 degrees about the long axis with a minimal movement of the fingers and thumb, bringing an adjacent face of the prism into the upward orientation. The prism thus includes three distinct, easily accessed modal orientations corresponding to the faces of the prism. The MMID 2200 can be rotated through all (e.g., three) orientations rapidly, repeatably and repeatedly, even by users experimenting with the device for the first time.

Position of the MMID 2200 of an embodiment is tracked using magnetic field tracking, as described below, but can be tracked using other tracking technologies (some of which are described herein). The MMID 2200 comprises circuitry, a microcontroller, and program code for tracking the device relative to an alternating current (AC) magnetic field, or electromagnetic field (EMF). The EMF of an embodiment is generated or emitted by a compatible base station proximate to the MMID, but is not so limited. The MMID 2200 comprises one or more mechanical buttons, also referred to as input sensors, along with corresponding electronics to digitize the state of the one or more buttons. Furthermore, the MMID 2200 includes circuitry that provides a radio link to report the tracking data (e.g., orientation data, position data, etc.) and button press raw data to a host system. Additionally, the MMID 2200 includes a battery and power supply circuitry.

Input processing software translates the raw tracking and button press data into data comprising six degrees of spatial position and orientation, button down transition, button up transition, and a running account of button state. The input processing software of an embodiment executes in part on the device and in part as application code on the host system, but is not so limited and can run in a distributed manner on any number and/or combination of processing devices or solely on a single processor. This data is delivered to application software as a series of programmatic "events" (processing of the programmatic events is described in detail below). In addition, this input processing layer provides mode transition and running mode state events to application software. Three states (e.g., i, ii, and iii), and six transitions (e.g., i→ii, i→iii, ii→iii, ii→i, iii→i, and iii→ii) are possible, as described in detail below.

The processing layer of an embodiment uses hysteresis to allow a user to access a maximum of rotation along the MMIDs long axis without leaving a given mode, and to avoid rapid, undesirable flip-flopping between modal states when the MMID is near the edge of a transition angle. Using this hysteresis, to trigger a transition between modes, the MMID of an embodiment should be rotated more than 120 degrees relative to the center angle of the previous mode. So if the MMID is in mode (i), with an absolute angular center of zero degrees, the MMID remains logically in the mode (i) state until a rotation is detected about the long axis of more than, say, 150 degrees in either direction. When the MMID is rotated 151 degrees, it transitions to modal state (ii), which has an angular center of 120 degrees. To effect a return to state (i) the MMID must be rotated in the opposite sense past this angular center by −150 degrees, bringing it past an absolute angle of −30 (or 330) degrees. The hysteresis band, given above as 30 degrees (150 degrees minus 120), is programmatically settable, and may be adjusted by application code or by user preference setting. This hysteresis example if provided for a three-sided MMID, as described above, but is not limited to the values described herein for the three-sided device; the rotation angles and/or hysteresis bands of alternative embodiments are determined according to a form-factor of the housing or wand and to designer/user preferences.

In addition, certain modes can be selectively disabled by application code. So the MMID can be treated by application code as a single-mode device outputting a constant modal state of (i), (ii), or (iii). Or, any one of the modes may be disabled, either by mapping the disabled mode to either of the two remaining modes exclusively, or by treating the disabled mode as an additional area of the hysteresis band.

Further, the system may be configured to immutably associate a physical face of the MMID (e.g., triangular prism) with each mode, the faces being optionally labeled as to mode association by means of active or passive markings. Alternatively, the system may be configured to assign modes to faces in a contextual way. As an example of this latter case, the MMID can be configured so that, when it is first picked up by a user after a period of inactivity, the initially upward face is associated with mode (i). In such cases an indicator of the active mode can be provided on the MMID, on the graphical display to which the user is attending, or on a combination of the MMID and the graphical display.

Each face of the MMID includes a single button, also referred to as an input sensor. These buttons are treated identically by application-level software, but are not so limited. From the user's perspective, the device may be considered as having a single logical button, with three physical incarnations for reasons of ergonomic practicality. The circuitry and software of the MMID does distinguish manipulation of different physical buttons, however, and the system may be arranged so that pressing the buttons in specific combinations places the device in various configuration and reset states.

The MMID of an embodiment functions using magnetic field tracking technology (see, for example, U.S. Pat. No. 3,983,474). The use of orthogonal coils for generating and sensing magnetic fields has been used in locating and tracking remote objects. For example, U.S. Pat. No. 3,644,825 teaches generating and sensing coils which move with respect to each other. Alternatively, the magnetic field can be made to rotate as taught in Kalmus, "A New Guiding and Tracking System", IRE Transactions on Aerospace and Navigational Electronics, March 1962, pages 7 through 10.

The use of coordinate transformers to determine the orientation of a first coordinate system with respect to a second coordinate system has also been used. For example, U.S. Pat. Nos. 3,474,241 and 3,660,648 disclose transformers which transform angular rates or angular errors measured in a first coordinate frame into angular rates defined about the axes of an intermediate coordinate frame about whose axes the angular rotations or rates are defined and then integrate to determine the angles defining the angle-axis sequence which defines the orientation of the first coordinate frame with respect to a second coordinate frame through the use of Euler angles.

Figure 23:
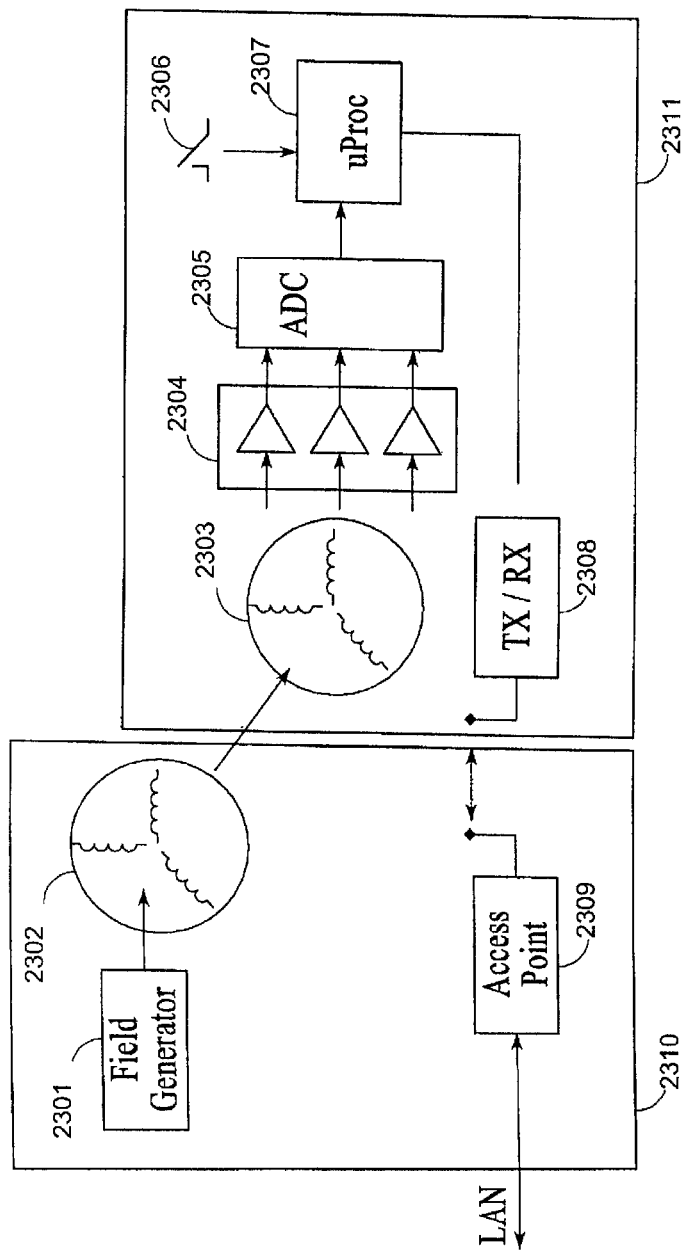
FIG. 23 is a block diagram of a MMID using magnetic field tracking, under an embodiment.

FIG. 23 is a block diagram of a MMID using magnetic field tracking, under an embodiment. A base station 2310 located proximate or in the tracking environment of the MMID both provides the tracking field, as well as communicates with the MMID 2311. In the base station, a signal generator creates magnetic fields by using a field generator circuit 2301 to produce a wave form alternately in three orthogonal coils 2302. The electromagnetic signals generated by these coils are received by three orthogonal coils 2303 in the MMID. The received signals from the three coils are typically amplified using operational amplifiers 2304 and converted to digital signals 2305 which can be sampled by a microprocessor 2307. The microprocessor analyzes the input of the three coils using digital signal processing (DSP) techniques. The DSP process provides a location vector projecting the distance and direction of the MMID from the base station, as well as an orientation matrix that determines the orientation of the MMID.

Additional information (e.g., time stamp, universal ID, etc.) can also be combined with the MMID location data. One or more user input sensors 2306 are also sensed for state. The input sensors 2306 can be momentary switches, toggle switches, joystick style input devices, and/or touch sensors to name a few. The sample data from these switches includes a single bit (for a touch button) or a more complex data value, such as a floating point x,y coordinate for a touch sensor.

In an embodiment, the microprocessor communicates data including location data and orientation data from the MMID wirelessly to a host process. The MMID has a radio frequency transmitter and receiver (TX/RX) 2308 for data communication to the network through an Access Point 2309. This radio link can use any wireless protocol (e.g., Bluetooth, 802.11, Wireless USB, proprietary solutions, Nordic Semiconductor nRF24L01 low power radio solution, etc.). The access point can communicate the received data stream to one or more host computers through a local area network (e.g., Wired Internet 10/100/1000BaseT, 802.11, etc.) or other interface (e.g., USB, etc.).

Figure 24:
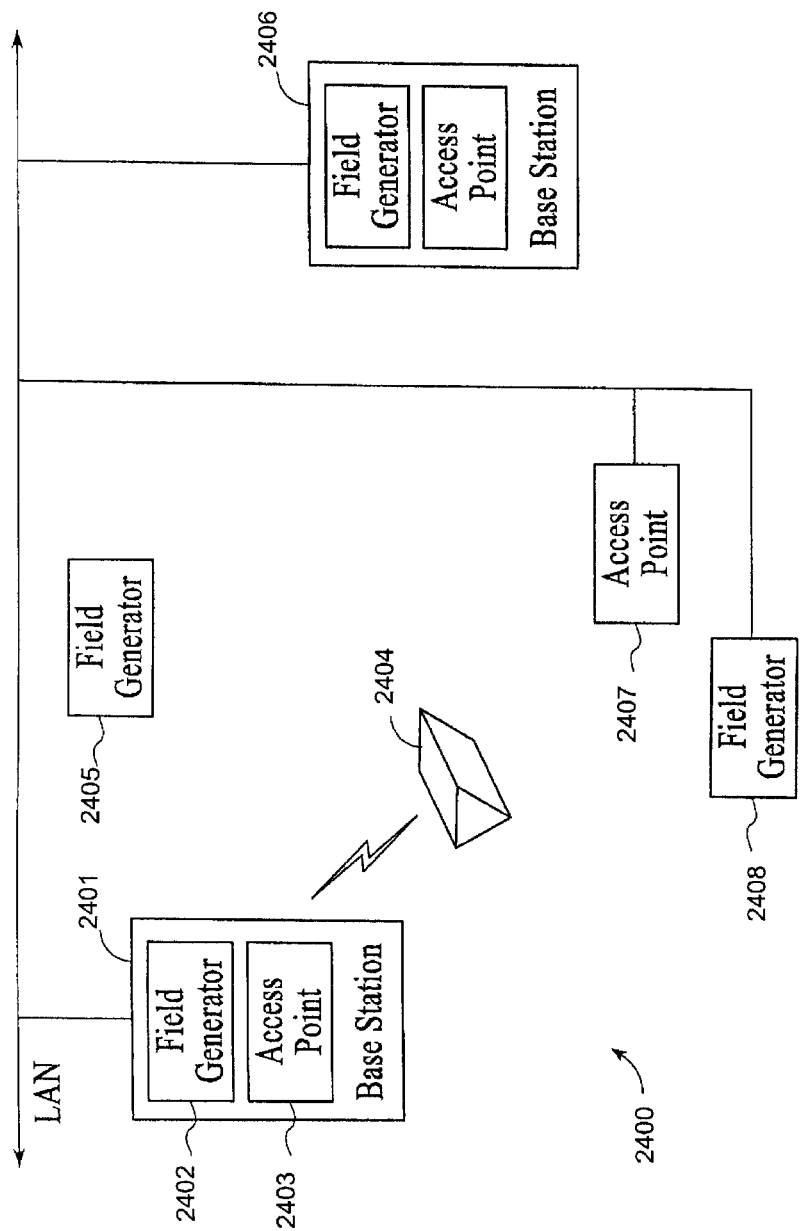
FIG. 24 is a block diagram of the MMID in a tracking environment, under an embodiment.

FIG. 24 is a block diagram of the MMID in a tracking environment, under an embodiment. The MMID 2404 is shown in relation to the tracking environment 2400. The MMID is communicating with a base station 2401, as described above, but the MMID can communicate with any number of different types and/or combinations of electronic devices in the tracking environment 2400. The tracking environment is not limited to a particular size because, as the range of the radio frequency communications channel may be different from the range of the AC magnetic field, additional AC magnetic field generators 2405/2406/2408 with coils can be provided to create additional tracking beacons. These beacons can operate at different frequencies and/or transmit at different times. As the user of the MMID moves away from field generator 2402 and towards generator 2405 the MMID will use whichever signal is instantaneously stronger to determine location and orientation, but will still communicate this data back to the network using access point 2403.

As the MMID moves out of range of the access point 2403 and towards base station 2406, the MMID will associate the radio link with the access point in base station 2406. The ability to roam among magnetic field generators and data access points ultimately allows the MMID to be used in an arbitrarily large tracking environment. Note that the access points and magnetic field generators need not be at the same location 2407/2408. While both the access points and field generators have means of communication with one or more host devices over a local area network, the frequency generators can operate autonomously 2405 allowing for easier installation.

Following is an operational example of a person using the MMID of an embodiment. During operation, an operator stands some distance (e.g., ten feet) before a triptych-format wide aspect ratio projection screen, roughly two meters high and four meters wide; a one-point-five meter wide table stands immediately before her. The table is itself also a projection surface treated by a projector ceiling-mounted immediately overhead. The operator holds the MMID having the triangular-cross-section MMID comfortably in her right hand, with flat side "i" pointing upward. As she aims the MMID toward and about the front screen, a partially transparent graphical cursor indicates the intersection of the MMIDs pointing vector with the screen surface. The input system's high frame rate and low latency contribute to a strong sense of causal immediacy: as the operator changes the MMIDs aim, the cursor's corresponding movement on the forward screen does not apparently lag behind; the perception is of waving a flashlight or laser pointer.

The application in use by the operator is a product packaging preview system, and is configured to make use of the MMID in a way identical to many similar applications; the MMID modalities are thus well familiar to the operator. Mode "i" allows direct manipulation of application elements at the fully detailed level; mode "ii" performs meta-manipulation of elements (e.g. at the group level); and mode "iii" permits three-dimensional manipulations. At any instant, the appearance of the cursor reflects not only the current mode but also indicates visually the direction of axial rotation that would be necessary to switch the MMIDs modes. At present, the cursor shows that a clockwise rotation of the MMID would cause a modal transition to "ii", while counterclockwise rotation would transition to mode "iii".

Arranged on the left third of the forward screen triptych is an array of small object groupings. The operator rotates the MMID axially clockwise until the next face is aimed upward, under her thumb, and the cursor changes to indicate the modal transition to state "ii". She aims the MMID leftward, and as the cursor travels over each object grouping a highlight border fades up, subsequently fading down as the cursor exits the grouping's convex hull. The operator allows the cursor to rest on a particular grouping and then depresses the button immediately under her thumb. The cursor indicates that the object grouping has been grabbed and, as she swings the MMID toward the center of the forward screen, the grouping moves so as to track along with the cursor. The operator releases the button when she has brought the miniature grouping to a position directly in front of her. The grouping rapidly expands to fill the full extent of the center third of the forward screen, revealing a collection of variously shaped plastic bottles and the textual indication "Pet Energy Beverages".

The operator once again rotates the MMID clockwise about its long axis, whereupon the cursor changes to indicate that mode "iii" is now operational and, thus, that 3D manipulation is enabled. The operator aims the cursor at a particularly bulbous bottle shaped like a coiffured poodle leg, and the bottle visually highlights; the operator then depresses the button. The system now enters a direct-manipulation mode in which translation and rotation of the MMID controls translation and rotation of the selected object in the virtual space being rendered. So, as the operator pulls the MMID toward herself (directly along the geometric normal to the forward screen), the bottle grows larger, verging toward the virtual camera. Similarly, left-right movement of the MMID translates to left-right movement of the rendered bottle (along the screen's lateral axis), and up-down translation of the MMID results in vertical translation of the bottle. An appropriate scale factor, customizable for each operator, is applied to these translations so that modest movements of the MMID effect larger movements of virtual objects; the full extent of the graphical/virtual environment is thereby made accessible without exceeding an operator's range of comfortable hand-movement.

A similar scaling function is applied to the mapping of MMID orientation to absolute rotational position of the rendered bottle. In the present example, the operator's preferences dictate a four-times scale, so that a ninety degree rotation of the MMID around any axis results in a full three hundred sixty degree rotation of the virtual object (90 degrees multiplied by four (4) results in 360 degrees). This insures that wrist- and arm-based MMID rotations remain within a comfortable range as the operator examines the bottle from every possible angular vantage. So, for example, as she rotates the MMID upward, tipping it ninety degrees around a local x-axis so that it evolves from forward-pointing to upward-pointing, the bottle executes a full rotation around the screen-local x-axis, returning to its initial orientation just as the MMID achieves a fully upward attitude. Note that an appropriate mode-locking effect is applied so long as the MMIDs button remains depressed: the operator may rotate the MMID one hundred seventy clockwise degrees around the MMIDs long axis (producing a five hundred ten degree "in-screen" rotation of the virtual object) without causing the MMID to switch to mode "i".

When the operator releases the MMIDs button, the rendered bottle is released from direct manipulation and retains its instantaneous position and rotation. If at the moment of button release the MMID is in a rotational attitude that would ordinarily correspond to a MMID-mode other than "iii", the operator is granted a one-second temporal hysteresis (visually indicated as part of the on-screen cursor's graphical state) before the mode switch is actually effected; if the operator returns the MMID rotationally to an attitude corresponding to mode "iii", then direct 3D manipulation mode persists. She may then perform additional positional and attitudinal adjustments by superimposing the cursor atop the bulbous bottle and again depressing the button; if instead she aims the cursor at a different bottle, that object will be subject to her manipulations.

The operator eventually switches the MMID to mode "ii" and, using a dragging modality identical to that by which she brought the bottle grouping to the center screen, brings a color-palette from the right screen to the center screen; when she releases the button, the palette expands and positions itself to the side of the bulbous bottle. She then rotates the MMID to select mode "i" and manipulates the color palette's selection interface; when the crimson hue she desires has been selected, she depresses the button and drags a color swatch from the palette downward and leftward until it overlies the clear material forming the bulbous bottle. When she releases the button, the color is applied and the bottle's material adopts a transparent crimson.

Still in mode "i", the operator points the MMID directly at the bulbous bottle, which highlights in response, and, depressing the button, swings the MMID downward to drag the image of the bottle from the front screen to the surface of the table immediately before her. She releases the button and thereby the bottle, leaving it in position on the table. The operator then rotates back to mode "ii" and points the MMID forward at the collection of other pet energy beverage bottles; she depresses the button and immediately flicks the MMID leftward, releasing the button a fraction of a second later. The collection of bottles flies leftward, diminishing in size as it travels, until it comes to rest in the location and at the overall scale at which it started. The operator then selects a different grouping of pet care products, bringing it to the center display region as before in order to select, inspect, and modify one of the items. She eventually adds the selected object to the table display. The operator continues this curatorial process.

At a certain point, the operator elects to modify the physical geometry of a canister of pet massage oil using a simple geometry editor, also pulled from the collection of tools appearing on the right third of the forward screen triptych. The description of many manipulations involved in the use of this editor is omitted here, for the sake of clarity, except as regards the simultaneous use of two MMIDs. In the present instance, the operator uses a second MMID, held in her left hand, in order to put a twist in the canister (originally a simple extruded shape with rectangular cross section) by using one MMID to grab the top part of the canister's geometry and the other MMID to grab the canister's bottom part (both MMIDs in mode "iii"). With the top and bottom thereby separately "affixed", the operator rotates the MMIDs in opposite directions; this introduces a linear twist about the canister's main axis. The operator finishes these geometry modifications and returns the editing module to the right display; she adds the modified canister to the table's growing assortment.

At last there are a dozen objects being rendered on the table, and the forward center display is empty once more—the operator has mode-"ii"-flicked the last grouping leftward (and the color palette rightward). She then points the MMID, still in mode "ii", at the table, but her aim avoids the product renderings there; instead, she depresses the right button and describes a circular trajectory with the MMID, as if drawing a curved corral shape around the displayed objects. In response, the system applies a grouping operation to the formerly distinct product renderings, organizing their layout and conforming their relative sizes. Finally, the operator uses mode-"ii"-dragging to elastically extend the input aperture of a graphical "delivery tube" from the right display to the center; she then picks up the table's customized product collection, drags it up to the center screen, and deposits it in the mouth of the delivery tube. The tube ingests the collection and retracts back to the right display; the collection will be delivered to the operator's colleague, who is expecting to review her work and use it to construct an interactive visualization of a pet shop aisle.

The MMID of an alternative embodiment includes a housing having a rectangular form-factor. The pointer of this alternative embodiment is five inches long, one and one half inches wide, and one half inch deep, for example, but many other sizes and/or configurations are possible hereunder. The MMID includes optically tracked tags, described in detail below. The MMID does not include electronics as the processing software runs in a host system environment, but the embodiment is not so limited.

A user most naturally holds the pointer such that the long axis serves to point at objects (including virtual objects) in the user's environment. The pointer can be rotated around the long axis to transition between two modal orientations (e.g., modes i and ii). Four modal transitions are possible, even though there are only two modes, because the system can distinguish between the direction of rotation during a transition: transition from mode i to mode ii/clockwise; transition from mode i to mode ii/counter-clockwise; transition from mode ii to mode i/clockwise; transition from mode ii to mode i/counter-clockwise. As with the MMID described above, these rotational transitions are tracked in input processing software, and can be subject to hysteretic locking.

The optical tags are mounted on the "front" portion (e.g., front half) of the pointer, in the area extending outwards from the user's hand, for example, but are not so limited. On each of the two sides of the pointer, two tags are mounted. The forward-most tag on each side is fixed in position. The rear-most tag on each side is positioned a distance (e.g., five (5) centimeters) behind the forward tag and is aligned along and oriented according to the same axis. This rear tag is affixed to a spring-mounted sliding mechanism (the direction of translation aligned with the pointer's long axis) such that the user's thumb may push forward on the mechanism to decrease the distance between the two tags by approximately one centimeter.

The input processing software interprets the logical button state of the device to be in state (0) when the distance between the two tags is five centimeters. To effect a transition to state (1), the rear tag is moved a distance closer to the front tag (e.g., to within 4.2 centimeters of the front tag). The transition back to button state (1) is triggered only when the distance between the tags exceeds 4.8 centimeters. This is similar to the hysteresis applied to the device's principal (rotational) mode transitions. Again, the size of the hysteresis band is configurable.

In the embodiment of an optically tracked MMID, an optical tracking tag is used where a number of dots are aligned on a tag. These dots may be small spheres covered with retroreflectors, for example, allowing an IR tracking system (described below) to determine the location and orientation of a tagged object. In the case that this tagged object is an input MMID, it may be desired to provide a means for the tracking system to determine when a user has provided a non-geometric, state-change input, such as pressing a button.

Figure 25A:
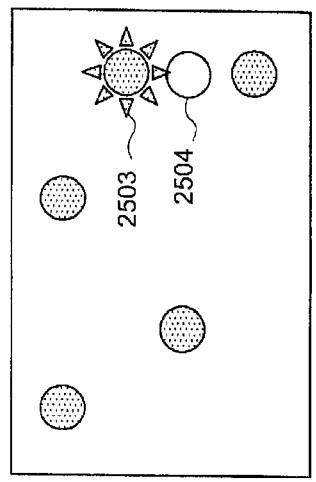
FIGS. 25A and 25B show input states of the MMID with infrared (IR) light-emitting diodes (LEDs) (IR LEDs), under an embodiment.
Figure 25B:
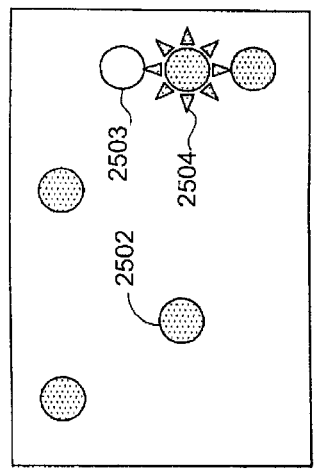

The MMID of various alternative embodiments operates using infrared (IR) light-emitting diodes (LEDs) (IR LEDs) to provide tracking dots that are only visible to a camera at certain states based on the user input. The MMID of these alternative embodiments includes a battery and LED driving circuitry controlled by the input button. FIGS. 25A and 25B show input states of the MMID with IR LEDs, under an embodiment. The tag of this embodiment comprises numerous retro-reflective dots 2502 (shown as a solid filled dot) and two IR LEDs 2503 and 2504. In FIG. 25A, the tag is shown in a state in which the button on the MMID is not pressed, and IR LED 2503 is in the non-illuminated state, while IR LED 2504 is in the illuminated state. In FIG. 25B, the user has pressed a button on the MMID and, in response, IR LED 2503 is in the illuminated state while IR LED 2504 is in the non-illuminated state. The optical processing system detects the difference in the two tags and from the state of the two tags determines the user's intent.

Figure 26A:
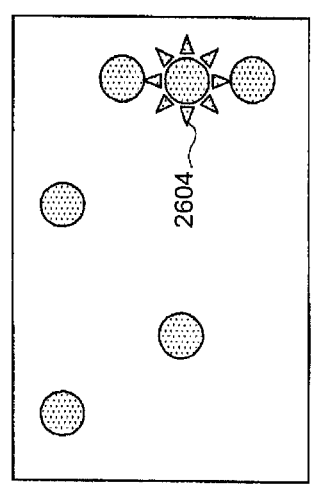
FIGS. 26A and 26B show input states of the MMID with IR LEDs, under an alternative embodiment.
Figure 26B:
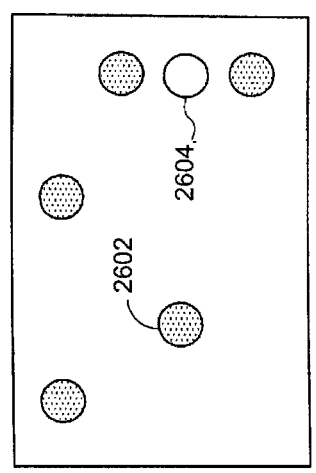

FIGS. 26A and 26B show input states of the MMID with IR LEDs, under another alternative embodiment. In this embodiment, only one LED is switched. Thus, referring to FIG. 26A, LED 2604 is in the non-illuminated state when the user has not pressed the button. In FIG. 26B, the user has pressed the button and LED 2604 is thus illuminated.

Additional methods are also enabled using similar approaches. In one alternative embodiment, a complete tag is constructed using LEDs and the presence or absence of that tag provides input of the user. In another embodiment, two identical tags are created either overlaid (offset by, for example 0.5 cm) or adjacent. Illuminating one tag or the other, and determining the location of that tag with respect to another tag, allows the input state of the user to be determined.

The MMID of other alternative embodiments can combine the use of tag tracking with EMF tracking. These alternative embodiments combine aspects of the EMF tracking with the tag tracking using various types of tags, as described herein.

The MMID of another alternative embodiment includes a controller used in conjunction with two infrared light sources, one located in front of the user and one positioned behind the user. These two light sources each have three individual infrared emitters, and the emitter of each source is configured in a different pattern. The MMID of this embodiment makes use of inertial tracking, includes two modes, and includes multiple mechanical input buttons, as described below.

The MMID of this embodiment might be thought of as a modification of a Nintendo® Wii™ remote control device that supports two modal orientations, with the modes determined by the directional orientation of the controller relative to its environment. The Wii™ controller is a small device used to play video games on the Nintendo® Wii™ platform, and an associated infrared light source. The controller tracks its motion in space inertially, using a set of low-accuracy accelerometers. The accelerometers are not accurate enough to provide good position and orientation data over more than a few tenths of seconds, because of the errors that accumulate during numerical integration, so an optical tracking system (in conjunction with the light source component) is also used. The optical tracking system of the Wii™ controller therefore further comprises an internal, front-facing infrared camera capable of locating four bright infrared light sources in a two-dimensional image plane. Therefore, the camera is embedded in the tracked device and the objects that are optically located are fixed-position environmental referents. By measuring the perceived size and position of known infrared light sources in the environment it is possible to determine the direction in which the controller is pointing and to triangulate the controllers distance from those sources. This infrared tracking technology may be viewed as an inversion of the tracking technology described herein, because the infrared tracking technology of the embodiment herein uses cameras placed in the environment to optically locate points arranged on devices, surfaces, gloves, and other objects.

In a typical use with the Nintendo® Wii™ console, the controller is always pointing towards a display screen. An infrared light source is placed above or below the display screen, providing the controller with a screen-relative orientation. In contrast, the controller of an embodiment is used in conjunction with two infrared light sources, one positioned in front of the user and one positioned behind the user. These two light sources each have three individual infrared emitters, and each source's emitters are configured in a different pattern.

The controller of an embodiment communicates by bluetooth radio with input processing software or components running on a host computer. The input processing software identifies which emitter pattern is detected and therefore whether the controller is pointing forwards or backwards. Two modal orientations are derived from this forwards/backwards determination. In modal state (i) the controller is oriented forwards. In modal state (ii) the controller is oriented backwards. In each case, the user is logically pointing forwards. The user controls the mode by turning the controller around "back to front". This is in contrast to the embodiments described above, in which the mode control is a long-axis "rolling" of the device. The controller of an embodiment can include an embedded speaker, providing sound output, several lights, and a vibration (or "rumble") output.

Numerous modifications of the embodiments described herein are possible under this description. The controller of an embodiment may, for example, have two cameras, one on each end of the device, thereby obviating the need for two light sources. The light sources may be differentiated by timing, rather than spatial, patterns.

Embodiments described herein include a system comprising a plurality of tags affixed to a plurality of objects. The plurality of tags includes a plurality of features such that each tag comprises at least one feature. The system includes a plurality of sensors. A location of the plurality of sensors defines a spatial operating environment (SOE) that includes the plurality of objects. The plurality of sensors detects the plurality of features. The system includes an adaptive tracking component (ATC) running on a processor. The ATC receives from each sensor of the plurality of sensors feature data corresponding to each object of the plurality of objects detected by the respective sensor. The ATC generates and maintains a coherent model of relationships between the plurality of objects and the SOE by integrating the feature data from the plurality of sensors.

Embodiments described herein include a system comprising: a plurality of tags affixed to a plurality of objects, wherein the plurality of tags include a plurality of features such that each tag comprises at least one feature; a plurality of sensors, wherein a location of the plurality of sensors defines a spatial operating environment (SOE) that includes the plurality of objects, wherein the plurality of sensors detect the plurality of features; and an adaptive tracking component (ATC) running on a processor, wherein the ATC receives from each sensor of the plurality of sensors feature data corresponding to each object of the plurality of objects detected by the respective sensor, wherein the ATC generates and maintains a coherent model of relationships between the plurality of objects and the SOE by integrating the feature data from the plurality of sensors.

The coherent model includes spatial relationships between the plurality of objects.

The coherent model includes at least one of location, orientation, and motion of the plurality of objects.

The coherent model includes location, orientation, and motion of the plurality of objects.

The SOE comprises virtual space of the ATC, wherein the ATC generates coincidence between the virtual space and physical space that includes the SOE.

A sensor detects from at least one tag a pose comprising location and orientation of the at least one tag relative to the sensor.

The pose comprises a six-degree-of-freedom (DOF) pose.

The plurality of objects include at least one of a body, an appendage of a body, a device, an article of clothing, a glove, a display device, a piece of furniture.

An origin of the coherent model is defined relative to a particular sensor of the plurality of sensors.

An origin of the coherent model is defined relative to a particular tag of the plurality of tags, wherein the particular tag has a fixed pose relative to the SOE.

An origin of the coherent model is defined relative to a particular sensor of the plurality of sensors and a particular tag of the plurality of tags, wherein the particular tag has a fixed pose relative to the SOE.

Each tag of the plurality of tags comprises at least one feature that is detected and localized by the plurality of sensors.

Each tag includes labeling information.
Each tag includes identity information.
Each tag includes pose information.

Each tag includes at least one of labeling information, identity information, and pose information.

Each tag includes labeling information, identity information, and pose information.

A projective image of a tag includes labeling.

The at least one feature comprises at least one marker.

The labeling relates at least one point in the projective image to at least one corresponding marker.

A projective image of a tag includes identity.

The at least one feature comprises a plurality of markers on the tag.

The identity distinguishes a first tag of the plurality of tags from a second tag of the plurality of tags.

A projective image of a tag includes pose information.

The pose information includes translation information and rotation information.

The translation information includes a three-degree-of-freedom translation.

The rotation information includes a three-degree-of-freedom rotation.

The pose information relates a position and orientation of a tag to a position and orientation of the SOE.

Each sensor corresponds to a sensing volume in the SOE.

Each sensor estimates a pose of each tag within the sensing volume.

The pose comprises location of a tag.
The pose comprises orientation of a tag.
The pose comprises location and orientation of a tag.

The location and the orientation are relative to each respective sensor.

The sensing volume of each sensor at least partially overlaps with the sensing volume of at least one other sensor of the plurality of sensors.

A combined sensing volume of the plurality of sensors is contiguous.

The feature data is synchronized.

The ATC generates for each sensor of the plurality of sensors a pose model of a pose relative to the SOE.

The pose comprises a six-degree-of-freedom (DOF) pose.

When a plurality of sensors all detect a first tag at an instant in time, the ATC generates a spatial relationship between the plurality of sensors.

The ATC updates the coherent model using the spatial relationship.

The ATC defines an origin of the coherent model relative to a particular sensor of the plurality of sensors.

The ATC defines an origin of the coherent model relative to a particular tag of the plurality of tags, wherein the particular tag has a fixed pose relative to the SOE.

The ATC defines an origin of the coherent model relative to a particular sensor of the plurality of sensors and a particular tag of the plurality of tags, wherein the particular tag has a fixed pose relative to the SOE.

Correct pose models are determined for each sensor.

A tag is tracked by a sensor at a plurality of points in time and a plurality of pose models are generated for the tag.

A plurality of confidence metrics are generated for the plurality of pose models and the plurality of pose models are culled based on the plurality of confidence metrics to remove any inconsistent pose models.

A tag is tracked by a plurality of sensors at a plurality of points in time and a plurality of sets of pose models are developed for the tag, wherein each set of pose models comprises a plurality of pose models corresponding to each point in time.

A plurality of confidence metrics are generated for the plurality of pose models of each set of pose models, and the plurality of sets of pose models are culled based on the plurality of confidence metrics to remove any inconsistent pose models.

An average hypothesis comprises an average of the plurality of pose models of each set of pose models.

The average hypothesis approximates a maximum likelihood estimate for a true pose of a corresponding tag.

The average hypothesis comprises a positional component.

The average hypothesis comprises a rotational component.

The average hypothesis comprises a positional component and a rotational component.

The positional component is given by a first equation $$x_{avg}(t_n) = \frac{1}{m}[x_1(t_n) + x_2(t_n) + \ldots + x_m(t_n)]$$

where $t_n$ is a point in time at which the hypotheses $x_i \in \mathbb{R}^3$ are measured, and m is a number of sensors detecting the tag at a point in time.

The rotational component is approximated by applying the first equation to unit direction vectors that form a basis of a rotating coordinate frame within the SOE, and re-normalizing the unit direction vectors.

A smoothed hypothesis is generated through application of a correction factor to the average hypothesis.

The smoothed hypothesis is generated when at least one additional sensor detects a tag, wherein the at least one additional sensor has not previously detected the tag.

The smoothed hypothesis is generated when at least one sensor of the plurality of sensors ceases detecting a tag, wherein the at least one additional sensor has previously detected the tag.

The smoothed hypothesis comprises a positional component.

The smoothed hypothesis comprises a rotational component.

The smoothed hypothesis comprises a positional component and a rotational component.

The positional component is given by a second equation $$x_{sm}(t_n, t_{n-1}) = \frac{1}{m}[x_1(t_n) + c_1(t_{n-1}) + x_2(t_n) + c_2(t_{n-1}) + \ldots + x_m(t_n) + c_m(t_{n-1})]$$

where $t_n$ is a point in time at which the hypotheses $x_i \in \mathbb{R}^3$ are measured, m is a number of sensors detecting the tag at that instant, and c is a correction factor.

The correction factor is applied to the average hypothesis, wherein the correction factor is a vector defined as $$c_i(t_n, t_{n-1}) = k(x_{avg}(t_n) - x_i(t_n)) + (1-k)(x_{sm}(t_{n-1}) - x_i(t_{n-1}))$$

where k is a constant selected between 0 and 1.

A value of the constant k is selected to provide the coherent model with relatively high accuracy when an object having a tag affixed undergoes fine manipulation and coarse motions.

The constant k is selected to be much less than 1.

The constant k is selected so that a corrected hypothesis $x_i + c_i$ is relatively close to the smoothed hypothesis.

The constant k is selected to be greater than zero to ensure that the smoothed hypothesis is forced towards the average hypothesis at each time period.

A value of the constant k is varied so that when a motion of the tag is large between time periods the smoothed hypothesis is relatively spatially accurate.

When a motion of the tag is small between time periods, a value of the constant k is selected to be relatively small so that the smoothed hypothesis maintains relatively greater spatial and temporal smoothness.

The rotational component is approximated by applying the second equation to unit direction vectors that form a basis of a rotating coordinate frame within the SOE, and re-normalizing the unit direction vectors.

At least one sensor of the plurality of sensors measures in real-time object poses of at least one object of the plurality of objects.

The at least one sensor comprises a plurality of sensors affixed to an object.

The at least one sensor is affixed to the at least one object.

The ATC automatically adapts to changes in the object poses.

The ATC generates a model of a pose and a physical size of the at least one object.

The pose comprises a six-degree-of-freedom (DOF) pose.

The at least one sensor is affixed to at least one location on a periphery of the at least one object, wherein the at least one object is a display device.

The ATC automatically determines the at least one location.

Location data of the at least one location is manually entered.

The at least one sensor measures in real-time display device poses.

The ATC automatically adapts to changes in the display device poses.

At least one tag of the plurality of tags is affixed to at least one object of the plurality of objects.

The at least one tag comprises a plurality of tags affixed to an object.

The plurality of sensors measure in real-time object poses of the at least one object using information of the at least one tag.

The ATC automatically adapts to changes in the object poses.

The ATC generates a model of a pose and a physical size of the at least one object.

The pose comprises a six-degree-of-freedom (DOF) pose.

The at least one tag is affixed to at least one location on a periphery of the at least one object, wherein the at least one object is a display device.

The ATC automatically determines the at least one location.

Location data of the at least one location is manually entered.

The plurality of sensors measure in real-time display device poses using information of the at least one tag.

The ATC automatically adapts to changes in the display device poses.

At least one sensor of the plurality of sensors measures in real-time object poses of at least one object of the plurality of objects, wherein the at least one object is a marked object.

The marked object is marked using a tagged object, wherein the tagged object comprises a tag affixed to an object.

The marked object is marked when the tagged object is placed in direct contact with at least one location on the at least one object.

The at least one location comprises a plurality of locations on the marked object.

The plurality of sensors measure poses of the tagged object relative to the marked object and the SOE.

The poses of the tagged object sensed at the plurality of locations represent poses of the marked object.

The marked object is marked when the tagged object is pointed at a plurality of locations on the at least one object.

The plurality of sensors measure poses of the tagged object relative to the marked object and the SOE.

The poses of the tagged object represent poses of the marked object.

The poses of the tagged object represent poses of the marked object at points in time that correspond to when the tagged object is pointed at the plurality of locations.

The at least one feature includes an optical fiducial.

The at least one feature includes a light-emitting diode (LED).

The at least one feature includes an infrared (IR) light-emitting diode (LED).

The at least one feature includes a marker comprising retro-reflective material.

The at least one feature includes a marker comprising at least one region containing at least one color.

The at least one feature includes a plurality of collinear markers.

A tag comprises a linear-partial-tag (LPT) that includes a plurality of collinear markers.

The plurality of collinear markers conveys an identity of the tag.

A tag comprises a plurality of LPTs, wherein each LPT includes a plurality of collinear markers.

A tag comprises a first LPT positioned on a substrate adjacent to a second LPT, wherein the first LPT includes a first set of collinear markers and the second LPT includes a second set of collinear markers.

The first set includes four (4) collinear markers, and the second set includes four (4) collinear markers.

The plurality of sensors comprise at least one camera, and the feature data comprises a projective image acquired by the at least one camera, wherein the projective image includes the tag.

The system comprises searching the projective image and identifying the first LPT in the projective image.

The system comprises fitting a line to the first set of collinear markers of the first LPT.

The system comprises computing a cross ratio of the first set of collinear markers, wherein the cross ratio is a function of pairwise distances between the plurality of collinear markers of the first set of collinear markers.

The system comprises comparing the cross ratio to a set of cross ratios that correspond to a set of known LPTs.

The system comprises searching the projective image and identifying the second LPT, and combining the first LPT and the second LPT into a tag candidate.

The system comprises computing a set of pose hypotheses corresponding to the tag candidate.

The pose hypotheses comprise six-degree-of-freedom (DOF) poses.

The system comprises computing a confidence metric that is a re-projection error of a pose of the set of pose hypotheses.

The confidence metric is given by an equation $$E_r = \frac{1}{p}\sum_{i=1}^{P} (u_i - C(P \cdot x_i))^2$$

where p is a number of collinear markers in the tag, $u_i \in \mathbb{R}^2$ is the measured pixel position of a collinear marker in the projective image, $x_i \in \mathbb{R}^3$ is a corresponding ideal position of the collinear marker in a coordinate frame of the tag, P is a matrix representing the pose, and $C: \mathbb{R}^3 \to \mathbb{R}^2$ is a camera model of the at least one camera.

The at least one camera collects correspondence data between image coordinates of the projective image and the plurality of collinear markers.

The system comprises a camera calibration application, wherein intrinsic parameters of the at least one camera are modeled using the camera calibration application, wherein the intrinsic parameters include at least one of focal ratio, optical center, skewness, and lens distortion.

An input to the camera calibration application includes the correspondence data.

The processor automatically detects a gesture of a body from the feature data received via the plurality of sensors, wherein the plurality of objects includes the body, wherein the feature data is absolute three-space location data of an instantaneous state of the body at a point in time and space, the detecting comprising aggregating the feature data, and identifying the gesture using only the feature data.

The controlling includes controlling at least one of a function of an application running on the processor, a component displayed by the processor, and a component coupled to the processor.

The processor translates the gesture to a gesture signal, and controls a component coupled to the processor in response to the gesture signal.

The detecting comprises identifying the gesture, wherein the identifying includes identifying a pose and an orientation of a portion of the body.

The translating comprises translating information of the gesture to a gesture notation.

The gesture notation represents a gesture vocabulary, and the gesture signal comprises communications of the gesture vocabulary.

The gesture vocabulary represents in textual form instantaneous pose states of kinematic linkages of the body.

The gesture vocabulary represents in textual form an orientation of kinematic linkages of the body.

The gesture vocabulary represents in textual form a combination of orientations of kinematic linkages of the body.

The gesture vocabulary includes a string of characters that represent a state of kinematic linkages of the body.

Controlling the component comprises controlling a three-space object in six degrees of freedom simultaneously by mapping the gesture to the three-space object, wherein the plurality of objects includes the three-space object.

The three-space object is presented on a display device coupled to the processor.

The three-space object is coupled to the processor.

The system comprises controlling movement of the three-space object by mapping a plurality of gestures to a plurality of object translations of the three-space object.

The detecting comprises detecting when an extrapolated position of the object intersects virtual space, wherein the virtual space comprises space depicted on a display device coupled to the processor.

Controlling the component comprises controlling a virtual object in the virtual space when the extrapolated position intersects the virtual object.

Controlling the component comprises controlling a position of the virtual object in the virtual space in response to the extrapolated position in the virtual space.

Controlling the component comprises controlling attitude of the virtual object in the virtual space in response to the gesture.

Embodiments described herein include a method comprising affixing a plurality of tags to a plurality of objects. The plurality of tags includes a plurality of features such that each tag comprises at least one feature. The method includes defining a spatial operating environment (SOE) by locating a plurality of sensors. The SOE includes the plurality of objects. The method includes detecting the plurality of features with the plurality of sensors. The method includes receiving from each sensor of the plurality of sensors feature data corresponding to each object of the plurality of objects detected by the respective sensor. The method includes generating and maintaining a coherent model of relationships between the plurality of objects and the SOE by integrating the feature data from the plurality of sensors.

Embodiments described herein include a method comprising: affixing a plurality of tags to a plurality of objects, the plurality of tags including a plurality of features such that each tag comprises at least one feature; defining a spatial operating environment (SOE) by locating a plurality of sensors, wherein the SOE includes the plurality of objects; detecting the plurality of features with the plurality of sensors; receiving from each sensor of the plurality of sensors feature data corresponding to each object of the plurality of objects detected by the respective sensor; and generating and maintaining a coherent model of relationships between the plurality of objects and the SOE by integrating the feature data from the plurality of sensors.

The coherent model includes spatial relationships between the plurality of objects.

The coherent model includes at least one of location, orientation, and motion of the plurality of objects.

The coherent model includes location, orientation, and motion of the plurality of objects.

The method comprises generating coincidence between a virtual space and physical space that includes the SOE.

The detecting comprises detecting from at least one tag a pose comprising location and orientation of the at least one tag relative to the sensor, wherein the pose comprises a six-degree-of-freedom (DOF) pose.

The plurality of objects include at least one of a body, an appendage of a body, a device, an article of clothing, a glove, a display device, a piece of furniture.

The method comprises defining an origin of the coherent model relative to a particular sensor of the plurality of sensors.

The method comprises defining an origin of the coherent model relative to a particular tag of the plurality of tags, wherein the particular tag has a fixed pose relative to the SOE.

The method comprises defining an origin of the coherent model relative to a particular sensor of the plurality of sensors and a particular tag of the plurality of tags, wherein the particular tag has a fixed pose relative to the SOE.

Each tag of the plurality of tags comprises at least one feature that is detected and localized by the plurality of sensors.

Each tag includes at least one of labeling information, identity information, and pose information.

Each tag includes labeling information, identity information, and pose information.

A projective image of a tag includes labeling, wherein the at least one feature comprises at least one marker, wherein the labeling relates at least one point in the projective image to at least one corresponding marker.

A projective image of a tag includes identity, wherein the at least one feature comprises a plurality of markers on the tag, wherein the identity distinguishes a first tag of the plurality of tags from a second tag of the plurality of tags.

A projective image of a tag includes pose information, wherein the pose information includes translation information and rotation information.

The translation information includes a three-degree-of-freedom translation, wherein the rotation information includes a three-degree-of-freedom rotation.

The pose information relates a position and orientation of a tag to a position and orientation of the SOE.

The method comprises estimating with each sensor a pose of each tag within a sensing volume, wherein each sensor corresponds to a respective sensing volume in the SOE.

The pose comprises at least one of location of a tag and orientation of a tag.

The pose comprises location of a tag and orientation of a tag, wherein the location and the orientation are relative to each respective sensor.

The sensing volume of each sensor at least partially overlaps with the sensing volume of at least one other sensor of the plurality of sensors, wherein a combined sensing volume of the plurality of sensors is contiguous.

The feature data is synchronized.

The method comprises generating for each sensor of the plurality of sensors a pose model of a pose relative to the SOE, wherein the pose comprises a six-degree-of-freedom (DOF) pose.

The method comprises generating a spatial relationship between the plurality of sensors when a plurality of sensors all detect a first tag at an instant in time, and updating the coherent model using the spatial relationship.

The method comprises defining an origin of the coherent model relative to a particular tag of the plurality of tags, wherein the particular tag has a fixed pose relative to the SOE.

The method comprises defining an origin of the coherent model relative to a particular sensor of the plurality of sensors and a particular tag of the plurality of tags, wherein the particular tag has a fixed pose relative to the SOE.

The method comprises determining correct pose models for each sensor.

The method comprises tracking a tag by a sensor at a plurality of points in time and generating a plurality of pose models for the tag. The method comprises generating a plurality of confidence metrics for the plurality of pose models and culling the plurality of pose models based on the plurality of confidence metrics to remove any inconsistent pose models.

The method comprises tracking a tag by a plurality of sensors at a plurality of points in time and developing a plurality of sets of pose models for the tag, wherein each set of pose models comprises a plurality of pose models corresponding to each point in time.

The method comprises generating a plurality of confidence metrics for the plurality of pose models of each set of pose models, and culling the plurality of sets of pose models based on the plurality of confidence metrics to remove any inconsistent pose models.

An average hypothesis comprises an average of the plurality of pose models of each set of pose models, wherein the average hypothesis approximates a maximum likelihood estimate for a true pose of a corresponding tag.

The average hypothesis comprises at least one of a positional component and a rotational component.

The average hypothesis comprises a positional component and a rotational component.

The method comprises determining the positional component using a first equation $$x_{avg}(t_n) = \frac{1}{m}[x_1(t_n) + x_2(t_n) + \ldots + x_m(t_n)]$$

where $t_n$ is a point in time at which the hypotheses $x_i \in \mathbb{R}^3$ are measured, and m, is a number of sensors detecting the tag at a point in time, comprising approximating the rotational component by applying the first equation to unit direction vectors that form a basis of a rotating coordinate frame within the SOE, and re-normalizing the unit direction vectors.

The method comprises generating a smoothed hypothesis by applying a correction factor to the average hypothesis.

The method comprises generating the smoothed hypothesis when at least one additional sensor detects a tag, wherein the at least one additional sensor has not previously detected the tag.

The method comprises generating the smoothed hypothesis when at least one sensor of the plurality of sensors ceases detecting a tag, wherein the at least one additional sensor has previously detected the tag.

The smoothed hypothesis comprises at least one of a positional component and a rotational component.

The smoothed hypothesis comprises a positional component and a rotational component.

The method comprises determining the positional component using a second equation $$x_{sm}(t_n, t_{n-1}) = \frac{1}{m}[x_1(t_n) + c_1(t_{n-1}) + x_2(t_n) + c_2(t_{n-1}) + \ldots + x_m(t_n) + c_m(t_{n-1})]$$

where $t_n$ is a point in time at which the hypotheses $x_i \in \mathbb{R}^3$ are measured, m is a number of sensors detecting the tag at that instant, and c: is a correction factor.

The method comprises applying the correction factor to the average hypothesis, wherein the correction factor is a vector defined as $$c_i(t_n, t_{n-1}) = k(x_{avg}(t_n) - x_i(t_n)) + (1-k)(x_{sm}(t_{n-1}) - x_i(t_{n-1}))$$

where k is a constant selected between 0 and 1.

The method comprises selecting a value of the constant k to provide the coherent model with relatively high accuracy when an object having a tag affixed undergoes fine manipulation and coarse motions.

The method comprises selecting the constant k: to be much less than 1.

The method comprises selecting the constant k so that a corrected hypothesis $x_i + c_i$ is relatively close to the smoothed hypothesis.

The method comprises selecting the constant k to be greater than zero to force the smoothed hypothesis towards the average hypothesis at each time period.

The method comprises varying a value of the constant k so that the smoothed hypothesis remains relatively spatially accurate during a relatively large motion of the tag between time periods.

The method comprises selecting a value of the constant k to be relatively small so that the smoothed hypothesis maintains relatively greater spatial and temporal smoothness during a time period when a motion of the tag is relatively small.

The method comprises approximating the rotational component by applying the second equation to unit direction vectors that form a basis of a rotating coordinate frame within the SOE, and re-normalizing the unit direction vectors.

The method comprises measuring in real-time object poses of at least one object of the plurality of objects using at least one sensor of the plurality of sensors.

The at least one sensor comprises a plurality of sensors affixed to an object.

The at least one sensor is affixed to the at least one object.

The method comprises automatically adapting to changes in the object poses.

The method comprises generating a model of a pose and a physical size of the at least one object, wherein the pose comprises a six-degree-of-freedom (DOF) pose.

The method comprises affixing the at least one sensor to at least one location on a periphery of the at least one object, wherein the at least one object is a display device.

The method comprises automatically determining the at least one location.

Location data of the at least one location is manually entered.

The method comprises measuring display device poses in real-time using the at least one sensor, and automatically adapting to changes in the display device poses.

The method comprises affixing at least one tag of the plurality of tags to at least one object of the plurality of objects.

The at least one tag comprises a plurality of tags affixed to an object.

The method comprises measuring in real-time with the plurality of sensors object poses of the at least one object using information of the at least one tag.

The method comprises automatically adapting to changes in the object poses.

The method comprises generating a model of a pose and a physical size of the at least one object, wherein the pose comprises a six-degree-of-freedom (DOF) pose.

The method comprises affixing the at least one tag to at least one location on a periphery of the at least one object, wherein the at least one object is a display device.

The method comprises automatically determining the at least one location.

Location data of the at least one location is manually entered.

The method comprises measuring in real-time with the plurality of sensors display device poses using information of the at least one tag, and automatically adapting to changes in the display device poses.

The method comprises measuring in real-time with the plurality of sensors object poses of at least one object of the plurality of objects, wherein the at least one object is a marked object.

The method comprises marking the marked object using a tagged object, wherein the tagged object comprises a tag affixed to an object.

The method comprises marking the marked object when the tagged object is placed in direct contact with at least one location on the at least one object.

The method comprises measuring with the plurality of sensors poses of the tagged object relative to the marked object and the SOE, wherein the at least one location comprises a plurality of locations on the marked object, wherein the poses of the tagged object sensed at the plurality of locations represent poses of the marked object.

The method comprises marking the marked object when the tagged object is pointed at a plurality of locations on the at least one object.

The method comprises measuring with the plurality of sensors poses of the tagged object relative to the marked object and the SOE, wherein the poses of the tagged object represent poses of the marked object, wherein the poses of the tagged object represent poses of the marked object at points in time that correspond to when the tagged object is pointed at the plurality of locations.

The at least one feature includes at least one of an optical fiducial, a light-emitting diode (LED), an infrared (IR) light-emitting diode (LED), a marker comprising retro-reflective material, a marker comprising at least one region containing at least one color, and a plurality of collinear markers.

A tag comprises a linear-partial-tag (LPT) that includes a plurality of collinear markers.

The method comprises conveying with the plurality of collinear markers an identity of the tag.

A tag comprises a plurality of LPTs, wherein each LPT includes a plurality of collinear markers, wherein a tag comprises a first LPT positioned on a substrate adjacent to a second LPT, wherein the first LPT includes a first set of collinear markers and the second LPT includes a second set of collinear markers.

The plurality of sensors comprise at least one camera, and the feature data comprises a projective image acquired by the at least one camera, wherein the projective image includes the tag.

The method comprises searching the projective image and identifying the first LPT in the projective image, and fitting a line to the first set of collinear markers of the first LPT.

The method comprises computing a cross ratio of the first set of collinear markers, wherein the cross ratio is a function of pairwise distances between the plurality of collinear markers of the first set of collinear markers, and comparing the cross ratio to a set of cross ratios that correspond to a set of known LPTs.

The method comprises searching the projective image and identifying the second LPT, and combining the first LPT and the second LPT into a tag candidate, and computing a set of pose hypotheses corresponding to the tag candidate.

The method comprises computing a confidence metric that is a re-projection error of a pose of the set of pose hypotheses.

The confidence metric is given by an equation $$E_r = \frac{1}{p}\sum_{i=1}^{p}(u_i - C(P \cdot x_i))^2$$

where p is a number of collinear markers in the tag, $u_i \in \mathbb{R}^2$ is the measured pixel position of a collinear marker in the projective image, $x_i \in \mathbb{R}^3$ is a corresponding ideal position of the collinear marker in a coordinate frame of the tag, P is a matrix representing the pose, and $C: \mathbb{R}^3 \rightarrow \mathbb{R}^2$ is a camera model of the at least one camera.

The at least one camera collects correspondence data between image coordinates of the projective image and the plurality of collinear markers.

The method comprises a camera calibration application, wherein intrinsic parameters of the at least one camera are modeled using the camera calibration application, wherein the intrinsic parameters include at least one of focal ratio, optical center, skewness, and lens distortion.

An input to the camera calibration application includes the correspondence data.

The method comprises automatically detecting a gesture of a body from the feature data received via the plurality of sensors, wherein the plurality of objects includes the body, wherein the feature data is absolute three-space location data of an instantaneous state of the body at a point in time and space, the detecting comprising aggregating the feature data, and identifying the gesture using only the feature data.

The controlling includes controlling at least one of a function of an application, a display component, and a remote component.

The method comprises translating the gesture to a gesture signal, and controlling a component in response to the gesture signal.

The detecting comprises identifying the gesture, wherein the identifying includes identifying a pose and an orientation of a portion of the body.

The translating comprises translating information of the gesture to a gesture notation, wherein the gesture notation represents a gesture vocabulary, and the gesture signal comprises communications of the gesture vocabulary.

The gesture vocabulary represents in textual form at least one of instantaneous pose states of kinematic linkages of the body, an orientation of kinematic linkages of the body, and a combination of orientations of kinematic linkages of the body.

The gesture vocabulary includes a string of characters that represent a state of kinematic linkages of the body.

Controlling the component comprises controlling a three-space object in six degrees of freedom simultaneously by mapping the gesture to the three-space object, wherein the plurality of objects includes the three-space object.

The method comprises presenting the three-space object on a display device.

The method comprises controlling movement of the three-space object by mapping a plurality of gestures to a plurality of object translations of the three-space object.

The detecting comprises detecting when an extrapolated position of the object intersects virtual space, wherein the virtual space comprises space depicted on a display device.

Controlling the component comprises controlling a virtual object in the virtual space when the extrapolated position intersects the virtual object.

Embodiments described herein include a system comprising a plurality of tags affixed to a plurality of objects. The plurality of tags includes a plurality of features such that each tag comprises at least one feature. The system includes a plurality of sensors. A location of the plurality of sensors defines a spatial operating environment (SOE) that includes the plurality of objects. The system includes an adaptive tracking component (ATC) running on a processor. The ATC receives from each sensor of the plurality of sensors feature data corresponding to each object of the plurality of objects detected by the respective sensor. The feature data is absolute three-space location data of an instantaneous state of the respective body at a point in time and space. The ATC generates and maintains a coherent model of relationships between the plurality of objects and the SOE by integrating the feature data from the plurality of sensors. The ATC automatically detects from the feature data a gesture of at least one object of the plurality of objects. The detecting comprises identifying the gesture using only the feature data.

Embodiments described herein include a system comprising: a plurality of tags affixed to a plurality of objects, wherein the plurality of tags include a plurality of features such that each tag comprises at least one feature; a plurality of sensors, wherein a location of the plurality of sensors defines a spatial operating environment (SOE) that includes the plurality of objects; and an adaptive tracking component (ATC) running on a processor, wherein the ATC receives from each sensor of the plurality of sensors feature data corresponding to each object of the plurality of objects detected by the respective sensor, wherein the feature data is absolute three-space location data of an instantaneous state of the respective body at a point in time and space, wherein the ATC generates and maintains a coherent model of relationships between the plurality of objects and the SOE by integrating the feature data from the plurality of sensors, wherein the ATC automatically detects from the feature data a gesture of at least one object of the plurality of objects, the detecting comprising identifying the gesture using only the feature data.

The coherent model includes spatial relationships between the plurality of objects.

The coherent model includes at least one of location, orientation, and motion of the plurality of objects.

The ATC generates coincidence between virtual space and physical space that includes the SOE.

A sensor detects from at least one tag a pose comprising location and orientation of the at least one tag relative to the sensor, wherein the pose comprises a six-degree-of-freedom (DOF) pose.

The plurality of objects include at least one of a body, an appendage of a body, a device, an article of clothing, a glove, a display device, a piece of furniture.

An origin of the coherent model is defined relative to a particular sensor of the plurality of sensors.

An origin of the coherent model is defined relative to a particular tag of the plurality of tags, wherein the particular tag has a fixed pose relative to the SOE.

An output of the ATC controls at least one of a function of an application, a display component, and a remote component coupled to the processor.

The system comprises translating the gesture to a gesture signal, and controlling a component coupled to the processor in response to the gesture signal.

The detecting comprises identifying the gesture, wherein the identifying includes identifying a pose and an orientation of a portion of the object.

The translating comprises translating information of the gesture to a gesture notation, wherein the gesture notation represents a gesture vocabulary, and the gesture signal comprises communications of the gesture vocabulary.

The gesture vocabulary represents in textual form at least one of instantaneous pose states of kinematic linkages of the object, an orientation of kinematic linkages of the object, and a combination of orientations of kinematic linkages of the object.

The gesture vocabulary includes a string of characters that represent a state of kinematic linkages of the object.

Controlling the component comprises controlling a three-space object in six degrees of freedom simultaneously by mapping the gesture to the three-space object, wherein the plurality of objects includes the three-space object.

The system comprises presenting the three-space object on a display device.

The system comprises controlling movement of the three-space object by mapping a plurality of gestures to a plurality of object translations of the three-space object.

The detecting comprises detecting when an extrapolated position of the object intersects virtual space, wherein the virtual space comprises space depicted on a display device.

Controlling the component comprises controlling a virtual object in the virtual space when the extrapolated position intersects the virtual object.

The system comprises detecting an event of a source device, wherein the event includes the gesture and the source device includes the ATC running on the processor, generating at least one data sequence comprising device event data specifying the event and state information of the event, wherein the device event data and state information are type-specific data having a type corresponding to an application of the source device, and forming a data capsule to include the at least one data sequence, the data capsule having a data structure comprising an application-independent representation of the at least one data sequence.

The generating of the at least one data sequence comprises: generating a first respective data set that includes first respective device event data; generating a second respective data set that includes second respective state information; and forming a first data sequence to include the first respective data set and the second respective data set.

The generating of the first respective data set includes forming the first respective data set to include identification data of the source device, the identification data including data identifying the source device.

The generating of the at least one data sequence comprises: generating a first respective data set that includes first respective device event data; generating a second respective data set that includes second respective state information; and forming a second data sequence to include the first respective data set and the second respective data set.

The generating of the first respective data set includes generating a first respective data set offset, wherein the first respective data set offset points to the first respective data set of the second data sequence.

The generating of the second respective data set includes generating a second respective data set offset, wherein the second respective data set offset points to the second respective data set of the second data sequence.

The first respective data set is a description list, the description list including a description of the data.

The device event data is a tagged byte-sequence representing typed data, wherein the device event data includes a type header and a type-specific data layout.

The state information is a tagged byte-sequence representing typed data, wherein the state information includes a type header and a type-specific data layout.

The system comprises generating at least one offset. The system comprises forming the data capsule to include the at least one offset.

The system comprises generating a first offset having a first variable length. The first offset points to the device event data of a first data sequence of the at least one data sequence.

The system comprises generating a second offset having a second variable length. The second offset points to the state information of a first data sequence of the at least one data sequence.

The system comprises forming a first code path through the data capsule using a first offset of the at least one offset.

The system comprises forming a second code path through the data capsule using a second offset of the at least one offset. The first code path and the second code path are different paths.

At least one of the first offset and the second offset include metadata, the metadata comprising context-specific metadata corresponding to a context of the application.

The system comprises generating a header that includes a length of the data capsule. The system comprises forming the data capsule to include the header.

The system comprises transferring the data capsule to a repository coupled to the processor.

The system comprises detecting a second event of a second source device. The system comprises searching the repository for data capsules corresponding to the second event.

The system comprises identifying a correspondence between the data capsule and the second event. The system comprises extracting the data capsule from the repository in response to the identifying. The system comprises executing on behalf of the second source device a processing operation corresponding to the second event on behalf of the second source device in response to contents of the data capsule, wherein the source device corresponds to an application of a first type and the second source device corresponds to a second application of a second type.

The repository is coupled to a plurality of applications, the repository including a plurality of data capsules corresponding to the plurality of applications, the repository providing access to the plurality of data capsules by the plurality of applications, wherein at least two applications of the plurality of applications are different applications.

The repository provides state caching of a plurality of data capsules.

The repository provides linear sequencing of a plurality of data capsules.

The data structure is untyped.

The data structure of the data capsule provides a platform-independent representation of the device event data and the state information, and platform-independent access to the device event data and the state information.

Each tag of the plurality of tags comprises at least one feature that is detected and localized by the plurality of sensors.

Each tag includes at least one of labeling information, identity information, and pose information.

A projective image of a tag includes labeling, wherein the at least one feature comprises at least one marker, wherein the labeling relates at least one point in the projective image to at least one corresponding marker.

A projective image of a tag includes identity, wherein the at least one feature comprises a plurality of markers on the tag, wherein the identity distinguishes a first tag of the plurality of tags from a second tag of the plurality of tags.

A projective image of a tag includes pose information.

The pose information includes translation information and rotation information.

The pose information relates a position and orientation of a tag to a position and orientation of the SOE.

Each sensor corresponds to a sensing volume in the SOE, wherein each sensor estimates a pose of each tag within the sensing volume.

The pose comprises at least one of location and orientation of a tag.

The sensing volume of each sensor at least partially overlaps with the sensing volume of at least one other sensor of the plurality of sensors, wherein a combined sensing volume of the plurality of sensors is contiguous.

The ATC generates for each sensor of the plurality of sensors a pose model of a pose relative to the SOE.

When a plurality of sensors all detect a first tag at an instant in time, the ATC generates a spatial relationship between the plurality of sensors, wherein the ATC updates the coherent model using the spatial relationship.

The ATC defines an origin of the coherent model relative to a particular tag of the plurality of tags, wherein the particular tag has a fixed pose relative to the SOE.

The ATC defines an origin of the coherent model relative to a particular sensor of the plurality of sensors and a particular tag of the plurality of tags, wherein the particular tag has a fixed pose relative to the SOE.

Correct pose models are determined for each sensor.

A tag is tracked by a sensor at a plurality of points in time and a plurality of pose models are generated for the tag, wherein a plurality of confidence metrics are generated for the plurality of pose models and the plurality of pose models are culled based on the plurality of confidence metrics to remove any inconsistent pose models.

A tag is tracked by a plurality of sensors at a plurality of points in time and a plurality of sets of pose models are developed for the tag, wherein each set of pose models comprises a plurality of pose models corresponding to each point in time.

A plurality of confidence metrics are generated for the plurality of pose models of each set of pose models, and the plurality of sets of pose models are culled based on the plurality of confidence metrics to remove any inconsistent pose models.

An average hypothesis comprises an average of the plurality of pose models of each set of pose models, wherein the average hypothesis approximates a maximum likelihood estimate for a true pose of a corresponding tag.

The average hypothesis comprises at least one of a positional component and a rotational component.

A smoothed hypothesis is generated through application of a correction factor to the average hypothesis.

The smoothed hypothesis is generated when at least one additional sensor detects a tag, wherein the at least one additional sensor has not previously detected the tag.

The smoothed hypothesis is generated when at least one sensor of the plurality of sensors ceases detecting a tag, wherein the at least one additional sensor has previously detected the tag.

The smoothed hypothesis comprises at least one of a positional component and a rotational component.

At least one sensor of the plurality of sensors measures in real-time object poses of at least one object of the plurality of objects.

The ATC automatically adapts to changes in the object poses.

The ATC generates a model of a pose and a physical size of the at least one object.

The at least one sensor is affixed to at least one location on a periphery of the at least one object, wherein the at least one object is a display device.

The ATC automatically determines the at least one location.

The at least one sensor measures in real-time display device poses, and the ATC automatically adapts to changes in the display device poses.

At least one tag of the plurality of tags is affixed to at least one object of the plurality of objects.

The plurality of sensors measure in real-time object poses of the at least one object using information of the at least one tag.

The ATC automatically adapts to changes in the object poses.

The ATC generates a model of a pose and a physical size of the at least one object.

The at least one tag is affixed to at least one location on a periphery of the at least one object, wherein the at least one object is a display device.

The ATC automatically determines the at least one location.

The plurality of sensors measure in real-time display device poses using information of the at least one tag.

The ATC automatically adapts to changes in the display device poses.

At least one sensor of the plurality of sensors measures in real-time object poses of at least one object of the plurality of objects, wherein the at least one object is a marked object.

The marked object is marked using a tagged object, wherein the tagged object comprises a tag affixed to an object.

The marked object is marked when the tagged object is placed in direct contact with at least one location on the at least one object.

The at least one location comprises a plurality of locations on the marked object.

The plurality of sensors measure poses of the tagged object relative to the marked object and the SOE, wherein the poses of the tagged object sensed at the plurality of locations represent poses of the marked object.

The marked object is marked when the tagged object is pointed at a plurality of locations on the at least one object.

The plurality of sensors measure poses of the tagged object relative to the marked object and the SOE, wherein the poses of the tagged object represent poses of the marked object at points in time that correspond to when the tagged object is pointed at the plurality of locations.

The at least one feature includes at least one of an optical fiducial, a light-emitting diode (LED), an infrared (IR) light-emitting diode (LED), a marker comprising retro-reflective material, a marker comprising at least one region containing at least one color, and a plurality of collinear markers.

A tag comprises a linear-partial-tag (LPT) that includes a plurality of collinear markers, wherein the plurality of collinear markers convey an identity of the tag.

A tag comprises a plurality of LPTs, wherein each LPT includes a plurality of collinear markers.

A tag comprises a first LPT positioned on a substrate adjacent to a second LPT, wherein the first LPT includes a first set of collinear markers and the second LPT includes a second set of collinear markers.

The plurality of sensors comprise at least one camera, and the feature data comprises a projective image acquired by the at least one camera, wherein the projective image includes the tag.

The system comprises searching the projective image and identifying the first LPT in the projective image, and fitting a line to the first set of collinear markers of the first LPT.

The system comprises computing a cross ratio of the first set of collinear markers, wherein the cross ratio is a function of pairwise distances between the plurality of collinear markers of the first set of collinear markers, and comparing the cross ratio to a set of cross ratios that correspond to a set of known LPTs.

The system comprises searching the projective image and identifying the second LPT, and combining the first LPT and the second LPT into a tag candidate, and computing a set of pose hypotheses corresponding to the tag candidate, and computing a confidence metric that is a re-projection error of a pose of the set of pose hypotheses.

The at least one camera collects correspondence data between image coordinates of the projective image and the plurality of collinear markers.

The system comprises a camera calibration application, wherein intrinsic parameters of the at least one camera are modeled using the camera calibration application, wherein the intrinsic parameters include at least one of focal ratio, optical center, skewness, and lens distortion.

An input to the camera calibration application includes the correspondence data.

The systems and methods described herein include and/or run under and/or in association with a processing system. The processing system includes any collection of processor-based devices or computing devices operating together, or components of processing systems or devices, as is known in the art. For example, the processing system can include one or more of a portable computer, portable communication device operating in a communication network, and/or a network server.

The portable computer can be any of a number and/or combination of devices selected from among personal computers, cellular telephones, personal digital assistants, portable computing devices, and portable communication devices, but is not so limited. The processing system can include components within a larger computer system.

The processing system of an embodiment includes at least one processor and at least one memory device or subsystem. The processing system can also include or be coupled to at least one database. The term "processor" as generally used herein refers to any logic processing unit, such as one or more central processing units (CPUs), digital signal processors (DSPs), application-specific integrated circuits (ASIC), etc. The processor and memory can be monolithically integrated onto a single chip, distributed among a number of chips or components of a host system, and/or provided by some combination of algorithms. The methods described herein can be implemented in one or more of software algorithm(s), programs, firmware, hardware, components, circuitry, in any combination.

System components embodying the systems and methods described herein can be located together or in separate locations. Consequently, system components embodying the systems and methods described herein can be components of a single system, multiple systems, and/or geographically separate systems. These components can also be subcomponents or subsystems of a single system, multiple systems, and/or geographically separate systems. These components can be coupled to one or more other components of a host system or a system coupled to the host system.

Communication paths couple the system components and include any medium for communicating or transferring files among the components. The communication paths include wireless connections, wired connections, and hybrid wireless/wired connections. The communication paths also include couplings or connections to networks including local area networks (LANs), metropolitan area networks (MANs), wide area networks (WANs), proprietary networks, interoffice or backend networks, and the Internet. Furthermore, the communication paths include removable fixed mediums like floppy disks, hard disk drives, and CD-ROM disks, as well as flash RAM, Universal Serial Bus (USB) connections, RS-232 connections, telephone lines, buses, and electronic mail messages.

Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

The above description of embodiments of the processing environment is not intended to be exhaustive or to limit the systems and methods described to the precise form disclosed. While specific embodiments of, and examples for, the processing environment are described herein for illustrative purposes, various equivalent modifications are possible within the scope of other systems and methods, as those skilled in the relevant art will recognize. The teachings of the processing environment provided herein can be applied to other processing systems and methods, not only for the systems and methods described above.

The elements and acts of the various embodiments described above can be combined to provide further embodiments. These and other changes can be made to the processing environment in light of the above detailed description.

What is claimed is:

1. A method comprising:
 a tracking component of a gestural control system receiving feature data of a first object of a plurality of objects included in a spatial operating environment (SOE) from at least one sensor of a plurality of sensors of the SOE, wherein locations of each of the plurality of sensors define the SOE; and
 the tracking component generating from the received feature data of the first object a coherent model of spatial relationships that includes a spatial relationship between the first object and a second object of the plurality of objects.

2. The method of claim 1, wherein each sensor is a camera.

3. The method of claim 1, wherein at least one sensor is a camera.

4. The method of claim 1, wherein the tracking component receives the feature data of the first object from one sensor of the plurality of sensors, and wherein the one sensor is a camera.

5. The method of claim 1, wherein the plurality of sensors includes two or more cameras, and wherein the tracking component receiving the feature data of the first object comprises the tracking component receiving the feature data of the first object from two or more cameras of the plurality of sensors.

6. The method of claim 1 wherein the first object is a wand.

7. The method of claim 1 wherein the first object is an input device.

8. The method of claim 1 wherein the first object is display device.

9. The method of claim 1 wherein the first object is mobile screen.

10. The method of claim 1, further comprising the tracking component receiving feature data of the second object of the plurality of objects included in the SOE from at least one sensor of the plurality of sensors of the SOE.

11. The method of claim 1, wherein the first object is a wand and the second object is a wand.

12. The method of claim 1, wherein the first object is an input device and the second object is an input device.

13. The method of claim 1, wherein the first object is a wand and the second object is a display device.

14. The method of claim 1, wherein the first object is an input device and the second object is a display device.

15. The method of claim 1, wherein the first object is a wand and the second object is a mobile screen.

16. The method of claim 1, wherein the feature data of the first object is absolute three-space location data of an instantaneous state of the first object at a point in time and space.

17. The method of claim 1, wherein the tracking component receives the feature data of the first object from at least a first sensor and a second sensor of the plurality of sensors.

18. The method of claim 17, wherein the coherent model of spatial relationships includes a spatial relationship between the first sensor and the second sensor.

19. The method of claim 18, wherein the feature data of the first object is absolute three-space location data of an instantaneous state of the first object at a point in time and space.

20. The method of claim 1, wherein the gestural control system includes the plurality of sensors.

* * * * *